United States Patent [19]
Nishitani et al.

[11] Patent Number: 6,120,998
[45] Date of Patent: Sep. 19, 2000

[54] ENDO-XYLOGLUCAN TRANSFERASE

[75] Inventors: Kazuhiko Nishitani, Kagoshima; Kazuhide Okazawa, Otsu; Kiyozo Asada, Shiga-ken; Ikunoshin Kato, Uji, all of Japan

[73] Assignee: Takara Shuzo Co., Ltd., Kyoto, Japan

[21] Appl. No.: 09/052,085

[22] Filed: Mar. 31, 1998

Related U.S. Application Data

[62] Division of application No. 08/445,533, May 22, 1995, Pat. No. 5,840,550, which is a division of application No. 08/381,280, Jan. 31, 1995, Pat. No. 5,516,694, which is a continuation of application No. 08/037,281, Mar. 26, 1993, abandoned, which is a continuation-in-part of application No. 07/929,513, Aug. 14, 1992, abandoned.

[30] Foreign Application Priority Data

| Mar. 26, 1992 | [JP] | Japan | 4-98506 |
| Jul. 24, 1992 | [JP] | Japan | 4-217489 |
| Jan. 28, 1993 | [JP] | Japan | 5-31163 |

[51] Int. Cl.$^7$ ............ C12N 5/04; C12N 15/10; C12Q 1/68; C07H 21/04
[52] U.S. Cl. ............ 435/6; 435/91.1; 435/193; 435/375; 435/325; 435/410; 435/419; 536/24.5; 536/23.1
[58] Field of Search ............ 435/6, 91.1, 193, 435/375, 325, 410, 419; 536/24.5, 23.1, 24.1, 24.3; 800/13, 21, 278

[56] References Cited

U.S. PATENT DOCUMENTS

| 4,675,285 | 6/1987 | Clark et al. | 435/172.3 |
| 5,107,065 | 4/1992 | Shewmaker et al. | 800/205 |

FOREIGN PATENT DOCUMENTS

| 0 240 208 | 10/1987 | WIPO . |
| 9 012 084 | 10/1990 | WIPO . |

OTHER PUBLICATIONS

Branch, TIBS 23, pp. 45–50, Feb. 1998.
Andersen, Nature vol. 392/Supp, pp. 25–30, Apr. 1998.
Journal of Biological Chemistry, vol. 267, No. 29, Oct. 15, 1992, Baltimore, U.S.; pp. 12064–21064, K. Nishitani et al. "Endo–xyloglucan transferase, a novel class of glycosyl-transferase that catalyzes transfer of a segment of xylogucan molecule to another xyloglucan molecule".
Biochemical Journal, vol. 282, No. 3 Mar. 15, 1992, London, GB, pp. 821–828; S.C. Fry et al. "Xyloglucan endot-ransglycosylase, a new wall–loosening enzyme activity form plants".
Physiologia Plantarium, vol. 82 No. 4, 1991, Copenhagen, DK, pp. 490–497; K. Nishitani et al., "In vitro molecular weight increase in xyloglucans by an apoplastic enzyme preparation from epicotyls of Vigna angularis".
Gene, vol. 72, 1988, Amsterdam, NL, pp. 45–50, A.R. Van Der Krol et al., "Antisense genes in plants: an overview".
Asada et al., 1993 FASEB J. (Abstract–Ann. Meeting) p. A1299, Abs. 1439.
Wilke–Douglas et al., 1986, Physiol. Plantarum, 68, pp. 560–565.
Albersheim, (1976) "Plant Biochemistry", pp. 225–274, Academic Press, New York.
Nishitani et al., Physiologiaplantarum, 82, pp. 490–497 (Aug. 15, 1991).
Nishitani et al., Journal of Biological Chemistry, 267, (9), pp. 21058–21064 (Oct. 15, 1992).
Nishitani, K. Plant Cell Physiol. 33:8, pp. 1159–1164 (Dec. 1992).
Scopes (1987) In Protein Purification: Principles and Practice. Springer–Verlag New York, Inc.

*Primary Examiner*—George C. Elliott
*Assistant Examiner*—Melissa Schmidt
*Attorney, Agent, or Firm*—Wenderoth, Lind & Ponack, L.L.P.

[57] ABSTRACT

Endo-xyloglucan transferases responsible for growth of plant cell wall, genes coding for the enzymes, a method of transferring xyloglucan molecules by using the enzyme, and methods of using the gene are described.

28 Claims, 16 Drawing Sheets

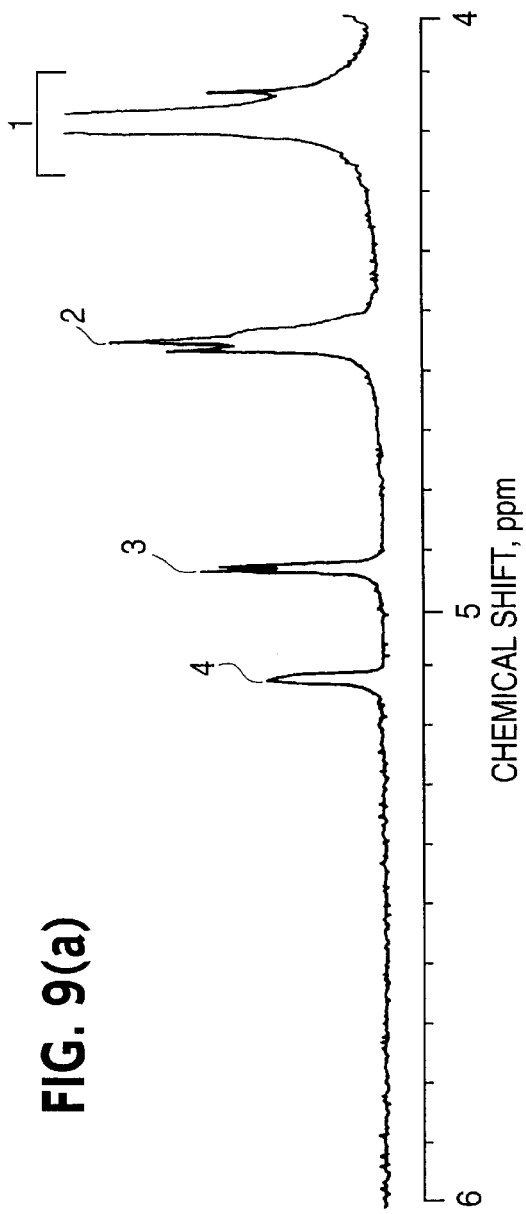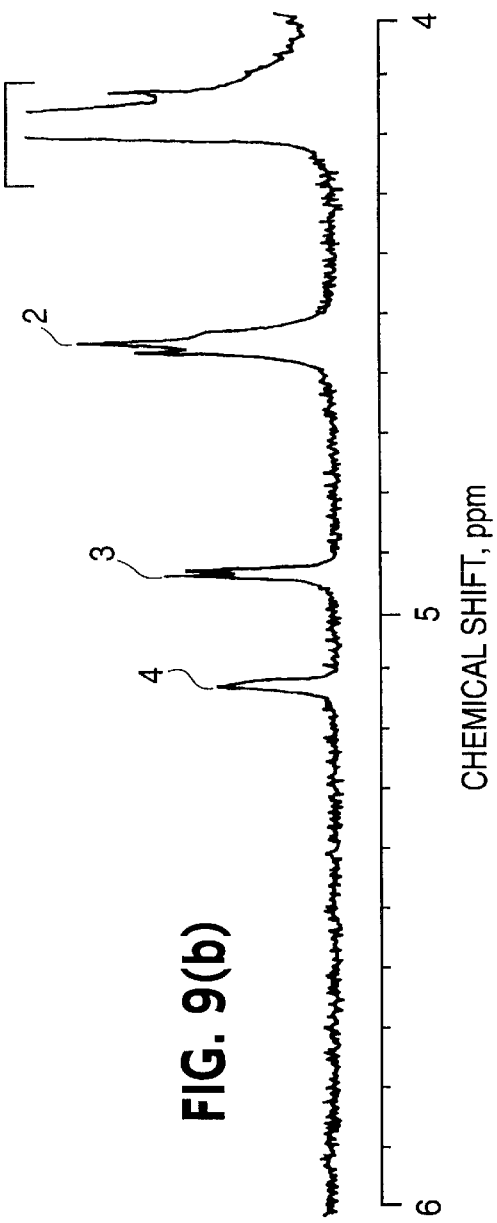

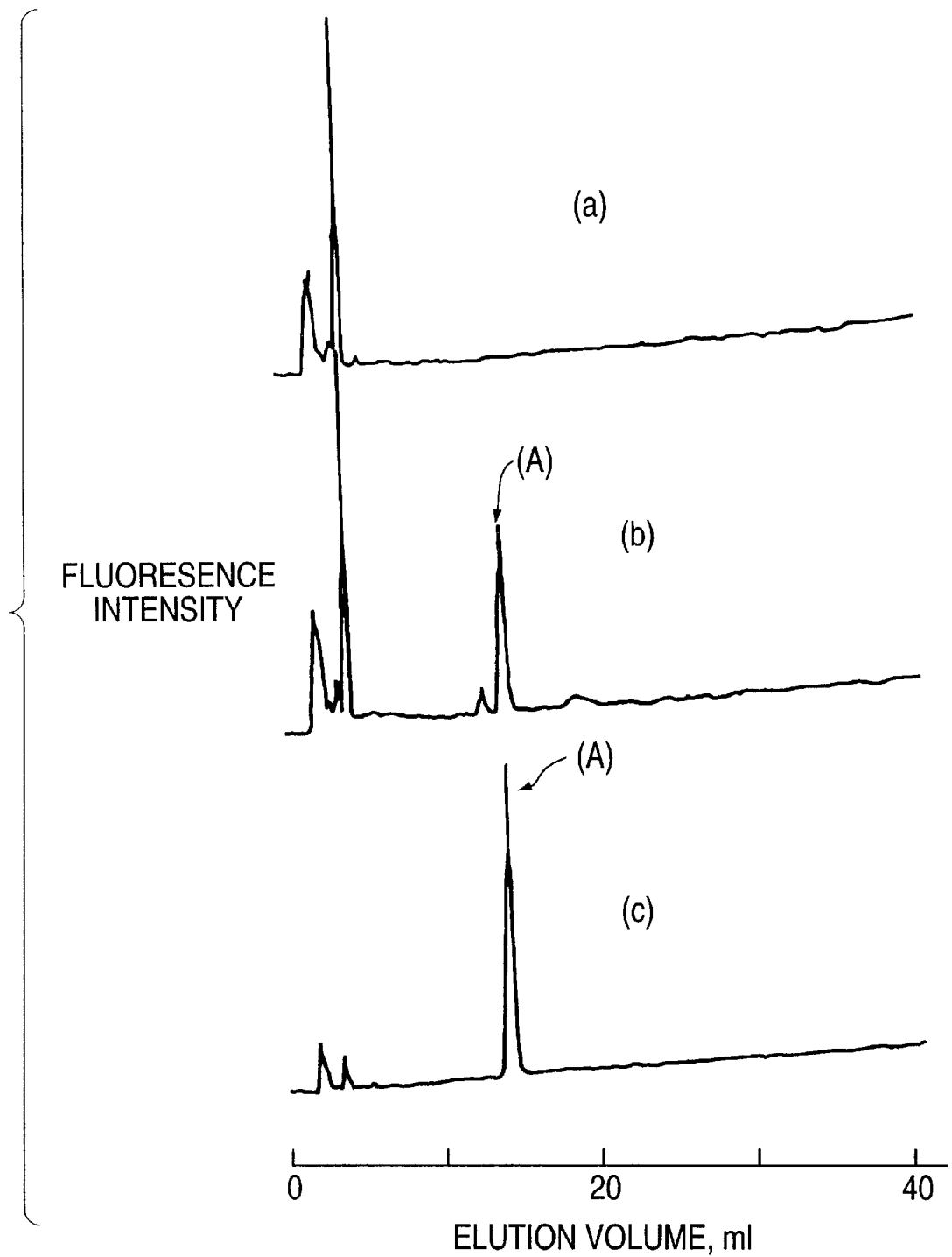

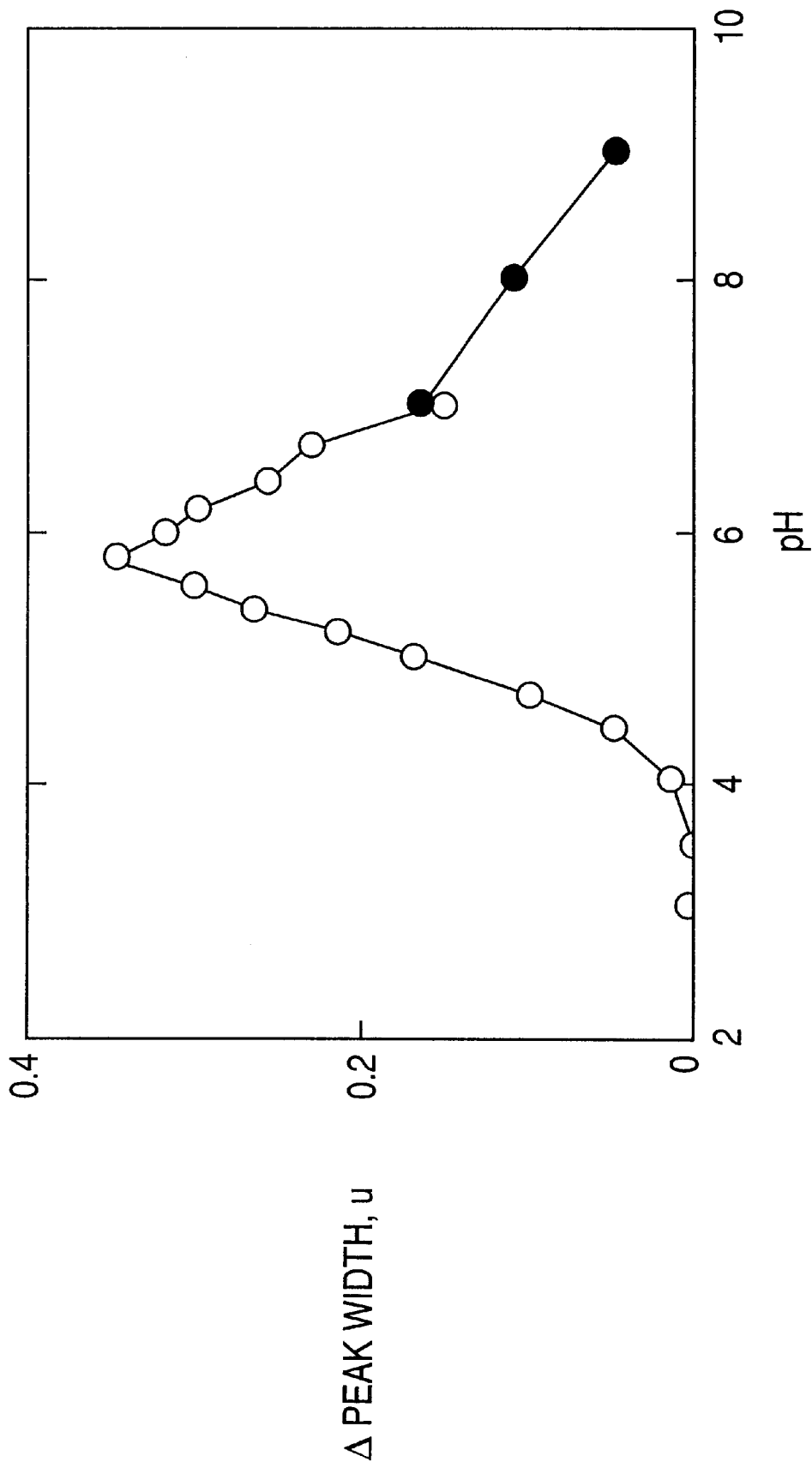

SEQUENCE LISTING (1) GENERAL INFORMATION:

(iii) NUMBER OF SEQUENCES: 27

(2) INFORMATION FOR SEQ ID NO:1:

(i) SEQUENCE CHARACTERISTICS:
      (A) LENGTH: 1133 bases
      (B) TYPE: nucleic acid
      (C) STRANDEDNESS: single
      (D) TOPOLOGY: linear (ii) MOLECULE TYPE: cDNA to mRNA (iii) HYPOTHETICAL: no (iv) ANTI-SENSE: yes (vi) ORIGINAL SOURCE:
      (A) ORGANISM: Vigna angularis (xi) SEQUENCE DESCRIPTION: SEQ ID NO:1:

```
TTTTTTTTTT AACCAGTATA AACTAGTAGT ATTACTAGTA TATTGATTCA GAGTGAAACA      60

GAATTACAGA TACAAATTAA GGCACAGAGC CATATCTGGT ACATAGCCAA ACAGTAGCAG     120

CAATAAATGA TGATATGATT ATCAACAATA CAGGAAGCAA TAGCAAGCTC AAATGAAATC     180

TGTATCAGCA CTTAGGTGGG AACTTTATGG GAGTGTGATA TTGAAAATAA TGAGGCCTTA     240

AAGTATAGGT TAAAATGATT AAATGTCACG GTCTCTGGTG CACTCTGGAG GGACTTGAGA     300

GTAGCGTTTG CGATCAGTGC AGTAGTTGTA GATGGTGTAT TTGTTGCGTA CCCAAGCCAG     360

TTTTTGCCAC TGAGCAGCAT CAAGGTCACG AAACTCTGGT TGATCCCACC ACCTCTTGCC     420

TTGTGTGTCA CAGAACTTGG CATTCACTGA GGCCTCACAC CCATCAATGT GGAAGCCCTT     480

GTAAGAGGCT ATGAAGGGGG CTTTGGACCA ATCTGTTTTC TCCAAACCAC CCCTTGTAGC     540

CCAGTCATCT GCATTCCACA AACTGTTGTA TATTTTCATT GGTTGATTGA AGGGGAACTT     600

CACTCCCAAG TCATTGCTGT TCTTGAACAC CCTTATTGGG TAGTCATCCA CATAGAATAC     660

AATCTGGTAC ATGTTCCATA GCACTGAATA TCTGTGGTAT TGAGTCGTAG GGTCAAACCA     720

GAGGTAGATT CTCTGCTCTC TGTCACCTTT GCCTCCGGTG AACACATTTG TTTGTAAAAT     780
```

| | |
|---|---|
| GTATGGTTGC CCAGTTCTGT TTCCCAAGAA CTCGAAGTCT ATTTCATCAT GTTCTGCGTT | 840 |
| TGTGGACGAT AAATAGAAAG CAGTGACTGT GCCAGCTGAA TCACCAGGAA CCAATTTTAT | 900 |
| GTACATGCTG AAGTGACCAA ACAAGTATGA CCCTTTGGAC TGGAATCCAG TACCAGTGTA | 960 |
| CTTATCGAGA TGAAGCTGAA TCTCAGAACC TCCATTGAGA TATTTGATAT GATCAAAGGC | 1020 |
| CCAAGTAGGC ACATAGTTTC TGCCAAATGG TACATCAATT GGAGTTCTTG GGTTGGCAGC | 1080 |
| GAAAGAAGCA GAAGCCAGTG ATAACAGAAT CAGACAAGTC CACAAAGAAG AAC | 1133 |

(2) INFORMATION FOR SEQ ID NO:2:

(i) SEQUENCE CHARACTERISTICS:
        (A) LENGTH: 957 bases
        (B) TYPE: nucleic acid
        (C) STRANDEDNESS: single
        (D) TOPOLOGY: linear (ii) MOLECULE TYPE: cDNA to mRNA (iii) HYPOTHETICAL: no (iv) ANTI-SENSE: yes (vi) ORIGINAL SOURCE:
        (A) ORGANISM: Glycine max (xi) SEQUENCE DESCRIPTION: SEQ ID NO:2:

| | |
|---|---|
| TGAAAAGAGA AGCAACAATA ATAAAGTGAA TGAGAAATTT AAATATCACG GACTAAAATA | 60 |
| TCTATTCACT CGAAATTTAA ATGTCACGGT CTCTTTTGCA CTCAGGAGGA GAGATATGAG | 120 |
| GATAGCGTTT AGTGTCAGTG CAGTAGTTGT AGATGGTGTA TTTCTGGCGC ACCCATCTGA | 180 |
| GCCTACGCCA CTGGGCGGCG TCAAGGTCAC GGAACTCAGG CTGGTCCCAC CACCTCTTGC | 240 |
| CCTGCGTGTC GCAGAACTTG GCGTTCACCG AAGCCTCGCA CCCGTCGATG TGAAACCCCT | 300 |
| TGTACGCTGC TATGAAGGGT GCTTTCGACC AATCCGTTTT CTCCAAACCA CCCCTCGTTG | 360 |
| CCCAGTCATC AGCGTTCCAC AAACTGTTGT AGATCTTCAT TGGCTGGTCG AATGGGAATT | 420 |
| TCACTCCCAA GTCCTTGCTG TTCTTGAACA CCCTGATTGG CACCTCGTCC ACAAAGAACA | 480 |
| CAATCTGATA CAAGTTCCAG AGAATGGAGT ATCTGTGGTA TTCTTTCGTG GGATCAAACC | 540 |
| AGAGATAGAT TCTTTGCTCT CTATCACCCT TGCCTCCGGT GAACACATTT GTTTGCAGAA | 600 |
| TGTAAGGTTG TCCTGTTCTG TTCCCCAAGA ACTCAAAGTC TATCTCATCA TGCTCCGCGT | 660 |
| TTTGGGAAGA TAAATAGAAA GCAGTGACTG TGCCAGCAGA ATCTCCAGGA ACCATCTTTA | 720 |
| TGTACATGCT GAAGTGACCA AACAAGTAAG ACCCTTTGGA CTGGAAGCCA GTACCAGTGT | 780 |
| ACTTGTCAAG ATGAAGCTGA ATGTCAGAAC CACCATTGAA ATATTTGATG TGATCAAAGG | 840 |
| CCCATGTGGG CACGTAGTTT CGGCCAAATT GTACATCCAC TGGCCTGCGT GGGTTGGCAC | 900 |
| AGAGTGCTGC AGAGGCCAGT GATGCCAAAA TCACACACAC CGTCCACACA GAAAAAA | 957 |

(2) INFORMATION FOR SEQ ID NO:3:

(i) SEQUENCE CHARACTERISTICS:
        (A) LENGTH: 1320 bases
        (B) TYPE: nucleic acid
        (C) STRANDEDNESS: single
        (D) TOPOLOGY: linear (ii) MOLECULE TYPE: cDNA to mRNA (iii) HYPOTHETICAL: no (iv) ANTI-SENSE: yes (vi) ORIGINAL SOURCE:
    (A) ORGANISM: Arabidopsis thaliana (xi) SEQUENCE DESCRIPTION: SEQ ID NO:3:

```
TTTTTTTTTT TTTTTTATGA AAATACATAG CTAATCAATA CATATATGAA TTATAACATG     60

TAATTTTAGG CCCAAATATA GCATAAACAT CATGGGCCAA CAAACAATAC ATATATCAAT    120

CTCTTGAACA AGCATAATTC AAATAATAAT GATAGCATAA ATTCATTAAA ACCCTCAAGA    180

GTAGTAACTT ATGCGTCTCT GTCCCTTTTA CATTCAGCTG GCATAACCGG GAACCTAGTC    240

CGGTCGGTAC AGTAGTTGTA GATGGTCCAC TTCATACGAA CCCATTTGAG ACGACGCCAT    300

TGTTCAGCGT CAAGGTCACG GAACTCTTTC TGATCCCACC ACATGCGGCC TTGTGTGGCA    360

CAGTACTTGG CTTCCACAGA AGCTTGGCAA CCATCTATGT GGAATCCTTT GTAAGATGCA    420

ACGAAAGGTG CATTGGCCCA ATTGGTCTTC TCTAAACCGC CTCTCGTGGC CCAATCATCC    480

GCGTTCCAAA GGCTTGAGTA AAGCTTCATT GGTTGGTTGA ATGGGAAACG TACTCCTAGA    540

TCCTTAGCAT TCTTGAACGT TCGGATTGGT ATGTTGTCAA CAAAGAATAC GATCTGGTAC    600

ATGTTCCAAA GGATTGAGTA AGTGTGATAA GCCTTAGAAG GATCAAACCA GAGATAGATT    660

CGTTGTTCTC TGTTTCCCTT TCCTCCTGTG AATACATTTG TCTGTAATAT AGCTGGTTGT    720

CCTGTTCTGT TTCCAAGGAA CTCAAAGTCT ATCTCGTCAT GCTCATTGTT GGTAGATGAT    780

AGATAGAAAG CTGTGACAAC TCCGGCTGTG TCACCAGCTG GAAGCTTTAT GTGCATACTA    840

AAATGTCCAA ACAAATATGA CCCCTTTGAT TGAAATCCTG TGCCAGTGTA TTTGTCGAGG    900

ATAAGCTGAA GTTCGGAACC GCCATTGAAC TGTTTCTGGT GGTCAAAAGC CCAAGTTGGG    960

ACGTAGTTAC GACCAAATGG TACATCAATG GCCTTGCGTG GAGGAATAGC CATTACCATT   1020

GTTGAAGAAA CCATTAGAAA GAGAGCCATG AGAGCCCATG GAGATGAAGA AACAGTCATG   1080

GGTGGGTTTA TTATATGATG ATGATAGTCT CCAAGCTATC CTGGATCTGA CAGCTGACTG   1140

GACTCCAGCA GAGAGAGAGA TGCTAAGGAA CAAAGTCCCA GTTACTGGCT TAAAGACTCC   1200

TTTTAGGGAT GGTTTGTTAA AGCATGTCGC TGAAGATGTC CCTGAAACTC GCAAAGGATG   1260

GTTTAGAGCG CAGAGGCTAC AAGGAAGCGG TTTCTTGAAC GCAGTCGATG AAGTGGTCAT   1320
```

(2) INFORMATION FOR SEQ ID NO:4:

(i) SEQUENCE CHARACTERISTICS:
       (A) LENGTH: 1128 bases
       (B) TYPE: nucleic acid
       (C) STRANDEDNESS: single
       (D) TOPOLOGY: linear (ii) MOLECULE TYPE: cDNA to mRNA (iii) HYPOTHETICAL: no (iv) ANTI-SENSE: yes (vi) ORIGINAL SOURCE:
       (A) ORGANISM: Lycopersicon esculentum (xi) SEQUENCE DESCRIPTION: SEQ ID NO:4:

```
GAGACATGAA AGGCCTGGCA TGAGATACAT AATATCCTCA TGACTCCACC AATAATGATA     60

CACTCAAAAA GAATTAGGGA AATACAGCTC AATTAAAAGC ACTTTGTTTT AAGGATCATT    120

AAAATACTCA CACATAAAGC ATATTAAGTT TTTTTTCTTC ATAAAGTCCC TCTTAATTTT    180

GATTATGATT TTAAATATCT CTGTCCTTAG TGCACTCTGG TGGTGGAACA GGGTACCTCG    240

CTTTATCAGT GCAATAGTTA TAAACAGTGT ATTTTTGACG AACCCAACGA AGTCTCCTAT    300
```

```
ACTGTAATGC ATCTAAATCT TGGAAGGCCT TTTGATCCCA CCATTTCATG CCTTTAGTGT      360

TACAAACTTG GACTTCTTGT GGCGTGGCAG CTTCACATCC ATCCACGTGG AACGATGTGT      420

ATGACGCGGT GAATGGGGCG TTGGCCCAAT TGGTTTTCTC AAGCCCACCT CTTGTGGCCC      480

AATCATCTGC GTCCCATAGA CTCGAGTATA TCTTCATGGG CTGATTGAAT GGAAATTTCA      540

CACCAAGATC TTTCGAATTT TTGAATGCTC TAATTGGAAC GTCGTCCACA AGATCACAA       600

TGAGGTATGT ATTCCAAAGA ACAGAATAAG AATGGTAGCC CTTGGTTGGA TCAAACCAAA      660

GATATATTCT CTGTTCTCTG TTTCCTTTTC CTCCTGTGAA TACATTTGTC TGCAATATGT      720

ATGGCTGCCC AGTTCTGTTC CCCAAAAATT CAAAATCTAT CTCATCGTGC TCTGCATTAT      780

TCGATGACAG GTAAAATGCA GTGACAACAC CAGCTGAGTC TCCACCAACA AGCCTCATTT      840

TCATACTGAA ATGCCCAAAC AGATATGATT TCTTTGACTG AAATCCAGCT CCTGAAGATC      900

TGTCGAGAAT AAGATCAGTA GTGGTACCAC CATTGAGGAA CTTAATATGG TGACTAGCCC      960

AACTTGGCTC ATAGTTTTTC CAAAAGGGCA CATCTACTGG CCTTCTAGGA TACCCACAAA     1020

ATACAACAAG TGACAAATTA ATCAAAACAA TACTAAATAA AACTCCTTTT ATGATACCCA     1080

TGGTGAGAAA AACAAATCCA ATCAGAGACC AGTGTTTGTG TATTTTTC                  1128

(2) INFORMATION FOR SEQ ID NO:5:

(i) SEQUENCE CHARACTERISTICS:
        (A) LENGTH: 872 bases
        (B) TYPE: nucleic acid
        (C) STRANDEDNESS: single
        (D) TOPOLOGY: linear (ii) MOLECULE TYPE: cDNA to mRNA (iii) HYPOTHETICAL: no (iv) ANTI-SENSE: yes (vi) ORIGINAL SOURCE:
         (A) ORGANISM: Triticum aestivum (xi) SEQUENCE DESCRIPTION: SEQ ID NO:5:

AGCGGTCGTG GTCGGTGCAG TAGTTGTAGA TGGTGTGCTC CTTCCTGACC CAGGCGAGGC       60

GGCGGTACTG CGCGGCGTCC AGGTCCTGGA ACTCGGGCTG GTCCCACCAG CGGGCGCCCT      120

GGGTGGCGCA GAACTTGGCC TCCGCGGACG CCTCGCAGCC GTCGACGTGG AAGCCCCGGT      180

AGGAGGCGAC GAAGGGCGCC TTGGACCAGT CCGTCTTCTC CCGCCCGCCC CGGGTCGCCC      240

AGTCGTCCGC GTTCCACAGG CTGGAGTAGA GCTTCATGGG CTGGTCGAAC GGGTACCGCA      300

CCCCGAGGTC CTTGCTGTTC TTGAACACCC GGATCGGCGT GTCGTCCACG AAGAACGCGA      360

TCATGTAGAG GTTCCAGAGG ACGGAGTAGG AGTGGTAGTC CTTGGTTGGG TCGAACCAGA      420

GGTAGATCCT CTGCTCCCGG TCGCCCTTGC CGCCGGAGAA CACGTTGGTC TGCAGGATGT      480

ACGGCTGCCC CGTCCTGTTC CCCAAGAACT CGAAGTCGAT CTCGTCGTGC TCCGAGTTCT      540

GTGACGACAG GTAGAAGGCG GTGACGGTGC CGGCGGAGTC GCCGCCGACG AGCTTGATGT      600

GCATGCTGAA GTGGCCGAAG AGGTAGGAGC CCCGGGTCTG GAAGCCCGTG CCGGTGGTCT      660

TGTCCAGGGA CAGCTGCACC TCCCGCCCGC CGTTCACGTA GTGGATGTGG TCCTGCGCCC      720

ACGTCGGCAC GTAGTTCTTG TCGAACGGCA CGTCCACCGG CTTCCGGGGC GCTGCCGCCA      780

CGCCGCGTAG CAGCACCGCC GCCACCACGG CGAGGAGGGC CCCCGCGGTC GCCTTCATTT      840

CGCCGGCCGG CCTCTCTTCC TCCTTCTCTG TT                                   872
```

(2) INFORMATION FOR SEQ ID NO:6:

(i) SEQUENCE CHARACTERISTICS:
        (A) LENGTH: 1133 bases
        (B) TYPE: nucleic acid
        (C) STRANDEDNESS: single
        (D) TOPOLOGY: linear (ii) MOLECULE TYPE: mRNA (iii) HYPOTHETICAL: no (iv) ANTI-SENSE: yes (vi) ORIGINAL SOURCE:
        (A) ORGANISM: Vigna angularis (xi) SEQUENCE DESCRIPTION: SEQ ID NO:6:

```
UUUUUUUUUU AACCAGUAUA AACUAGUAGU AUUACUAGUA UAUUGAUUCA GAGUGAAACA      60
GAAUUACAGA UACAAAUUAA GGCACAGAGC CAUAUCUGGU ACAUAGCCAA ACAGUAGCAG     120
CAAUAAAUGA UGAUAUGAUU AUCAACAAUA CAGGAAGCAA UAGCAAGCUC AAAUGAAAUC     180
UGUAUCAGCA CUUAGGUGGG AACUUUAUGG CAGUGUGAUA UUGAAAAUAA UGAGGCCUUA     240
AAGUAUAGGU UAAAAUGAUU AAAUGUCACG GUCUCUGGUG CACUCUGGAG GGACUUGAGA     300
GUAGCGUUUG CGAUCAGUGU AGUAGUUGUA GAUGGUGUAU UUGUUGCGUA CCCAAGCCAG     360
UUUUUGCCAC UGAGCAGCAU CAAGGUCACG AAACUCUGGU UGAUCCCACC ACCUCUUGCC     420
UUGUGUGUCA CAGAACUUGG CAUUCACUGA GGCCUCACAC CCAUCAAUGU GGAAGCCCUU     480
GUAAGAGGCU AUGAAGGGGG CUUUGGACCA AUCUGUUUUC UCCAAACCAC CCCUUGUAGC     540
CCAGUCAUCU GCAUUCCACA AACUGUUGUA UAUUUCAUU GGUUGAUUGA AGGGGAACUU      600
CACUCCCAAG UCAUUGCUGU UCUUGAACAC CCUUAUUGGG UAGUCAUCCA CAUAGAAUAC     660
AAUCUGGUAC AUGUUCCAUA GCACUGAAUA UCUGUGGUAU UGAGUCGUAG GGUCAAACCA     720
GAGGUAGAUU CUCUGCUCUC UGUCACCUUU GCCUCCGGUG AACACAUUUG UUUGUAAAAU     780
GUAUGGUUGC CCAGUUCUGU UUCCCAAGAA CUCGAAGUCU AUUUCAUCAU GUUCUGCGUU     840
UGGGACGAU AAAUAGAAAG CAGUGACUGU GCCAGCUGAA UCACCAGGAA CCAAUUUUAU      900
GUACAUGCUG AAGUGACCAA ACAAGUAUGA CCCUUUGGAC UGGAAUCCAG UACCAGUGUA     960
CUUAUCGAGA UGAAGCUGAA UCUCAGAACC UCCAUUGAGA UAUUUGAUAU GAUCAAAGGC    1020
CCAAGUAGGC ACAUAGUUUC UGCCAAAUGG UACAUCAAUU GGAGUUCUUG GGUUGGCAGC    1080
GAAAGAAGCA GAAGCCAGUG AUAACAGAAU CAGACAAGUC CACAAAGAAG AAC          1133
```

(2) INFORMATION FOR SEQ ID NO:7:

(i) SEQUENCE CHARACTERISTICS:
        (A) LENGTH: 957 bases
        (B) TYPE: nucleic acid
        (C) STRANDEDNESS: single
        (D) TOPOLOGY: linear (ii) MOLECULE TYPE: mRNA (iii) HYPOTHETICAL: no (iv) ANTI-SENSE: yes (vi) ORIGINAL SOURCE:
        (A) ORGANISM: Glycine max (xi) SEQUENCE DESCRIPTION: SEQ ID NO:7:

```
UGAAAAGAGA AGCAACAAUA AUAAAGUGAA UGAGAAAUUU AAAUAUCACG GACUAAAAUA      60
```

-continued

```
UCUAUUCACU CGAAAUUUAA AUGUCACGGU CUCUUUUGCA CUCAGGAGGA GAGAUAUGAG      120

GAUAGCGUUU AGUGUCAGUG CAGUAGUUGU AGAUGGUGUA UUUCUGGCGC ACCCAUCUGA      180

GCCUACGCCA CUGGGCGGCG UCAAGGUCAC GGAACUCAGG CUGGUCCCAC CACCUCUUGC      240

CCUGCGUGUC GCAGAACUUG GCGUUCACCG AAGCCUCGCA CCCGUCGAUG UGAAACCCCU      300

UGUACGCUGC UAUGAAGGGU GCUUUCGACC AAUCCGUUUU CUCCAAACCA CCCCUCGUUG      360

CCCAGUCAUC AGCGUUCCAC AAACUGUUGU AGAUCUUCAU UGGCUGGUCG AAUGGGAAUU      420

UCACUCCCAA GUCCUUGCUG UUCUUGAACA CCCUGAUUGG CACCUCGUCC ACAAAGAACA      480

CAAUCUGAUA CAAGUUCCAG AGAAUGGAGU AUCUGUGGUA UUCUUUCGUG GGAUCAAACC      540

AGAGAUAGAU UCUUUGCUCU CUAUCACCCU UGCCUCCGGU GAACACAUUU GUUUGCAGAA      600

UGUAAGGUUG UCCUGUUCUG UUCCCCAAGA ACUCAAAGUC UAUCUCAUCA UGCUCCGCGU      660

UUUGGGAAGA UAAAUAGAAA GCAGUGACUG UGCCAGCAGA AUCUCCAGGA ACCAUCUUUA      720

UGUACAUGCU GAAGUGACCA AACAAGUAAG ACCCUUUGGA CUGGAAGCCA GUACCAGUGU      780

ACUUGUCAAG AUGAAGCUGA AUGUCAGAAC CACCAUUGAA AUAUUUGAUG UGAUCAAAGG      840

CCCAUGUGGG CACGUAGUUU CGGCCAAAUU GUACAUCCAC UGGCCUGCGU GGGUUGGCAC      900

AGAGUGCUGC AGAGGCCAGU GAUGCCAAAA UCACACACAC CGUCCACACA GAAAAAA       957
```

(2) INFORMATION FOR SEQ ID NO:8:

(i) SEQUENCE CHARACTERISTICS:
        (A) LENGTH: 1320 bases
        (B) TYPE: nucleic acid
        (C) STRANDEDNESS: single
        (D) TOPOLOGY: linear (ii) MOLECULE TYPE: mRNA (iii) HYPOTHETICAL: no (iv) ANTI-SENSE: yes (vi) ORIGINAL SOURCE:
        (A) ORGANISM: Arabidopsis thaliana (xi) SEQUENCE DESCRIPTION: SEQ ID NO:8:

```
UUUUUUUUUU UUUUUUAUGA AAAUACAUAG CUAAUCAAUA CAUAUAUGAA UUAUAACAUG       60

UAAUUUUAGG CCCAAAUAUA GCAUAAACAU CAUGGGCCAA CAAACAAUAC AUAUAUCAAU      120

CUCUUGAACA AGCAUAAUUC AAAUAAUAAU GAUAGCAUAA AUUCAUUAAA ACCCUCAAGA      180

GUAGUAACUU AUGCGUCUCU GUCCCUUUUA CAUUCAGCUG GCAUAACCGG GAACCUAGUC      240

CGGUCGGUAC AGUAGUUGUA GAUGGUCCAC UUCAUACGAA CCCAUUUGAG ACGACGCCAU      300

UGUUCAGCGU CAAGGUCACG GAACUCUUUC UGAUCCCACC ACAUGCGGCC UUGUGUGGCA      360

CAGUACUUGG CUUCCACAGA AGCUUGGCAA CCAUCUAUGU GGAAUCCUUU GUAAGAUGCA      420

ACGAAAGGUG CAUUGGCCCA AUUGGUCUUC UCUAAACCGC CUCUCGUGGC CCAAUCAUCC      480

GCGUUCCAAA GGCUUGAGUA AAGCUUCAUU GGUUGGUUGA AUGGGAAACG UACUCCUAGA      540

UCCUUAGCAU UCUUGAACGU UCGGAUUGGU AUGUUGUCAA CAAAGAAUAC GAUCUGGUAC      600

AUGUUCCAAA GGAUUGAGUA AGUGUGAUAA GCCUUGAAAG GAUCAAACCA GAGAUAGAUU      660

CGUUGUUCUC UGUUUCCCUU UCCUCCUGUG AAUACAUUUG UCUGUAAUAU AGCUGGUUGU      720

CCUGUUCUGU UUCCAAGGAA CUCAAAGUCU AUCUCGUCAU GCUCAUUGUU GGUAGAUGAU      780

AGAUAGAAAG CUGUGACAAC UCCGGCUGUG UCACCAGCUG GAAGCUUUAU GUGCAUACUA      840

AAAUGUCCAA ACAAAUAUGA CCCCUUUGAU UGAAAUCCUG UGCCAGUGUA UUUGUCGAGG      900
```

```
AUAAGCUGAA GUUCGGAACC GCCAUUGAAC UGUUUCUGGU GGUCAAAAGU CCAAGUUGGG      960

ACGUAGUUAC GACCAAAUGG UACAUCAAUG GCCUUGCGUG GAGGAAUAGC CAUUACCAUU     1020

GUUGAAGAAA CCAUUAGAAA GAGAGCCAUG AGAGCCCAUG GAGAUGAAGA AACAGUCAUG     1080

GGUGGGUUUA UUAUAUGAUG AUGAUAGUCU CCAAGCUAUC CUGGAUCUGA CAGCUGACUG     1140

GACUCCAGCA GAGAGAGAGA UGCUAAGGAA CAAAGUCCCA GUUACUGGCU UAAAGACUCC     1200

UUUUAGGGAU GGUUUGUUAA AGCAUGUCGC UGAAGAUGUC CCUGAAACUC GCAAAGGAUG     1260

GUUUAGAGCG CAGAGGCUAC AAGGAAGCGG UUUCUUGAAC GCAGUCGAUG AAGUGGUCAU     1320
```

(2) INFORMATION FOR SEQ ID NO:9:

(i) SEQUENCE CHARACTERISTICS:
        (A) LENGTH: 1128 bases
        (B) TYPE: nucleic acid
        (C) STRANDEDNESS: single
        (D) TOPOLOGY: linear (ii) MOLECULE TYPE: mRNA (iii) HYPOTHETICAL: no (iv) ANTI-SENSE: yes (vi) ORIGINAL SOURCE:
        (A) ORGANISM: Lycopersicon esulentum (xi) SEQUENCE DESCRIPTION: SEQ ID NO:9:

```
GAGACAUGAA AGGCCUGGCA UGAGAUACAU AAUAUCCUCA UGACUCCACC AAUAAUGAUA       60

CACUCAAAAA GAAUUAGGGA AAUACAGCUC AAUUAAAAGC ACUUUGUUUU AAGGAUCAUU      120

AAAAUACUCA CACAUAAAGU AUAUUAAGUU UUUUUUCUUC AUAAAGUCCC UCUUAAUUUU      180

GAUUAUGAUU UUAAAUAUCU CUGUCCUUAG UGCACUCUGG UGGUGGAACA GGGUACCUGG      240

CUUUAUCAGU GCAAUAGUUA UAAACAGUGU AUUUUUGACG AACCCAACGA AGUCUCCUAU      300

ACUGUAAUGC AUCUAAAUCU UGGAAGGCCU UUUGAUCCCA CCAUUUCAUG CCUUUAGUGU      360

UACAAACUUG GACUUCUUGU GGCGUGGCAG CUUCACAUCC AUCCACGUGG AACGAUGUGU      420

AUGACGCGGU GAAUGGGGCG UUGGCCCAAU UGGUUUUCUC AAGCCCACCU CUUGUGGCCC      480

AAUCAUCUGC GUCCCAUAGA CUCGAGUAUA UCUUCAUGGG CUGAUUGAAU GGAAAUUUCA      540

CACCAAGAUC UUUCGAAUUU UUGAAUGCUC UAAUUGGAAC GUCGUCCACA AGAUCACAA      600

UGAGGUAUGU AUUCCAAAGA ACAGAAUAAG AAUGGUAGCC CUUGGUUGGA UCAAACCAAA      660

GAUAUAUUCU CUGUUCUCUG UUUCCUUUUC CUCCUGUGAA UACAUUUGUC UGCAAUAUGU      720

AUGGCUGCCC AGUUCUGUUC CCCAAAAAUU CAAAAUCUAU CUCAUCGUGC UCUGCAUUAU      780

UCGAUGACAG GUAAAAUGCA GUGACAACAC CAGCUGAGUC UCCACCAACA AGCCUCAUUU      840

UCAUACUGAA AUGCCCAAAC AGAUAUGAUU UCUUUGACUG AAAUCCAGCU CCUGAAGAUC      900

UGUCGAGAAU AAGAUCAGUA GUGGUACCAC CAUUGAGGAA CUUAAUAUGG UGACUAGCCC      960

AACUUGGCUC AUACUUUUUC CAAAAGGGCA CAUCUACUGG CCUUCUAGGA UACCCACAAA     1020

AUACAACAAG UGACAAAUUA AUCAAAACAA UACUAAAUAA AACUCCUUUU AUGAUACCCA     1080

UGGUGAGAAA AACAAAUCCA AUCAGAGACC AGUGUUUGUG UAUUUUUC                 1128
```

(2) INFORMATION FOR SEQ ID NO:10:

(i) SEQUENCE CHARACTERISTICS:
        (A) LENGTH: 872 bases
        (B) TYPE: nucleic acid (C) STRANDEDNESS: single
          (D) TOPOLOGY: linear (ii) MOLECULE TYPE: mRNA (iii) HYPOTHETICAL: no (iv) ANTI-SENSE: yes (vi) ORIGINAL SOURCE:
          (A) ORGANISM: Triticum aestivum (xi) SEQUENCE DESCRIPTION: SEQ ID NO:10:

```
AGCGGUCGUG GUCGGUGCAG UAGUUGUAGA UGGUGUGCUC CUUCCUGACC CAGGCGAGGC      60

GGCGGUACUG CGCGGCGUCC AGGUCCUGGA ACUCGGGCUG GUCCACCAG CGGGCGCCCU      120

GGGUGGCGCA GAACUUGGCC UCCGCGGACG CCUCGCAGCC GUCGACGUGG AAGCCCCGGU     180

AGGAGGCGAC GAAGGGCGCC UUGGACCAGU CCGUCUUCUC CCGCCCGCCC CGGGUCGCCC    240

AGUCGUCCGC GUUCCACAGG CUGGAGUAGA GCUUCAUGGG CUGGUCGAAC GGGUACCGCA     300

CCCCGAGGUC CUUGCUGUUC UUGAACACCC GGAUCGGCGU GUCGUCCACG AAGAACGCGA     360

UCAUGUAGAG GUUCCAGAGG ACGGAGUAGG AGUGGUAGUC CUUGGUUGGG UCGAACCAGA     420

GGUAGAUCCU CUGCUCCCGG UCGCCCUUGC CGCCGGAGAA CACGUUGGUC UGCAGGAUGU     480

ACGGCUGCCC CGUCCUGUUC CCCAAGAACU CGAAGUCGAU CUCGUCGUGC UCCGAGUUCU     540

GUGACGACAG GUAGAAGGCG GUGACGGUGC CGGCGGAGUC GCCGCCGACG AGCUUGAUGU     600

GCAUGCUGAA GUGGCCGAAG AGGUAGGAGC CCCGGGUCUG GAAGCCCGUG CCGGUGGUCU     660

UGUCCAGGGA GAGCUGCACC UCCCGCCCGC CGUUCACGUA GUGGAUGUGG UCCUGCGCCC     720

ACGUCGGCAC GUAGUUCUUG UCGAACGGCA CGUCCACCGG CUUCCGGGGC GCUGCCGCCA     780

CGCCGCGUAG CAGCACCGCC GCCACCACGG CGAGGAGGGC CCCCGCGGUC GCCUUCAUUU     840

CGCCGGCCGG CCUCUCUUCC UCCUUCUCUG UU                                  872
```

(2) INFORMATION FOR SEQ ID NO:11:

(i) SEQUENCE CHARACTERISTICS:
          (A) LENGTH: 30 amino acids
          (B) TYPE: amino acid
          (C) STRANDEDNESS: single
          (D) TOPOLOGY: linear (ii) MOLECULE TYPE: peptide (v) FRAGMENT TYPE: N-terminal fragment (vi) ORIGINAL SOURCE:
          (A) ORGANISM: Vigna angularis (xi) SEQUENCE DESCRIPTION: SEQ ID NO:11:

```
Ala Asn Pro Arg Thr Pro Ile Asp Val Pro Phe Gly Arg Asn Tyr
 1               5                  10                  15

Val Pro Thr Trp Ala Phe Asp His Ile Lys Tyr Leu Asn Gln Gly
```

(2) INFORMATION FOR SEQ ID NO:12:

(i) SEQUENCE CHARACTERISTICS:
          (A) LENGTH: 29 bases
          (B) TYPE: nucleic acid
          (C) STRANDEDNESS: single
          (D) TOPOLOGY: linear (ii) MOLECULE TYPE: other nucleic acid (xi) SEQUENCE DESCRIPTION: SEQ ID NO:12:

```
ATCGAYGTGC CGTTYGGGMG NAAYTAYGT                                       29
```

(2) INFORMATION FOR SEQ ID NO:13:

(i) SEQUENCE CHARACTERISTICS:
        (A) LENGTH: 29 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:13:

```
CCGACGTGGG CGTTYGAYCA YATHAARTA                                       29
```

(2) INFORMATION FOR SEQ ID NO:14:

(i) SEQUENCE CHARACTERISTICS:
        (A) LENGTH: 37 bases
        (B) TYPE: nucleic acid
        (C) STRANDEDNESS: single
        (D) TOPOLOGY: linear (ii) MOLECULE TYPE: other nucleic acid (xi) SEQUENCE DESCRIPTION: SEQ ID NO:14:

```
GTTTTCCCAG TCACGACTTT TTTTTTTTTT TTTTTTT                              37
```

(2) INFORMATION FOR SEQ ID NO:15:

(i) SEQUENCE CHARACTERISTICS:
        (A) LENGTH: 1133 bases
        (B) TYPE: nucleic acid
        (C) STRANDEDNESS: double
        (D) TOPOLOGY: linear (ii) MOLECULE TYPE: cDNA to mRNA (iii) HYPOTHETICAL: no (iv) ANTI-SENSE: no (vi) ORIGINAL SOURCE:
        (A) ORGANISM: Vigna angularis (xi) SEQUENCE DESCRIPTION: SEQ ID NO:15:

```
GTTCTTCTTT GTGGACTTGT CTGATTCTGT TATCACTGGC TTCTGCTTCT TTCGCTGCCA      60

ACCCAAGAAC TCCAATTGAT GTACCATTTG GCAGAAACTA TGTGCCTACT TGGGCCTTTG     120

ATCATATCAA ATATCTCAAT GGAGGTTCTG AGATTCAGCT TCATCTCGAT AAGTACACTG     180

GTACTGGATT CCAGTCCAAA GGGTCATACT TGTTTGGTCA CTTCAGCATG TACATAAAAT     240

TGGTTCCTGG TGATTCAGCT GGCACAGTCA CTGCTTTCTA TTTATCGTCC ACAAACGCAG     300

AACATGATGA AATAGACTTC GAGTTCTTGG GAAACAGAAC TGGGCAACCA TACATTTTAC     360

AAACAAATGT GTTCACCGGA GGCAAAGGTG ACAGAGAGCA GAGAATCTAC CTCTGGTTTG     420

ACCCTACGAC TCAATACCAC AGATATTCAG TGCTATGGAA CATGTACCAG ATTGTATTCT     480

ATGTGGATGA CTACCCAATA AGGGTGTTCA AGAACAGCAA TGACTTGGGA GTGAAGTTCC     540

CCTTCAATCA ACCAATGAAA ATATACAACA GTTTGTGGAA TGCAGATGAC TGGGCTACAA     600

GGGGTGGTTT GGAGAAAACA GATTGGTCCA AAGCCCCCTT CATAGCCTCT TACAAGGGCT     660

TCCACATTGA TGGGTGTGAG GCCTCAGTGA ATGCCAAGTT CTGTGACACA CAAGGCAAGA     720

GGTGGTGGGA TCAACCAGAG TTTCGTGACC TTGATGCTGC TCAGTGGCAA AAACTGGCTT     780
```

```
GGGTACGCAA CAAATACACC ATCTACAACT ACTGCACTGA TCGCAAACGC TACTCTCAAG      840

TCCCTCCAGA GTGCACCAGA GACCGTGACA TTTAATCATT TTAACCTATA CTTTAAGGCC      900

TCATTATTTT CAATATCACA CTCCCATAAA GTTCCCACCT AAGTGCTGAT ACAGATTTCA      960

TTTGAGCTTG CTATTGCTTC CTGTATTGTT GATAATCATA TCATCATTTA TTGCTGCTAC     1020

TGTTTGGCTA TGTACCAGAT ATGGCTCTGT GCCTTAATTT GTATCTGTAA TTCTGTTTCA     1080

CTCTGAATCA ATATACTAGT AATACTACTA GTTTATACTG GTTAAAAAAA AAA            1133

(2) INFORMATION FOR SEQ ID NO:16:

(i) SEQUENCE CHARACTERISTICS:
        (A) LENGTH: 957 bases
        (B) TYPE: nucleic acid
        (C) STRANDEDNESS: double
        (D) TOPOLOGY: linear (ii) MOLECULE TYPE: cDNA to mRNA (iii) HYPOTHETICAL: no (iv) ANTI-SENSE: no (vi) ORIGINAL SOURCE:
        (A) ORGANISM: Glycine max (xi) SEQUENCE DESCRIPTION: SEQ ID NO:16:

TTTTTTCTGT GTGGACGGTG TGTGTGATTT TGGCATCACT GGCCTCTGCA GCACTCTGTG       60

CCAACCCACG CAGGCCAGTG GATGTACAAT TTGGCCGAAA CTACGTGCCC ACATGGGCCT      120

TTGATCACAT CAAATATTTC AATGGTGGTT CTGACATTCA GCTTCATCTT GACAAGTACA      180

CTGGTACTGG CTTCCAGTCC AAAGGGTCTT ACTTGTTTGG TCACTTCAGC ATGTACATAA      240

AGATGGTTCC TGGAGATTCT GCTGGCACAG TCACTGCTTT CTATTTATCT TCCCAAAACG      300

CGGAGCATGA TGAGATAGAC TTTGAGTTCT TGGGGAACAA AACAGGACAA CCTTACATTC      360

TGCAAACAAA TGTGTTCACC GGAGGCAAGG GTGATAGAGA GCAAAGAATC TATCTCTGGT      420

TTGATCCCAC GAAAGAATAC CACAGATACT CCATTCTCTG GAACTTGTAT CAGATTGTGT      480

TCTTTGTGGA CGAGGTGCCA ATCAGGGTGT TCAAGAACAG CAAGGACTTG GGAGTGAAAT      540

TCCCATTCGA CCAGCCAATG AAGATCTACA ACAGTTTGTG GAACGCTGAT GACTGGGCAA      600

CGAGGGGTGG TTTGGAGAAA ACGGATTGGT CGAAAGCACC CTTCATAGCA GCGTACAAGG      660

GGTTTCACAT CGACGGGTGC GAGGCTTCGG TGAACGCCAA GTTCTGCGAC ACGCAGGGCA      720

AGAGGTGGTG GGACCAGCCT GAGTTCCGTG ACCTTGACGC CGCCCAGTGG CGTAGGCTCA      780

GATGGGTGCG CCAGAAATAC ACCATCTACA ACTACTGCAC TGCACTAAA CGCTATCCTC       840

ATATCTCTCC TCCTGAGTGC AAAAGAGACC GTGACATTTA AATTTCGAGT GAATAGATAT      900

TTTAGTCCGT GATATTTAAA TTTCTCATTC ACTTTATTAT TGTTGCTTCT CTTTTCA         957

(2) INFORMATION FOR SEQ ID NO:17:

(i) SEQUENCE CHARACTERISTICS:
        (A) LENGTH: 1320 bases
        (B) TYPE: nucleic acid
        (C) STRANDEDNESS: double
        (D) TOPOLOGY: linear (ii) MOLECULE TYPE: cDNA to mRNA (iii) HYPOTHETICAL: no (iv) ANTI-SENSE: no
```

(vi) ORIGINAL SOURCE:
    (A) ORGANISM: Arabidopsis thaliana (xi) SEQUENCE DESCRIPTION: SEQ ID NO:17:

```
ATGACCACTT CATCGACTGC GTTCAAGAAA CCGCTTCCTT GTAGCCTCTG CGCTCTAAAC      60

CATCCTTTGC GAGTTTCAGG GACATCTTCA GCGACATGCT TTAACAAACC ATCCCTAAAA     120

GGAGTCTTTA AGCCAGTAAC TGGGACTTTG TTCCTTAGCA TCTCTCTCTC TGCTGGAGTC     180

CAGTCAGCTG TCAGATCCAG GATAGCTTGG AGACTATCAT CATCATATAA TAAACCCACC     240

CATGACTGTT TCTTCATCTC CATGGGCTCT CATGGCTCTC TTTCTAATGG TTTCTTCAAC     300

AATGGTAATG GCTATTCCTC CACGCAAGGC CATTGATGTA CCATTTGGTC GTAACTACGT     360

CCCAACTTGG GCTTTTGACC ACCAGAAACA GTTCAATGGC GGTTCCGAAC TTCAGCTTAT     420

CCTCGACAAA TACACTGGCA CAGGATTTCA ATCAAAGGGG TCATATTTGT TTGGACATTT     480

TAGTATGCAC ATAAAGCTTC CAGCTGGTGA CACAGCCGGA GTTGTCACAG CTTTCTATCT     540

ATCATCTACC AACAATGAGC ATGACGAGAT AGACTTTGAG TTCCTTGGAA ACAGAACAGG     600

ACAACCAGCT ATATTACAGA CAAATGTATT CACAGGAGGA AAGGGAAACA GAGAACAACG     660

AATCTATCTC TGGTTTGATC CTTCTAAGGC TTATCACACT TACTCAATCC TTTGGAACAT     720

GTACCAGATC GTATTCTTTG TTGACAACAT ACCAATCCGA ACGTTCAAGA ATGCTAAGGA     780

TCTAGGAGTA CGTTTCCCAT TCAACCAACC AATGAAGCTT TACTCAAGCC TTTGGAACGC     840

GGATGATTGG GCCACGAGAG GCGGTTTAGA AAGACCAAT TGGGCCAATG CACCTTTCGT     900

TGCATCTTAC AAAGGATTCC ACATAGATGG TTGCCAAGCT TCTGTGGAAG CCAAGTACTG     960

TGCCACACAA GGCCGCATGT GGTGGGATCA GAAAGAGTTC CGTGACCTTG ACGCTGAACA    1020

ATGGCGTCGT CTCAAATGGG TTCGTATGAA GTGGACCATC TACAACTACT GTACCGACCG    1080

GACTAGGTTC CCGGTTATGC CAGCTGAATG TAAAAGGGAC AGAGACGCAT AAGTTACTAC    1140

TCTTGAGGGT TTTAATGAAT TTATGCTATC ATTATTATTT GAATTATGCT TGTTCAAGAG    1200

ATTGATATAT GTATTGTTTG TTGGCCCATG ATGTTTATGC TATATTTGGG CCTAAAATTA    1260

CATGTTATAA TTCATATATG TATTGATTAG CTATGTATTT TCATAAAAAA AAAAAAAAAA    1320
```

(2) INFORMATION FOR SEQ ID NO:18:

(i) SEQUENCE CHARACTERISTICS:
        (A) LENGTH: 1128 bases
        (B) TYPE: nucleic acid
        (C) STRANDEDNESS: double
        (D) TOPOLOGY: linear (ii) MOLECULE TYPE: cDNA to mRNA (iii) HYPOTHETICAL: no (iv) ANTI-SENSE: no (vi) ORIGINAL SOURCE:
        (A) ORGANISM: Lycopersicon esculentum (xi) SEQUENCE DESCRIPTION: SEQ ID NO:18:

```
GAAAAATACA CAAACACTGG TCTCTGATTG GATTTGTTTT TCTCACCATG GGTATCATAA      60

AAGGAGTTTT ATTTAGTATT GTTTTGATTA ATTTGTCACT TGTTGTATTT TGTGGGTATC     120

CTAGAAGGCC AGTAGATGTG CCCTTTTGGA AAAACTATGA GCCAAGTTGG GCTAGTCACC     180

ATATTAAGTT CCTCAATGGT GGTACCACTA CTGATCTTAT TCTCGACAGA TCTTCAGGAG     240

CTGGATTTCA GTCAAAGAAA TCATATCTGT TTGGGCATTT CAGTATGAAA ATGAGGCTTG     300
```

-continued

```
TTGGTGGAGA CTCAGCTGGT GTTGTCACTG CATTTTACCT GTCATCGAAT AATGCAGAGC      360

ACGATGAGAT AGATTTTGAA TTTTTGGGGA ACAGAACTGG GCAGCCATAC ATATTGCAGA      420

CAAATGTATT CACAGGAGGA AAAGGAAACA GAGAACAGAG AATATATCTT TGGTTTGATC      480

CAACCAAGGG CTACCATTCT TATTCTGTTC TTTGGAATAC ATACCTCATT GTGATCTTTG      540

TGGACGACGT TCCAATTAGA GCATTCAAAA ATTCGAAAGA TCTTGGTGTG AAATTTCCAT      600

TCAATCAGCC CATGAAGATA TACTCGAGTC TATGGGACGC AGATGATTGG GCCACAAGAG      660

GTGGGCTTGA GAAAACCAAT TGGGCCAACG CCCCATTCAC CGCGTCATAC ACATCGTTCC      720

ACGTGGATGG ATGTGAAGCT GCCACGCCAC AAGAAGTCCA AGTTTGTAAC ACTAAAGGCA      780

TGAAATGGTG GGATCAAAAG GCCTTCCAAG ATTTAGATGC ATTACAGTAT AGGAGACTTC      840

GTTGGGTTCG TCAAAAATAC ACTGTTTATA ACTATTGCAC TGATAAAGCG AGGTACCCTG      900

TTCCACCACC AGAGTGCACT AAGGACAGAG ATATTTAAAA TCATAATCAA AATTAAGAGG      960

GACTTTATGA AGAAAAAAAA CTTAATATGC TTTATGTGTG AGTATTTTAA TGATCCTTAA     1020

AACAAAGTGC TTTTAATTGA GCTGTATTTC CCTAATTCTT TTTGAGTGTA TCATTATTGG     1080

TGGAGTCATG AGGATATTAT GTATCTCATG CCAGGCCTTT CATGTCTC                 1128
```

(2) INFORMATION FOR SEQ ID NO:19:

(i) SEQUENCE CHARACTERISTICS:
        (A) LENGTH: 872 bases
        (B) TYPE: nucleic acid
        (C) STRANDEDNESS: double
        (D) TOPOLOGY: linear (ii) MOLECULE TYPE: cDNA to mRNA (iii) HYPOTHETICAL: no (iv) ANTI-SENSE: no (vi) ORIGINAL SOURCE:
        (A) ORGANISM: Triticum aestivum (xi) SEQUENCE DESCRIPTION: SEQ ID NO:19:

```
AACAGAGAAG GAGGAAGAGA GGCCGGCCGG CGAAATGAAG GCGACCGCGG GGGCCCTCCT       60

CGCCGTGGTG GCGGCGGTGC TGCTACGCGG CGTGGCGGCA GCGCCCCGGA AGCCGGTGGA      120

CGTGCCGTTC GACAAGAACT ACGTGCCGAC GTGGGCGCAG GACCACATCC ACTACGTGAA      180

CGGCGGGCGG GAGGTGCAGC TGTCCCTGGA CAAGACCACC GGCACGGGCT TCCAGACCCG      240

GGGCTCCTAC CTCTTCGGCC ACTTCAGCAT GCACATCAAG CTCGTCGGCG GCGACTCCGC      300

CGGCACCGTC ACCGCCTTCT ACCTGTCGTV ACAGAACTCG GAGCACGACG AGATCGACTT      360

CGAGTTCTTG GGGAACAGGA CGGGGCAGCC GTACATCCTG CAGACCAACG TGTTCTCCGG      420

CGGCAAGGGC GACCGGGAGC AGAGGATCTA CCTCTGGTTC GACCCAACCA AGGACTACCA      480

CTCCTACTCC GTCCTCTGGA ACCTCTACAT GATCGCGTTC TTCGTGGACG ACACGCCGAT      540

CCGGGTGTTC AAGAACAGCA AGGACCTCGG GGTGCGGTAC CCGTTCGACC AGCCCATGAA      600

GCTCTACTCC AGCCTGTGGA ACGCGGACGA CTGGGCGACC CGGGGCGGGC GGGAGAAGAC      660

GGACTGGTCA AAGGCGCCCT TCGTCGCCTC CTACCGGGGC TTCCACGTCG ACGGCTGCGA      720

GGCGTCCGCG GAGGCCAAGT TCTGCGCCAC CCAGGGCGCC CGCTGGTGGG ACCAGCCCGA      780

GTTCCAGGAC CTGGACGCCG CGCAGTACCG CCGCCTCGCC TGGGTCAGGA AGGAGCACAC      840

CATCTACAAC TACTGCACCG ACCACGACCG CT                                   872
```

(2) INFORMATION FOR SEQ ID NO:20:

(i) SEQUENCE CHARACTERISTICS:
        (A) LENGTH:  27 bases
        (B) TYPE:  nucleic acid
        (C) STRANDEDNESS:  single
        (D) TOPOLOGY:  linear (ii) MOLECULE TYPE:  other nucleic acid (xi) SEQUENCE DESCRIPTION: SEQ ID NO:20:

CTATTCTAGA CATGTAATTT TAGGCCC                                        27

(2) INFORMATION FOR SEQ ID NO:21:

(i) SEQUENCE CHARACTERISTICS:
        (A) LENGTH:  27 bases
        (B) TYPE:  nucleic acid
        (C) STRANDEDNESS:  single
        (D) TOPOLOGY:  linear (ii) MOLECULE TYPE:  other nucleic acid (xi) SEQUENCE DESCRIPTION: SEQ ID NO:21:

AGCTGAGCTC TTTCTAATGG TTTCTTC                                        27

(2) INFORMATION FOR SEQ ID NO:22:

(i) SEQUENCE CHARACTERISTICS:
        (A) LENGTH:  27 bases
        (B) TYPE:  nucleic acid
        (C) STRANDEDNESS:  single
        (D) TOPOLOGY:  linear (ii) MOLECULE TYPE:  other nucleic acid (xi) SEQUENCE DESCRIPTION: SEQ ID NO:22:

AGCTTCTAGA TTTCTAATGG TTTCTTC                                        27

(2) INFORMATION FOR SEQ ID NO:23:

(i) SEQUENCE CHARACTERISTICS:
        (A) LENGTH:  27 bases
        (B) TYPE:  nucleic acid
        (C) STRANDEDNESS:  single
        (D) TOPOLOGY:  linear (ii) MOLECULE TYPE:  other nucleic acid (xi) SEQUENCE DESCRIPTION: SEQ ID NO:23:

AGCTGAGCTC CATGTAATTT TAGGCCC                                        27

(2) INFORMATION FOR SEQ ID NO:24:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  other nucleic acid (xi) SEQUENCE DESCRIPTION: SEQ ID NO:24:

TTTTCTAGAC CATGGGTATC ATAAAAGGAG                                    30

(2) INFORMATION FOR SEQ ID NO:25:

(i) SEQUENCE CHARACTERISTICS:
        (A) LENGTH:  30 bases

-continued

```
        (B) TYPE:  nucleic acid
        (C) STRANDEDNESS:  single
        (D) TOPOLOGY:  linear (ii) MOLECULE TYPE:  other nucleic acid (xi) SEQUENCE DESCRIPTION: SEQ ID NO:25:

TTGGAGCTCA TTTTAAATAT CTCTGTCCTT                                30

(2) INFORMATION FOR SEQ ID NO:26:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  other nucleic acid (xi) SEQUENCE DESCRIPTION: SEQ ID NO:26:

TTTGAGCTCC CATGGGTATC ATAAAAGGAG                                30

(2) INFORMATION FOR SEQ ID NO:27:

(i) SEQUENCE CHARACTERISTICS:
        (A) LENGTH:  30 bases
        (B) TYPE:  nucleic acid
        (C) STRANDEDNESS:  single
        (D) TOPOLOGY:  linear (ii) MOLECULE TYPE:  other nucleic acid (xi) SEQUENCE DESCRIPTION: SEQ ID NO:27:

TTGTCTAGAA TTTTAAATAT CTCTGTCCTT                                30
```

ENDO-XYLOGLUCAN TRANSFERASE

This application is a divisional of application Ser. No. 08/445,553 filed May 22, 1995, now U.S. Pat. No. 5,840,550 which is a divisional of application Ser. No. 08/381,280 filed Jan. 31, 1995, now U.S. Pat. No. 5,516,694 which is a continuation of now abandoned application Ser. No. 08/037,281 filed Mar. 26, 1993, now abandoned, which is continuation-in-part of application Ser. No. 07/929,513 filed Aug. 14, 1992, now abandoned.

BACKGROUND OF THE INVENTION

1. Field of the Invention

This invention relates to a novel endo-xyloglucan transferase responsible for the growth of plant cell wall, gene coding for said enzyme isolated from a plant, a method of transferring xyloglucan molecules by using said enzyme.

2. Description of Related Art

Xyloglucan (hereinafter referred to simply as XG) is the major component of plant cell wall wherein XG binds to the surface of cellulose microfibrils and cross-links them into a complex network. Although it is believed that the splitting and reconnection of XG cross links are required for wall construction and reconstruction, the mechanism therefor has not been elucidated so far.

Albersheim hypothesized a mechanism for the reconstruction of XG through the function of some endo-transglycosylase [Plant Biochemistry, (1976), Academic Press, 225–274].

The present inventors previously examined an extract obtained from the apoplast (extra-plasma membrane section of plant consisting of cell wall and cell space) of epicotyls of *Vigna angularis* seedlings, a bean plant, and, as a result, found out that a fraction precipitated between 20% and 80% saturation of ammonium sulfate would enhance the polydispersity of XG molecules [Nishitani et al., Physiologia Plantarum, 82, 490–497 (1991)].

However, there has been identified no substance responsible for the reconstruction of XG molecules and the polydispersity of the molecular weight thereof. Further, no detailed mechanism therefor has been elucidated so far.

SUMMARY OF THE INVENTION

The present invention aims at isolating an enzyme responsible for the reconstruction of XG molecules and the polydispersity of the molecular weight thereof, providing said enzyme and a gene coding for said enzyme in a plant and further providing a method of cloning said gene, a method of producing said enzyme by using said gene, an antisense DNA and an antisense RNA of said gene, a method of controlling the expression of said enzyme in a living organism, a method of regulating the morphology of a plant, and a method of transferring XG molecules using said enzyme.

In the present invention, "regulating the morphology of a plant" means modification of shape, size, color, hardness, texture, content of fibrous components or aqueous components, etc. of a plant or a part of a plant.

In summary, the first invention of the present application relates to a gene coding for an endo-XG transferase. The second invention of the present application relates to a method of cloning a gene coding for an endo-XG transferase wherein the gene of the first invention of the present application or a part of the same is used as a probe. The third invention of the present application relates to an antisense DNA of a gene coding for an endo-XG transferase. The fourth invention of the present application relates to an antisense RNA of a gene coding for an endo-XG transferase. The fifth invention of the present application relates to a cassette for forming an antisense RNA wherein a DNA-sequence, which is obtained from a gene coding for an endo-XG transferase and consists of at least 15 base pairs, is linked to a promoter capable of functioning in cells in such a manner as to form the antisense RNA of a gene coding for an endo-XG transferase through transcription. The sixth invention of the present application relates to a method of controlling the expression of an endo-XG transferase which comprises introducing the cassette for forming an antisense RNA of the fifth invention of the present application into a living organism. Further, the seventh invention of the present application relates to a method for regulating the morphology of a plant which comprises introducing the cassette for forming an antisense RNA of the fifth invention of the present application into a plant to thereby control the expression of an endo-XG transferase. The eighth invention of the present application relates to a plant having the cassette for forming an antisense RNA of the fifth invention of the present application introduced thereinto. The ninth invention of the present application relates to a cassette for expressing an endo-XG transferase wherein a gene coding for an endo-XG transferase is linked to a promoter capable of functioning in cells in such a manner as to allow the expression of an endo-XG transferase. The tenth invention of the present application relates to a method of controlling the expression of an endo-XG transferase which comprises introducing the cassette for expressing an endo-XG transferase of the ninth invention of the present application into a living organism. The eleventh invention of the present application relates to a method of regulating the morphology of a plant which comprises introducing the cassette for expressing an endo-XG transferase of the ninth invention of the present application into a plant. The twelfth invention of the present application relates to a plant having the cassette for expressing an endo-XG transferase of the ninth invention of the present application introduced thereinto. The thirteenth invention of the present application relates to a method of producing an endo-XG transferase which comprises incubating a living organism or cells transformed with a gene coding for an endo-XG transferase of the first invention of the present application and obtaining the endo-XG transferase from the culture. The fourteenth invention of the present application relates to an endo-XG transferase. The fifteenth invention of the present application relates to a method of transferring XG molecules which comprises splitting a D-glucosyl linkage in a XG molecule by using an endo-XG transferase and linking the resultant reducing end of XG molecular segment to D-glucose of the non-reducing end of another XG molecule.

The present inventors found out that an enzyme responsible for the reconstruction of XG and the polydispersity of the molecular weight thereof was contained in the apoplast of epicotyls of *Vigna angularis* seedlings and isolated and purified this enzyme. Subsequently, they found out that said enzyme had a novel and valuable, from the viewpoint of plant physiology, function of splitting XG molecules and reconnecting XG molecular segments thus formed to other XG molecules.

The present inventors named this type of enzyme capable of splitting XG molecules and reconnecting XG molecular segments thus formed to other XG molecules "endo-XG transferase".

The present inventors further analyzed amino acid sequence of the endo-XG transferase derived from *Vigna*

*angularis* and determined a partial amino acid sequence thereof. Next, they prepared a PCR primer, based on the above-mentioned amino acid sequence, and effected PCR with the use of *Vigna angularis* cDNA as a template. Then a gene coding for said endo-XG transferase was amplified and thus a probe was prepared. Subsequently, clones containing a gene coding for endo-XG transferase were screened from a *Vigna angularis* cDNA library with the use of the above-mentioned probe, and a gene coding for endo-XG transferase was isolated. It has further been found that genes coding for other or similar endo-XG transferase can be cloned from various other plants by using said gene as a probe. Furthermore, the present inventors incubated an organism or cells transformed with above-mentioned gene and found out that endo-XG transferase could be thus produced thereby. The present inventors further found out that the intracellular expression of endo-XG transferase could be controlled by introducing an antisense DNA or an antisense RNA of the gene coding for endo-XG transferase into the cells or by introducing a cassette for forming an antisense RNA wherein a DNA sequence, which is obtained from the gene coding for endo-XG transferase and consists of at least 15 base pairs, is linked to a promoter capable of functioning in cells in such a manner as to form the antisense RNA of the gene coding for endo-XG transferase through transcription into the cells and that the morphology of a plant could be regulated by the method described above. Then they constructed plants having these substances introduced thereinto. Furthermore, the present inventors succeeded in the expression of an endo-XG transferase in organisms by introducing a cassette for expressing an endo-XG transferase wherein a gene coding for an endo-XG transferase is linked to a promoter capable of functioning in cells in such a manner as to allow the expression of the endo-XG transferase and that the morphology of a plant cell could be controlled by the method described above. Then they constructed plants having the cassette introduced thereinto. Thus the present invention has been completed.

In the present invention, any plant may be used so long as it can produce the endo-XG transferase. For example, *Vigna angularis* may be selected therefor. Although the enzyme of the present invention may be collected from any section of a plant without restriction, it is suitably obtained from, for example, the apoplast of epicotyls of seedlings.

Now the present invention will be described in detail with the use of *Vigna angularis* by way of example. In order to germinate *Vigna angularis* and to obtain the crude extract of the apoplast (hereinafter called "apoplastic solution") therefrom, the method described in Physiologia Plantarum as cited above may be effectively employed.

The target enzyme may be purified from the apoplastic solution thus obtained by any means which is commonly employed for purifying enzymes. For example, the purification may be effectively performed by combining salting out with ammonium sulfate, affinity chromatography, gel filtration or ion exchange column chromatography. Thus the target enzyme can be obtained in a pure state without contamination with glycosidase activity.

Now the physicochemical properties of the endo-XG transferase derived from *Vigna angularis* thus obtained (sometimes referred to as "enzyme of the present invention") will be illustrated in detail.

The function mechanism of the enzyme of the present invention is determined as follows.

Reducing ends of Tamarind-XG, which have been prepared by the method as will be described hereinafter, are coupled with 2-aminopyridine by reductive amination with sodium cyanoborohydride to thereby obtain pyridylamino XG (hereinafter referred to simply as XG-PA). A mixture of 18 $\mu$g of 630 kDa XG with 2 $\mu$g of 15 kDa XG-PA is incubated together with 20 ng of a purified specimen of the enzyme of the present invention for 20 or 60 minutes under such conditions as will be specified hereinafter regarding the determination of enzyme activity. Then the products in the reaction mixture is detected with the same HPLC system as the one employed for determining enzyme activity.

The detection is effected by using a pulsed amperometry detector (hereinafter referred to simply as PAD, manufactured by Dionex) and a fluorescent spectrometer (RF535, Ex 320 nm/Em 400 nm, manufactured by Shimadzu Corp.). FIG. 6 shows the results of the detection with PAD, while FIG. 7 shows the results of the detection with the fluorescent spectrometer. In each Figure, the arrow a shows the elution site of the 630 kDa XG and the arrow b shows that of the 15 kDa XG-PA.

In FIG. 6, the ordinate refers to PAD response (nA) while the abscissa refers to elution volume (ml). In FIG. 7, the ordinate refers to relative fluorescence intensity while the abscissa refers to elution volume (ml).

The results of the PAD measurement shown in FIG. 6 indicate that the elution site of a peak shifts toward the larger molecular weight region as the reaction proceeds. Further, the results of the measurement with the fluorescence spectrometer shown in FIG. 7 indicate that the elution site of the fluorescence-labelled XG shifts toward the larger molecular weight region. Based on these results, it can be clearly understood that an XG segment newly formed through the splitting of the 630 kDa XG reconnects to the 15 kDa XG-PA to thereby increase the molecular weight of the fluorescence labelled XG.

As Table 2 given hereinafter shows, the activity of the enzyme of the present invention does not change even when any of XG-PA, XG modified by reducing a reducing end into a sugar alcohol (hereinafter referred to simply as XG-OH) and unmodified XG is employed as a substrate.

Therefore, it can be understood that the increase in the molecular weight of XG molecules, as shown in FIGS. 6 and 7, is caused not simply by the connection of the reducing end of the 630 kDa XG molecule to the non-reducing end of the 15 kDa XG-PA but by the reconnection of the reducing end of the XG segment, newly formed via the splitting of the glycosidic linkage of the 630 kDa, to the non-reducing end of the 15 kDa XG-PA molecule.

Further, effects of the substrate molecular weight on the enzyme action of the enzyme of the present invention are examined by the following method. 20 $\mu$g portions of Tamarind-XG substrates of various molecular weights are reacted with 20 ng of the purified enzyme preparation of the present invention and the enzyme activities are determined by the method as will be described hereinbelow. Results are given in FIG. 8 wherein the ordinate refers to enzyme activity (U) while the abscissa refers to substrate molecular weight (kDa). As FIG. 8 clearly shows, the enzyme of the present invention exhibits a higher activity on a substrate of the larger molecular weight and a lower activity on that of the smaller molecular weight.

One mg portions of Tamarind XG are reacted with 1 g of the purified native enzyme preparation of the present invention or 1 $\mu$g of denatured enzyme preparation of the present invention (autoclaved at 120° C. for 5 minutes) in a sodium acetate buffer solution (pH 5.8) at 25° C. for 2 hours. After cooling to −50° C. to thereby cease the reaction, XG is collected by repeated precipitation in 80% ethanol followed by lyophilizing in heavy water.

The lyophilized product thus obtained is dissolved in heavy water to give a concentration of 1 mg/0.6 ml and the $^1$H-NMR spectrum thereof is recorded at 85° C. with the use of JEOL GSX400 (manufactured by Nippon Denshi K. K.). Chemical shifts are reported relative to sodium 4,4-dimethyl-4-silapentane-1-sulfonate employed as the internal standard. FIG. 9 shows the spectra thus obtained wherein (a) represents the spectrum obtained by using the native enzyme while (b) represents the spectrum obtained by using the denatured enzyme.

In the spectra (a) and (b), signal (1) is assignable to a water molecule one of the hydrogen atoms of which is substituted with a heavy hydrogen atom (HDO); signal (2) (chemical shift: 4.53–4.54 ppm) is assignable to the anomeric proton of the β-(1,4)-linked glucosyl residue forming the backbone chain of the Tamarind XG molecule and the galactosyl residue located at the non-reducing end of one of the two side chains having a sequence of Gal-β-(1,2)-Xyl-α-(1,6)- of the Tamarind-XG molecule; signal (3) (chemical shift. 4.927 ppm) is assignable to the anomeric proton of the xylosyl residue located at the non-reducing end of another side chain; and signal (4) (chemical shift: 5.116 ppm) is assignable to the anomeric proton of the xylosyl residue in a side chain having a Gal-β-(1,2)-Xyl-α-(1,6)-linkage.

The facts that the chemical shifts of the signals shown in the spectra (a) and (b) do not differ from each other and that the relative content of the anomeric protons of each saccharide represented by the signals (2), (3) and (4) in the spectrum (a) is the same as the one in the spectrum (b) suggest that even after the reaction with the enzyme of the present invention linkage mode same as before the reaction have been kept.

Thus it may be concluded that the enzyme of the present invention splits a D-glucosyl linkage in a XG molecule and then links the reducing end of a newly formed XG molecular segment to a D-glucosyl residue of the non-reducing end of another XG molecule. (Transfer reaction of pyridylamino XG heptamer into cell wall with endo-XG transferase)

In 40 μl of an acetate buffer solution (pH 5.7) were mixed together 600 μg (on the basis of dry weight) of a cell wall specimen, prepared by the method as will be described later, 5 μg of pyridylamino XG heptamer {XG7-PA, prepared by bonding 2-Aminopyridine to the reducing end of XG heptamer[XG7, described as XG oligomer I in Journal of Biological Chemistry, 267, 21058–21064 (1992)] by reductive amination with the use of sodium cyanoborohydride} and 3 μg of a purified specimen of the enzyme of the present invention or 3 μg of a purified specimen of the enzyme of the present invention which had been denatured by autoclaving at 120° C. for 5 minutes to effect a reaction at 25° C. for 12 hours. Then the reaction mixture was divided into the first insoluble fraction and the first soluble fraction by using an ultrafiltration membrane ultrafree C3HV (manufactured by Millipore). The first insoluble fraction was suspended in 210 μl of water and ultrafiltered again in the same manner as the one described above to thereby divide into the second insoluble fraction and the second soluble fraction. By combining the first and second soluble fractions, the soluble fraction amounted to 250 μl. This fraction was named S-fraction.

The second insoluble fraction was suspended in 100 μl of water containing 30 μg of *Trichoderma viride* cellulase [(1,4)-β-D-glucan glucanohydrolase, E.C. 3.2.1.4] purified from a crude *Trichoderma viride* enzyme preparation (Meiselase-P, manufactured by Meiji Seika Kaisha Ltd.) by gauze column chromatography [Toyama et al., J. Ferment. Technol., 42, 199–206 (1964)] and allowed to react at 40° C. for 4 hours. Then the reaction mixture was divided into the third insoluble fraction and the third soluble fraction by ultrafiltration. The third insoluble fraction was suspended in 100 μl of a 0.2 M sodium acetate solution (pH 5.7) and divided into the fourth insoluble fraction and the fourth soluble fraction by ultrafiltration. The third and fourth soluble fractions were combined with each other and the aqueous solution thus obtained was named C-fraction. Thus, the C-fraction amounted to 200 μl. To each of the S- and C-fractions was added three times as much acetonitrile and the obtained mixture was poured onto a non-metal HPLC system (manufactured by Dionex) provided with a TSK Gel Amide 80 (4.6×250 mm, manufactured by Tosoh Corp.) previously equilibrated with a 0.1 M sodium acetate buffer solution containing 65% of acetonitrile(pH5.7). This column was developed by linear gradient elution with 65%–35% acetonitrile in a 0.1 M sodium acetate buffer solution at a flow rate of 1 ml/min. The fluorescent absorption of the eluate was determined with the above-mentioned fluorescent spectrometer (RF535, set at Ex 320 nm/Em 400 nm, manufactured by Shimadzu Corp.).

FIG. 10 shows the results of the HPLC analysis on the C-fraction. In FIG. 10, the ordinate refers to relative fluorescent intensity, while the abscissa refers to elution volume (ml). In FIG. 10, (a) is a chromatogram obtained by using a denatured enzyme, (b) is a chromatogram obtained by using a native one and (c) is a chromatogram obtained by eluting unreacted XG7-PA. A peak shown by the arrow (A) is a peak showing the elution site of XG7-PA.

Table 1 shows ratios of the amounts of XG7-PA detected from the S- and C-fractions.

TABLE 1

| Ratios of amounts of detected XG7-PA | |
|---|---|
| | Detected XG7-PA* (%) |
| Added XG7-PA | 100 |
| Detected XG7-PA | |
| using denatured enzyine S-fraction | 100 |
| C-fraction | 0 |
| unrecovered | 0 |
| S-fraction | 21.5 (1) |
| C-fraction | 27.5 (2) |
| unrecovered | 51.0** |

*calculated as the areal ratio of a peak assignable to XG7-PA.
**showing the amount of XG7-PA incorporated into cell wall and calculated as 100 − [(1) + (2)].

In FIG. 10 (b), a peak shown by the arrow (A) is observed similar to the case of (c). In Table 1, when the denatured enzyme is used, XG7-PA is detected exclusively from the S-fraction, while it is detected from the C-fraction when the native enzyme is used. Based on these facts, it can be understood that XG7-PA is first incorporated in XG-chains in the cell wall specimen due to the action of the enzyme of the present invention and then excised with the cellulase.

(Substrate specificity)

20 μg portions of substrates, prepared by the method as will be described hereinafter, are reacted with 60 ng of a purified specimen of the enzyme of the present invention at 25° C. for 1 hour. Then the enzyme activities are determined by the method as will be described hereinafter. Table 2 shows the results.

TABLE 2

| Substrate (20 μg) | Average M.W. (kDa) | Enzyme activity (U) |
|---|---|---|
| Vigna XG | 202 | 1.73 |
| Vigna XG-OH | 200 | 1.63 |
| Tamarind XG | 51 | 0.87 |
| Tamarind XG-PA | 51 | 0.82 |
| Tropaeolum XG | 141 | 1.18 |
| Carboxymethyl cellulose | 123 | 0 |
| Oat β-(1,3); β-(1,4) glucan | 144 | 0 |
| Maize xylan | 84 | 0 |
| Rhodymenia β-(1,4), β-(1,3) xylan | 145 | 0 |

The basic structure of XG consists of a backbone of β-(1,4)-linked glucosyl residues with side chains linked to the 0–6 position of some of the glucosyl residues. The type of side chains and their arrangement on the main chain differ depending on the plant from which XG is derived. Tropaeolum XG and Tamarind XG are substituted with two types of side chains, namely, Xyl-α-(1,6)- and Gal-β-(1,2)-Xyl-α-(1,6), while Vigna XG contains a side chain Fuc-α-(1,2)-Gal-β-(1,2)-Xyl-α-(1,6)- in addition to Xyl-α-(1,6)- and Gal-β-(1,2)- Xyl-α-(1,6). As the above Table 1 shows, the enzyme of the present invention acts on these three XGs derived from vigna, Tamarind and Tropaeolum equally. However, this enzyme acts neither on carboxymethyl cellulose nor on oat β-(1,3),β-(1,4) glucan, which act as excellent substrates for β-1,4-glucanase.

(Optimum pH)

The effects of the pH value on the activity of the enzyme of the present invention are examined under the following conditions. 20 ng of a purified specimen of the enzyme of the present invention is reacted with 20 μg of Tamarind XG at 25° C. for 30 minutes in the McIlvaine buffer solution (0.2M $Na_2HPO_4$ and 0.1M citric acid, within a pH range of 3 to 7) or in a sodium borate buffer solution (within a pH range of 7 to 11). Then the enzyme activity is measured by the method as will be described hereinafter. FIG. 11 shows the results wherein an open circle shows the data obtained with the use of the McIlvaine buffer solution while a closed circle shows those obtained with the use of the sodium borate buffer solution. Thus it is found out that the optimum pH value of the enzyme of the present invention is around 5.8.

(Optimum temperature)

The effects of the temperature on the activity of the enzyme of the present invention are examined under the following conditions. 20 ng of a purified preparation of the enzyme of the present invention is reacted with 20 μg of Tamarind XG in an acetate buffer solution (pH 5.8) for 30 minutes at various temperatures. Then the enzyme activity is measured by the method as will be described hereinafter. FIG. 12 shows the results. Thus it is found out that the optimum temperature of the enzyme of the present invention is around 30° C.

(Molecular weight)

A purified specimen of the enzyme of the present invention obtained by the purification method as will be described hereinafter is subjected to SDS polyacrylamide gel electrophoresis. As a result, it is identified as a single band of a molecular weight of about 33,000.

(Measurement of enzyme activity)

The activity of the enzyme of the present invention is measured in the following manner: To 2 to 20 μg of Tamarind XG is added 10 μl of an enzyme suspension diluted with a 0.2 M sodium acetate buffer solution (pH 5.8). After reacting at 25° C. for 30 minutes, the reaction mixture is frozen at −50° C. to thereby cease the reaction. The reaction mixture is dissolved in 20 μl of 50 mM NaOH and supplied to a non-metal HPLC system equipped with columns of TSK gel-3000 PW (8×300 mm, manufactured by Tosoh Corp.) and TSK gel-5000 PW (8×300 mm, manufactured by Tosoh Corp.). After eluting the columns with a 30 MM NaOH solution containing 15 mM sodium acetate at a flow rate of 1 ml/min, the eluate was detected with a PAD equipped with a gold electrode.

FIG. 13 shows an example of the results of the measurement. FIG. 13 shows a PAD chromatogram obtained by the above-mentioned method wherein the ordinate refers to PAD response (nA) while the abscissa refers to elution volume (ml).

In FIG. 13, (a) shows a chromatogram obtained by using the denatured specimen of the enzyme of the present invention obtained by autoclaving at 120° C. for 5 minutes; (b) shows one obtained by using the apoplastic solution; and (c) shows one obtained by using the purified enzyme. An arrow 1 represents the elution site of the Tamarind substrate XG and an arrow 2 represents the elution site of polysaccharides.

In the chromatogram (c), the peak width at a half of the height of the peak 1 increases in proportion to the amount of the supplied enzyme. Accordingly, the peak width at a half of the height of the substrate peak is employed as an indicator for the activity of the enzyme of the present invention.

When Tamarind XG is used as a substrate, 1 U of the enzyme activity is defined as the amount of the enzyme capable of increasing the above-mentioned peak width by 2.3 ml at 25° C. within 30 minutes.

Now methods for preparing the substrates to be used in the present invention will be described. (XGs)—Crude Vigna XG derived from epicotyls of 6 day old dark-grown seedlings of *Vigna angularis* [Physiologia Plantarum, 82, 490–497(1991) and 52, 482–494 (1981)] and from dry seeds of *Tropaeolum majus* L. [McDougall et al., Plant. Physiol., 89, 883–887 (1988)] are prepared.

A crude XG derived from *Tamarindus Indica* L. is obtained from Dainippon Seiyaku Co. (trade name: Glyloid 9S).

300 mg of each crude XG is partially hydrolyzed by using 150 μg of above mentioned *Trichoderma viride* cellulase in 40 ml of an aqueous solution at 45° C. for 2 hours. The digestion product thus obtained is autoclaved to thereby denature the cellulase and then fractionated by ultrafiltration (Diaflo XM-300 and YM5, manufactured by Amicon). The fraction (40 mg or more) passing through XM-300 but retained by YM5 is dissolved in 2 ml of water. Then it is chromatographed on an HPLC (Shimadzu LC6A) provided with a Superose 6 prep. column (16×500 mm, manufactured by Pharmacia), which will be hereinafter called "system A" and eluted with 0.5 ml/min of water. Fractions are collected in 1.5 ml portions and lyophilized to thereby give XG specimens. The molecular weights of these specimens are measured with the use of the same chromatographic system as the one employed above for measuring the enzyme activity.

(Other glucans)—500 mg of carboxymethyl cellulose sodium dissolved in 40 ml of water is partially hydrolyzed with the use of 100 mg of the above-mentioned *Trichoderma viride* cellulase at 45° C. for 3 hours. After ultrafiltering and chromatographing, a fraction of 123 kDa is obtained.

50 mg of β-(1,3), β-(1,4)-glucan is prepared form oat bran in accordance with the method of Nishitani et al. [Plant Physiology, 87, 383–890 (1988)]. The obtained glucan is partially hydrolyzed with 5 μg of purified *Bacillus subtilis* glucanase [1,3-1,4-β-D-glucan-4-glucanohydrolase, purified form *Bacillus subtilis* (α-amylase preparation Ban L-20 manufactured Novo in accordance with the method described in Plant Physiology, 87, 883–890 (1988)] at 40° C. for 1 hour. By fractionating with the above-mentioned system A, glucans of 144 kDa are obtained.

(Xylans)—Glucuronoarabinoxylan with an average molecular weight of 84 kDa is prepared form the stem of 6 day old etiolated Maize seedling [Nishitani et al., J. Biol. Chem., 266, 6539–6543 (1991)].

β-(1,3)-Xylan containing β-(1,4)-linkages (146 kDa) is extracted from Rhodymenia xylan and purified with the above-mentioned system A [Plant Physiology, 87, 883–890 (1988)].

Further, 10 mg of Tamarind XG is reduced with sodium borohydride in accordance with the method given in J. Biol. Chem., 266, 6539–6543 (1991) and fractionated by gel filtration with Superose 6 prep. Thus terminally reduced XG (XG–OH) is obtained.

(Cell wall specimen) *Vigna angularis* seeds (available from Watanabe Shushi) were germinated in the dark and the hypocotyl was cut in a length of 3 cm and frozen at −50° C. After homogenizing at 0° C. in a 0.3% aqueous solution of NaCl, it was suspended in a 1 M aqueous solution of NaCl and washed. After further washing with cold water twice, it was boiled in 80% ethanol for 10 minutes, washed with ethanol, filtered through a nylon mesh (pore size: 35 μm) and dried to thereby extract the cell wall. The cell wall was suspended in water again and autoclaved at 120° C. for 20 minutes to thereby inactivate enzymes originating in plant tissues. By washing with a large amount of water and lyophilizing, a cell wall specimen was obtained.

The gene coding for endo-XG transferase can be isolated as described below.

The amino acid sequence of a purified endo-XG transferase is analyzed by using, for example, a protein sequencer. Thus the amino acid sequence at the N-terminus represented by SEQ ID NO. 11 in the sequence listing is determined. Based on this sequence, a mix primer for PCR can be prepared. For example, mix primers pAZ-1 and pAZ-2, respectively represented by the SEQ ID NO. 12 and No. 13 in the sequence listing, are synthesized on a DNA synthesizer. After purifying, these primers can be used in screening a gene coding for endo-XG transferase. For example, RNA is prepared from *Vigna angularis* and then poly(A)$^+$RNA is purified by using Oligotex-dT 30 (manufactured by Nippon Roche). Next, a cDNA is synthesized by using the above-mentioned poly(A)$^+$RNA together with, for example, a primer pTM4, its sequence is the same as that of M13 primer M4 (manufactured by Takara Shuzo Co., Ltd.) represented by the SEQ ID NO. 14 in the sequence listing except that poly T sequence is further bonded to the 3' side, under the action of a reverse transcriptase. PCR is carried out by using the obtained cDNA as a template to thereby amplify the cDNA coding for endo-XG transferase. In order to efficiently amplify the target DNA, the above-mentioned mix primer pAZ-1 and the M13 primer M4 are employed in the first PCR step and, subsequently, the second PCR step is carried out by using the reaction product thus obtained as a template with the use of the primer pAZ-2 and the M13 primer M4. Thus a DNA segment of about 1.1 kbp is amplified. The DNA segment thus amplified can be subcloned into an appropriate restriction enzyme site of an appropriate plasmid, for example, the Hinc II site of pUC 119.

Then a clone having a gene coding for endo-XG transferase can be screened from a *Vigna angularis* cDNA library or genomic library by using the amplified DNA segment thus obtained as a probe. The cDNA library can be obtained from, for example, the above-mentioned *Vigna angularis* cDNA prepared by cDNA Synthesis Kit System Plus (manufactured by Amersham). Plaque hybridization with the use of the above-mentioned amplified DNA segment as a probe makes it possible to obtain, for example, 5 positive plaques from $1 \times 10^4$ plaques. Then DNA segments inserted into the phage vector of said plaques are extracted. Thus a DNA segment of, for example, about 1.1 kbp can be obtained. FIG. 1 shows a restriction enzyme map of said segment. SEQ. ID No. 15 in the sequence listing shows a part of DNA sequence of said segment. Then this segment is inserted into an appropriate restriction enzyme site of an appropriate expression vector and an appropriate host is transformed with the use of a plasmid having said fragment inserted therein. A plasmid pUC 119 having said segment integrated into the EcoRI site of pUC119 is named pVX103 and *Escherichia coli* JM109 strain transformed with said pVX103 is named *Escherichia coli* JM109/pVX103 and deposited at the Fermentation Research Institute of the Agency of Industrial Science and Technology, Japan, under the accession number FERM BP-4104.

An endo-XG transferase can be produced on an industrial scale by preparing pVX103 from the abovementioned transformant, excising the inserted DNA segment as described above, integrating said segment into an appropriate expression plasmid, introducing it into an appropriate host and then incubating the host. For example, by using Mutan-K™ (manufactured by Takara Shuzo Co., Ltd.), a plasmid having the recognition sequence of a restriction enzyme HincII in the upstream of a gene sequence coding for an endo-XG transferase in pVX103 is constructed by point mutation in accordance with Kunkel's method [Proc. Natl., Acad. Sci. USA, 82, 488–492 (1982)]. Next, this plasmid is cleaved with a restriction enzyme HincII and thus a segment of about 1.1 kbp containing a gene sequence coding for an endo-XG transferase can be excised. To this segment is added NcoI linker (manufactured by Takara Shuzo Co., Ltd.) by using a ligation kit (manufactured by Takara Shuzo Co., Ltd.). After digesting with NcoI, this segment is inserted into the NcoI site of a plasmid pTV119N (manufactured by Takara Shuzo Co., Ltd.) and the plasmid thus obtained is named pVX110. When an *E. coli* JM109 strain having pVX110 introduced thereinto is incubated, the endo-XG transferase can be produced in the culture. FIG. 14 shows a process for constructing from pVX110 from pVX103. In FIG. 14, H, E, and N represents recognition site of HindIII, EcoRI, and NcoI, respectively. The incubation of the *E. coli* JM109 strain having pVX110 introduced thereinto may be carried out by a method commonly employed for incubating transformants. For example, the *E. coli* JM109 strain having pVX110 introduced thereinto is suspended in an L-broth containing ampicillin and a preculture is thus effected. Then, IPTG (isopropyl-β-D-galactopyranoside) is added thereto, and incubation is conducted under shaking at 37° C. overnight. Subsequently, endo-XG transferase is accumulated in culture. The endo-XG transferase can be purified from the culture by a method commonly employed for purifying enzymes. For example, after the completion of the incubation, the culture is centrifuged to thereby collect cells. Then the cells are ground by ultrasonication and subjected to a combination of techniques such as centrifugation, dialysis, ion exchange column chromatography, and gel filtration.

The gene coding for *Vigna angularis* endo-XG transferase explained above in detail is an example of genes coding for various plant endo-XG transferases of this invention and genes coding for other plant endo-XG transferases can be cloned from other plants by using the gene coding for *Vigna angularis* endo-XG transferase or a partial sequence thereof as a probe. Furthermore, the amplification and cloning of the genes coding for endo-XG transferases of other plants can be performed by using primers employed for cloning the gene coding for*Vigna angularis* endo-XG transferase. Similarly, genes coding for other plant endo-XG transferases can be also cloned from other plants by using the gene or a partial sequence thereof coding for endo-XG transferase of soy bean, Arabidopsis, tomato, wheat, maize, or rice described in this invention as a probe. For example, such plant species; in dicotyledons, soy bean, Arabidopsis, tomato, potato, rapes, sunflower, cotton, tobacco, in monocotyledons, wheats, rice, corn, sugar cane can be employed as targets for cloning. For example, the cDNA of about 1.1 kbp obtained by the above-mentioned procedure is labeled with ($\alpha$-$^{32}$P)dCTP by using a Random Primer DNA Labeling Kit to thereby give a probe for hybridization. Then a cDNA library obtained from mRNA of soybean (Glycine max) tissue (manufactured by Clonetech) can be screened by plaque hybridization with the use of this probe. Phages are isolated from positive plaques and DNA segments of about 1 kbp inserted thereinto can be purified therefrom. FIG. 2 shows a restriction enzyme map of this segment. SEQ ID NO. 16 in the sequence listing shows a part of DNA sequence of said segment. This segment can be subcloned into, for example, the EcoRI site of a plasmid pUC119. The plasmid thus obtained is named pSX102. Next, an *E. coli* JM109 strain is transformed with the use of this plasmid pSX102. The transformant thus obtained is named *Escherichia coli* JM109/pSX102 and deposited at the Fermentation Research Institute of the Agency of Industrial Science and Technology, Japan, under the accession number of FERM BP-4226. FIGS. 3, 4, and 5 respectively show restriction enzyme maps of DNA segments coding for endo-XG transferase genes originating in *Arabidopsis thaliana*, tomato and wheat which are obtained by methods similar to the above-mentioned one. SEQ ID Nos. 17, 18, and 19 of the sequence listing respectively show partial DNA sequences of these DNA segments. Plasmids having these DNA segments introduced thereinto are respectively named pAX101, pTX201, and pWX101, while *E. coli* JM109 strains transformed with these plasmids are respectively named *Escherichia coli* JM109/pAX101, *Escherichia coli* JM109/pTX201, and *Escherichia coli* JM109/pWX101, and *Escherichia coli* JM109/pWX101 is deposited at the Fermentation Research Institute of the Agency of Industrial Science and Technology, Japan, under the accession number of FERM BP-4225.

Furthermore, FIGS. 15 and 16 respectively show restriction enzyme maps of DNA segments coding for endo-XG transferase genes originating in maize and rice which are obtained by methods similar to the above-mentioned one. Plasmids having these DNA segments introduced thereinto are respectively named pCX101 and pRX102, while *E. coli* JM109 strains transformed with these plasmids are respectively named *Escherichia coli* JM109/pCX101 and *Escherichia coli* JM109/pRX102, and *Escherichia coli* JM109/pRX102 is deposited at the Fermentation Research Institute of the Agency of Industrial Science and Technology, Japan, under the accession number of FERM BP-4221.

An endo-XG transferase can be produced by preparing a gene coding for endo-XG transferase from the above-mentioned transformant, constructing an appropriate expression plasmid with the gene, transforming an appropriate host with the plasmid, and then incubating the host.

The expression of genes coding for endo-XG transferase can be controlled in living organisms. For example, the cell wall growth in plants can be regulated by controlling the expression of genes coding for endo-XG transferase. When the expression of these genes in the plants is inhibited, for example, the reconstruction of cell wall is inhibited, which makes it possible to give dwarfed plants.

Methods of controlling the expression of endo-XG transferase are not particularly restricted. For example, it can be achieved by introducing an antisense DNA or an antisense RNA of a gene coding for endo-XG transferase into a plant.

As the antisense DNA to be introduced, for example, an antisense DNA of a gene coding for endo-XG transferase or a part of the same can be used. SEQ ID Nos. 1 to 5 in the sequence listing show examples of these antisense DNAs. That is to say, SEQ ID Nos. 1 to 5 correspond respectively to the sequences of antisense DNAs of endo-XG transferase genes represented by SEQ ID Nos. 15 to 19 in the sequence listing. For example, segments obtained by appropriately cleaving some portion of these antisense DNAs or DNAs synthesized based on these antisense DNA sequences may be used.

As the antisense RNA to be introduced, for example, an antisense RNA of a gene coding for endo-XG transferase or a part of the same can be used. SEQ ID Nos. 6 to 10 in the sequence listing show examples of these antisense RNAs. That is to say, SEQ ID Nos. 6 to 10 correspond respectively to the sequences of antisense RNAs of endo-XG transferase genes represented by SEQ ID Nos. 15 to 19 in the sequence listing. For example, segments obtained by appropriately cleaving some portion of these antisense RNAs, RNAs synthesized based on these antisense RNA sequences, or RNAs synthesized by using genes coding for endo-XG transferase or some parts of the same as templates with RNA polymerase in an in vitro transcription system may be used.

The region and length of the antisense DNA or antisense RNA to be introduced are not particularly restricted, so long as said antisense DNA or antisense RNA can associate with endogenous RNA of endo-XG transferase in an organism and thus suppress the function of the same. It is desirable that the segment to be inserted consists of at least 15 base pairs.

The antisense DNAs and the antisense RNAs can be chemically modified so as to suppress the decomposition thereof in vivo.

Examples of the methods of introducing antisense DNAs or antisense RNAs into organisms include microinjection [Mol. Gen. Genetics, 202, 179–185 (1985)], the polyethylene glycol method [Nature, 296, 72–74 (1982)], the particle-gun method [Nature, 327, 70–73 (1987)], a method comprising fusing, for example, minicells, cells, or lysosomes containing an antisense DNA or an antisense RNA with protoplasts [Proc. Natl. Acad. Sci. U.S.A., 79, 1859–1863 (1982)], and the electroporation method [Proc. Natl. Acad. Sci. U.S.A., 82, 5824–5828 (1985)].

Further, an effective method thereof comprises constructing a cassette for forming an antisense RNA, wherein a DNA sequence obtained from a gene coding for endo-XG transferase is linked to a promoter capable of functioning in cells in such a manner as to form an antisense RNA of the endo-XG transferase gene through transcription, and then introducing this cassette into a plant. This cassette for forming an antisense RNA can be constructed by, for example, inserting some part of a structural gene coding for endo-XG transferase in the downstream of a promoter in such a manner as to form an antisense RNA of the gene coding for endo-XG transferase through transcription. The gene sequence to be inserted is not particularly restricted, so long as the antisense RNA formed through transcription can associate with the endogenous RNA of endo-XG transferase in an organism to thereby suppress the function of said enzyme. The segment to be inserted preferably consists of at least 15 base pairs.

For example, some part of a gene coding for endo-XG transferase may be cleaved with an appropriate restriction enzyme and then linked to an appropriate site in the downstream of the promoter in such a manner as to form an antisense RNA of the endo-XG transferase gene. Alternately, a PCR primer capable of amplifying an appropriate region of a gene coding for endo-XG transferase may be prepared based on the gene sequence of endo-XG transferase obtained of the present invention. By using this primer, then, PCR is effected with the use of a gene coding for endo-XG transferase as a template and the amplified DNA segment thus obtained is linked to the downstream of the promoter region integrated in an appropriate vector in such a direction that an antisense RNA of an endo-XG transferase gene can be formed through transcription, thus giving a cassette for forming an antisense RNA. In this case, the amplified DNA segment is inserted by selecting an appropriate restriction enzyme site located in the vector so as to form the antisense RNA of the endo-XG transferase gene. It is effective to perform PCR by using primers having recognition sequences of these restriction enzymes at the 5'-end.

Furthermore, the morphology of a plant can be regulated by constructing a cassette for expressing an endo-XG transferase, wherein a gene coding for endo-XG transferase is linked to a promoter capable of functioning in cells in such a manner as to allow the expression of said gene, and introducing this cassette into an organism such as a plant to thereby express the endo-XG transferase in the plant. The gene coding for endo-XG transferase to be inserted into the cassette for expressing endo-XG transferase may be arbitrarily selected so long as it contains regions required for the expression of the activity of the endo-XG transferase in plant cells. It preferably contains, for example, a region ranging from a sequence coding for a signal peptide to a termination codon. For example, some part of a gene coding for endo-XG transferase may be cleaved with an appropriate restriction enzyme and then linked to an appropriate site of the downstream of the promoter in such a manner that the endo-XG transferase gene can be expressed. Alternately, a PCR primer capable of amplifying an-appropriate region of a gene coding for endo-XG transferase may be prepared based on the gene sequence of endo-XG transferase obtained of the present invention. By using this primer, then, PCR is effected with the use of a gene coding for endo-XG transferase as a template and the amplified DNA segment thus obtained is linked to the downstream of the promoter region integrated into an appropriate vector in such a direction that endo-XG transferase can be expressed, thus giving a cassette for expressing endo-XG transferase. In this case, the amplified DNA segment is inserted by selecting an appropriate restriction enzyme site located in the vector. Similar to the case of the cassette for forming an antisense RNA, it is effective to perform PCR by using primers having recognition sequences of these restriction enzymes at the 5'-end.

The promoter sequence to be used in the cassette for forming an antisense RNA or for expressing endo-XG transferase is not particularly restricted, so long as it can function in cells. Either a promoter sequence originating in a gene coding for endo-XG transferase or one originating in another gene may be employed therfore.

A promoter includes a region called the TATA box which is 20 to 30 base pairs upstream of the transcription start site (+1) and responsible for the initiation of transcription with polymerase from the accurate site. The promoter sequence to be used in the present invention is not necessarily restricted to regions before or after the TATA box but may contain further upstream regions required for the association of proteins other than polymerase for controlling the expression, in addition to the above-mentioned region.

In the construction of a cassette for forming an antisense RNA, for example, the use of a promoter whereby the expression of a gene coding for endo-XG transferase is controlled in a natural plant makes it possible to reduce the amount of the endo-XG transferase produced throughout the whole life cycle of a plant organ, thus giving a dwarfed plant. By using a constitutive promoter originating in another gene, a plant organ can be morphologically changed throughout the total life cycle. AS an example of the constitutive promoter, cauliflower mosaic virus 35S promoter, which is contained in pBI121 (manufactured by Clonetech) can be used. When a promoter inducible by stimulation is used, further, a plant capable of changing its morphology depending on the growth environment can be prepared. For example, the use of a light-responsive promoter makes it possible to change the morphology of a plant depending on irradiation conditions. When a promoter specific for a certain organ or tissue is used, the morphology of only the specified organ or tissue can be changed. For example, the use of a promoter of a gene which is specifically transcribed in leaves makes it possible to change the morphology of only them. Alternately, the use of a promoter acting specifically in a certain stage of the life cycle makes it possible to elevate or reduce the activity of endo-XG transferase in the specified stage of the life cycle and, as a result, the morphology of only the specified organ or tissue can be changed. When a promoter capable of inducing transcription only in the stage of forming flower organs, for example, the morphology of only the flower organs can be changed. Alternately, the extension of pollen tubes can be suppressed by using a cassette for forming an antisense RNA constructed by using a promoter acting only in the stage of forming pollen tubes and, as a result, a male sterility plant can be obtained.

In the cassette for forming an antisense RNA or for expressing endo-XG transferase, transcription can be efficiently terminated by ligating a transcription termination sequence at the downstream of the gene segment having a gene coding for endo-XG transferase or a partial sequence of the same (hereinafter referred to simply as the inserted sequence) which is linked downstream of the promoter in such a manner that the antisense RNA of the endo-XG transferase gene is formed or the endo-XG transferase gene is expressed. As the transcription termination sequence, a sequence originating in the gene coding for endo-XG transferase or those obtained from different genes may be used therefor. Further, the translation efficiency can be elevated by linking a poly A signal sequence to the downstream of the inserted sequence. As the poly A signal sequence, one originating in a gene coding for endo-XG transferase or those obtained from different genes, for example, Agrobacterium octopine synthase [The EMBO J., 3, 835–846 (1984)] or the nopaline synthase [Mol. and Appl. Genet., I, 561–573 (1982)] may be used therefor.

The cassette for forming an antisense RNA or the cassette for expressing endo-XG transferase can be introduced into organisms by various known methods without restriction. An example of the methods effective therefor comprises inserting such a cassette into an appropriate vector and introducing said vector into an organism. In this case, the 5'- and 3'-ends of the cassette may include restriction enzyme sites, which are contained not in the cassette but only in the site of the vector into which the cassette is to be inserted, depending on the selected vector.

It is desirable that the vector into which the cassette is to be inserted contain a selectable marker gene by which transformed plants can be easily identified. As the selectable marker gene, those that make a plant resistant against an antibiotic (antibiotic-resistant genes) are usable therefor. For example, genes that make a plant resistant against G418, hygromycin, bleomycin, kanamycin, gentamicin and chloramphenicol may be used therefor. When the vector contains an antibiotic resistant gene, transformants, i.e., those having the cassette introduced thereinto can be obtained by selecting those which can grow in a medium containing the antibiotic.

Examples of the method of introducing vectors having the cassette inserted thereinto directly into organisms such as plants include the above-mentioned microinjection, the polyethylene glycol method, the particle-gun method, a method comprising fusing, for example, minicells, cells, or lysosomes containing a vector with protoplasts, and the electroporation method.

Further, these cassettes can be introduced into plants by using a plant virus as a vector. As the plant virus usable herein, for example, cauliflower mosaic virus (CaMV) can be inserted into a vector originating in, for example, *E. coli* to thereby give a recombinant and then the abovementioned cassette is inserted into the viral genome. Then the viral genome thus modified is excised from said recombinant by using restriction enzymes and inoculated into a plant. Thus the cassette can be inserted into the plant [Hohn et al., Molecular Biology of Plant Tumors, Academic Press, New York, 549–560 (1982); U.S. Pat. No. 4,407,956].

Furthermore, these cassettes can be introduced into plants by taking advantage of a characteristic that a part of a plasmid DNA of a bacterium belonging to the genus Agrobacterium is transferred to a plant genome when a plant is infected with said bacterium. A plant infected with *Agrobacterium tumefaciens*, from among bacteria belonging to the genus Agrobacterium, suffers from crown gall tumors, while one infected with *Agrobacterium rhizogenes* suffers from hairy roots. These phenomena are caused by the transfer of T-DNA (transferred DNA) regions located respectively on the Ti plasmid of *A. tumefaciens* or Ri plasmid of *A. rhizogenes*, into the plants and integration therein. In addition, there is the vir region, which is essential for the transfer of the T-DNA region into a plant and integration thereof in a plant genome, on the Ti or Ri plasmid. This vir region per se is not transferred into plants and can exert its function even it is located on a plasmid different from the one on which the T-DNA region is present [Nature, 303, 179–189 (1983)]. A target DNA can be integrated into a plant genome when infected with a bacterium belonging to the genus Agrobacterium by inserting the DNA, which is to be integrated into a plant genome, into the T-DNA region of the Ti or Ri plasmid. The part of the Ti or Ri plasmid capable of inducing crown gall tumors or hairy roots can be eliminated without damaging the transfer function and the product thus obtained can be used as a vector. Thus, various vectors are usable in the present invention. For example, the antisense RNA formation cassette or the endo-XG transferase expression cassette can be inserted into a so-called binary vector such as pBI121 (Clonetech) or pBI-H1-35S-IG (provided by Dr. Kenzo Nakamura, Nagoya Univ.) to thereby introduce these cassettes into plants.

Since these vectors are free from the vir region, the bacterium of the genus Agrobacterium to be employed for integrating the above-mentioned vectors into a plant genome should contain other plasmids having the vir region.

These vectors are shuttle vectors which can replicate not only in bacteria belonging to the genus Agrobacterium but also in *Escherichia coli*. Therefore, the manipulation of the Ti plasmid can be effected by using *Escherichia coli*. Furthermore, these vectors contain antibiotic resistant genes, which makes it possible to easily select transformants when bacteria belonging to the genus Agrobacterium and plants are transformed. In addition, these vectors contain a 35S promoter of CaMV and, therefore, genes inserted into these vectors can be constitutively expressed after being integrated into plant genomes.

All plants which can be infected with bacteria belonging to the genus Agrobacterium and the regeneration systems of which have been established can be transformed by using a vector having a cassette for forming an antisense RNA or for expressing endo-XG transferase inserted thereinto and transferring the cassette into plant genomes via a bacterium belonging to the genus Agrobacterium. Most of dicotyledonous plants can be transformed with the use of a bacterium belonging to for genus Agrobacterium. In particular, all plants which are natural hosts for bacteria of Agrobacterium can be transformed in vitro. Although monocotyledonous plants including cereals are not natural hosts for bacteria of Agrobacterium, such as rye [Nature, 325, 274–276 (1987)], corn [Science, 240, 204–207 (1988)] and rice [Nature, 338, 274–276 (1989)] can be transformed in vitro.

The transformation can be effected (1) by using protoplasts or (2) by using intact cells. The method (1) requires establishing a system that allows regeneration of plants from transformed protoplasts. On the other hand, the method (2) requires transforming tissue pieces or intact cells with the use of a bacterium belonging to the genus Agrobacterium and establishing a system that allows the tansformants to regenerate into whole plants. The transformed plants can be selected by growing in a medium containing an antibiotic capable of serving as the above-mentioned marker for transformation.

Means for regenerating plants vary from plant species to species. In general, it can be effected by forming a callus tissue from a suspension of transformed protoplasts [in the case of the method (1)] or a transformed tissue piece or intact cells on a plate [in the case of the method (2)] and then inducing shoots therefrom. The culture medium may generally contain various amino acids and hormones such as auxin and cytokinins. It can be confirmed by, for example, Southern hybridization whether or not the aimed cassette for forming an antisense RNA or the aimed cassette for expressing endo-XG transferase can be inserted into the plant genome of the transformed plant. It can be confirmed by, for example, Northern hybridization whether or not the sense RNA or the antisense RNA of endo-XG transferase gene has been formed in the plant.

The use of the plant having the cassette for forming an antisense RNA or the cassette for expressing endo-XG transferase thus obtained makes it possible to transfer a cassette for forming an antisense RNA or a cassette for expressing endo-XG transferase into plants of the subsequent generation through mating.

For example, a cassette for forming an antisense RNA or a plasmid containing a cassette for expressing endo-XG transferase, which is composed of a cauliflower mosaic virus 35S promoter located upstream and a gene coding for endo-XG transferase or its partial sequence at the downstream, can be constructed by integrating the gene coding for endo-XG transferase or its partial sequence obtained of the present invention into a vector pBI-H1-35S-IG in such a direction that an antisense RNA is formed through transcription or the endo-XG transferase is expressed. By using the plasmids thus constructed, an appropriate bacterium strain belonging to the genus Agrobacterium such as *Agrobacterium tumefaciens* LBA4404 [Nature, 303, 179–180(1983); available from Clonetech] is transformed. Then plants can be transformed by infecting with the transformant obtained above. Further, these plasmids, for example, pAX301, pAX302, pTX301, and pTX302 which will be described later, are digested with appropriate restriction enzymes such as HindIII and SacI and electrophoresed on agarose gels and then the target fragments are excised and purified. These fragments are usable in the transformation of plants by integrating into other plasmids, for example the HindIII-SacI site of pBI101 as a cassette for expressing endo-XG transferase or a cassette for forming an antisense RNA.

For example, four primers ATX-AS, ATS-AS, ATX-S and ATS-S expressed by SEQ ID Nos. 20,21,22 and 23 in the sequence listing can be designed and synthesized based on the sequence of a gene coding for *Arabidopsis thaliana* endo-XG transferase represented by SEQ ID NO. 17 in the sequence listing obtained by the present invention. The primers ATS-AS and ATX-S are ones wherein the recognition sequence of a restriction enzyme SacI and XbaI is added, respectively, to the 5'-side of the sequence corresponding to base Nos. 40 to 56 in SEQ ID NO. 17 in the sequence listing in the direction of 5'→3', while the primers ATX-AS and ATS-S are ones wherein the recognition sequence of a restriction enzyme XbaI and SacI is added, respectively, to the 5'-side of the sequence corresponding to base Nos. 1007 to 1023 in the direction of 3'→5'.

By using, for example, a gene coding for endo-XG transferase of *Arabidopsis thaliana* as a template, the gene sequence is amplified by the PCR method with the use of a pair of the primers ATS-AS and ATX-AS, from among those cited above, and a DNA segment of about 1 kbp thus amplified is cleaved with restriction enzymes XbaI and SacI. After purifying, it can be inserted into a site between the XbaI site and the SacI site of pBI-H1-35S-IG. The plasmid thus obtained is named pAX301. This pAX301 has a cauliflower mosaic virus 35S promoter and the sequence of the part expressed by base Nos. 40 to 1023 in SEQ ID NO. 17 in the sequence listing, which is integrated in such a manner as to allow the formation of the antisense RNA of endo-XG transferase gene through transcription, in the XbaI site-SacI site downstream of said promoter. It contains genes resistant against kanamycin and hygromycin.

Similarly, the gene is amplified by the PCR method by using a pair of the primers ATX-S and ATS-S and the DNA segment of about 1 kbp thus amplified is inserted into a site between the XbaI site and the SacI site of pBI-H1-35S-IG. The plasmid thus obtained is named pAX302. This plasmid pAX302 has a promoter and resistant genes similar to those carried by the above-mentioned pAX301 and a sequence represented by the base Nos. 40 to 1023 in SEQ ID NO. 17 in the sequence listing is integrated thereinto in such a direction as to allow the expression of endo-XG transferase.

By using these plasmids pAX301 and pAX302, for example, an *Agrobacterium tumefaciens* LBA4404 strain can be transformed by the electroporation method [Shokubutsu Saibo Kogaku (Plant Cell Engineering), vol. 4, 193–203, Shujunsha (1992)].

An *Escherichia coli* JM109 strain is transformed with pAX301. The transformant thus obtained is named *Escherichia coli* JM109/pAX301 and deposited at the Fermentation Research Institute of the Agency of Industrial Science and Technology, Japan, under the accession number of FERM BP-4222.

Methods of transforming the aimed plant with a transformed bacterium of the genus Agrobacterium are not particularly restricted. For example, a sterile plant is grown and a piece of this plant is incubated in a callus-inducing medium [a CIM plate; which had been prepared by adding 2,4-D (2,4-dichlorophenoxyacetic acid, manufactured by Wako Pure Chemical Industries, Ltd.) in such an amount as to give a final concentration of 0.5 µg/ml and kinetin (manufactured by Wako Pure Chemical Industries, Ltd.) in such an amount as to give a final concentration of 0.05 µg/ml to an MSO plate(4.6 g of Murashige-skoog inorganic salts, 10 g of sucrose, 1 ml of 1000×vitamin stock solution, each per liter, pH 6.2)]for several days and then infected with a transformed Agrobacterium. Then excess amount of Agrobacterium cells is removed from the infected plant piece, which is incubated and transplanted into a plate containing antibiotics capable of serving as selectable markers for the employed vector. After incubating, transformed plants can be selected. It can be confirmed whether or not a cassette for forming an antisense RNA or a cassette for expressing endo-XG transferase has been inserted into the genomes of these plants obtained on the plate containing the antibiotics by extracting DNA of these plants or plants formed from seeds thereof and subjecting the DNA to, for example, Southern hybridization by using the endo-XG transferase gene or its partial sequence as a probe.

It can be confirmed whether or not the expression of the endo-XG transferase gene is controlled in the transformed plants by extracting RNA of the transformed plants by or plants obtained from seeds thereof and subjecting the RNA to, for example, Northern hybridization by using the endo-XG transferase gene or its partial sequence as a probe.

For example, *Arabidopsis thaliana* seeds are grown under sterile conditions in a conventional manner and root explants thereof are subjected to callus incubation on a CIM plate which is described above. Agrobacterium strains transformed with pAX301, pAX302 and pBI-H1-35S-IG are each cultured, diluted and pipetted into tubes. Then the callused root explants are immersed therein and co-incubated on the CIM plate for several days. When each strain has grown enough to be observable, excess amount of Agrobacterium cells is removed from the culture, which is further incubated on a shoot-inducing medium [an SIMC plate; prepared by adding 2-ip{$N^6$-(2-isopentanyl)adenine} (manufactured by Wako Pure Chemical Industries, Ltd.), IAA (3-indoleacetic acid, manufactured by Wako Pure Chemical Industries, Ltd.) and Claforan respectively in such amounts as to give final concentrations of 5 µg/ml, 0.15 µg/ml and 500 µg/ml to an MSO plate] for several days.

These explants are finally incubated on an SIMCS plate (an SIMC plate containing kanamycin and hygromycin B) and transplanted into a fresh plate every week. The transformed explants continue to grow and form convex calluses, while untransformed ones turn brown. The transformants are incubated until rosette leaves are formed, then cut at the base with a scalpel in such a manner that no callus part is contained therein and transplanted into a root-inducing medium (RIM plate; prepared by adding IAA to an MSO plate in such an amount as to give a final concentration of 0.5

μg/ml). After 8 to 10 days, they are transplanted into a Rock Fiber Minipot (manufactured by Nitto Boseki Co., Ltd.) immersed in an inorganic salt medium which will be described hereinafter and incubated therein. Plants undergoing flowering and podding are transplanted into a soil immersed in the inorganic salt medium and thus seeds can be obtained. These seeds are sterilized, sowed on an MSH plate (containing hygromycin B) which will be described hereinafter and germinated, thus obtaining a transformant. A DNA extracted from this transformant in a conventional manner is cleaved with a restriction enzyme HindIII or PstI and subjected to Southern hybridization with the use of a DNA segment of about 1 kbp, which has been amplified by using a pair of the primers ATX-S and ATS-S as described above, as a probe. Thus the result of the transformation can be confirmed. More specifically, among an untransformed WS strain (1), a transformant (2) having pAX301 introduced thereinto, another transformant (3) having pAX302 introduced thereinto and another transformant (4) having vector pBI-H1-35S-IG alone introduced thereinto, both of the transformants (2) and (3) contain a specific signal of about 1 kbp, which is observed in a sample cleaved with HindIII, and that of about 3 kbp, which is observed in a sample cleaved with PstI, in addition to endogenous signals common to the strains (1) to (4). These results prove that a DNA coding for endo-XG transferase has been integrated into both of the strains (2) and (3).

Further, the expression of endo-XG transferase in the above strains (1) to (4) can be observed by extracting RNAs from the strains (1) to (4) in a conventional manner, constructing probes having a sense DNA sequence of about 1 kbp or an antisense DNA sequence by a method which will be described hereinafter, and effecting Northern hybridization by using these probes. Namely, when the sense DNA sequence is used as a probe, no band is observed in the strains of above-mentioned (1), (3), (4), however, a band about 1 kbp is observed only in the strain of (2). When the antisense DNA sequence is used as a probe, bands of about 1 kbp are observed in all of the strains (1) to (4). The signal intensity of said band in (3) is higher than that of (1), while a weak signal is detected from (2). Thus, it is confirmed that the expression of the endo-XG transferase is intensified in the strain (3) but suppressed in the strain (2).

By using a method similar to the above-mentioned one, transformants of other plants such as tobacco can be constructed by using, for example, the sequence of a gene coding for endo-XG transferase of tomato which is obtained according to the present invention.

For example, based on the sequence of a gene coding for endo-XG transferase of tomato, which is a plant belonging to the same family as tobacco does, represented by SEQ ID NO. 18 in the sequence listing, four primers TOMXSP, TOMSAP, TOMSSP and TQMXAP represented respectively by SEQ ID Nos. 24, 25, 26, and 27 in the sequence listing can be designed and synthesized. The primers TOMXSP and TOMSSP are ones wherein the recognition sequence of a restriction enzyme XbaI and SacI is added to the 5'-side of a sequence corresponding to the base Nos. 46 to 66 in SEQ ID No. 18 in the sequence listing in the direction of 5'→3', while the primers TOMSAP and TOMXAP are ones wherein recognition sequence of a restriction enzyme SacI and XbaI is added to the 5'-side of a sequence corresponding to the base Nos. 921 to 941 in the direction of 3'→5'.

By using a gene coding for endo-XG transferase of tomato as a template, for example, a gene sequence can be amplified by the PCR method with the use of a pair of the primers TOMXSP and TOMSAP, from among the above-mentioned ones. Then the DNA segment of about 930 bp thus amplified is cleaved with restriction enzymes XbaI and SacI. After purifying, it can be inserted into a site between the XbaI site and the SacI site of pBI-H1-35S-IG. The plasmid thus obtained is named pTX301. In this pTX301, a partial sequence of a structural gene coding for tomato endo-XG transferase, which is represented by the base Nos. 46 to 941 in SEQ ID NO. 18 in the sequence listing, is integrated into the XbaI site-SacI site downstream of the cauliflower mosaic virus 35S promoter in such a direction as to allow the expression of the endo-XG transferase. It contains a gene resistant against kanamycin and hygromycin. Similarly, a gene is amplified by the PCR method with the use of a pair of the primers TOMSSP and TOMXAP and a DNA segment of about 930 bp thus amplified is inserted into a site between the XbaI site and the SacI site of pBI-H1-35S-IG. The plasmid thus obtained is named pTX302. In this pTX302, which has a promoter and a resistant gene both same as the corresponding ones in pTX301, the sequence corresponding to the base Nos. 46 to 941 in SEQ ID NO. 8 in the sequence listing is integrated in such a manner as to allow the formation of an antisense RNA through transcription.

By using these plasmids, an appropriate strain belonging to the genus Agrobacterium, for example, an *Agrobacterium tumefaciens* LBA4404 strain can be transformed by the same method as the one described above.

An *Escherichia coli* JM109 strain is transformed with pTX301 and pTX302. The transformants thus obtained are respectively named *Escherichia coli* JM109/pTX301 and *Escherichia coli* JM109/pTX302 and deposited at the Fermentation Research Institute of the Agency of Industrial Science and Technology, Japan, under the accession numbers of FERM BP-4223 and FERM BP-4224.

By using Agrobacterium strains transformed with pTX301 and pTX302, tobacco plants transformed with pTX301 and pTX302 can be constructed in the same manner as the one employed in the above-mentioned case of *Arabidopsis thaliana*. From these transformants, DNAs are extracted by a conventional method and digested with a restriction enzyme PstI. Then Southern hybridization is effected by using, for example, a DNA segment amplified by PCR with the use of a pair of the above-mentioned primers TOMSSP and TOMXAP as a probe and thus it can be confirmed whether or not the transformation has been done.

Namely, tobacco plants having pTX301 and pTX302 introduced thereinto show bands in addition to the one which is supposed to the tobacco endo-XG transferase gene, compared with a control tobacco plant having pBI-H1-35S-IG alone introduced thereinto and an untransformed one. Alternately, a band of an intense signal which is clearly different from that found in a control tobacco is detected. Thus it can be confirmed that the structural gene coding for tomato endo-XG transferase has been introduced into the tobacco plants having pTX301 and pTX302 introduced thereinto.

Further, expression of the endo-XG transferase can be confirmed by extracting RNAs from these transformants, constructing probes having a sense DNA sequence or an antisense DNA sequence therefrom by a method which will be described hereinafter and effecting Northern hybridization with the use of these probes. When a probe having the sense DNA sequence is used, namely, the tobacco plants having pBI-H1-35S-IG and pTX301 introduced thereinto and the untransformed tobacco plant show no corresponding band while the one having pTX302 introduced thereinto shows the corresponding band. When a probe having the antisense DNA sequence is used, on the other hand, the tobacco plant having pBI-H1-35S-IG introduced thereinto and the untransformed tobacco plant show each a corresponding band while the one having pTX301 introduced thereinto shows a band of an elevated intensity. The tobacco plant having pTX302 introduced thereinto shows only a faint band. Based on these results, it is proved that the expression of endogenous endo-XG transferase is intensified by introducing pTX301 but suppressed by introducing pTX302.

When the reconstruction of XG molecules is repeated a number of times under appropriate conditions by using the endo-XG transferase obtained by, the present invention, XG molecules of an arbitrary structure can be constructed, which is applicable to, for example, the synthesis of chimeric polysaccharides.

It is also possible to vary the plant cell wall structure by using the endo-XG transferase, which is useful in processing plant materials to be used in the industrial fields. The process for the expression of a gene coding for endo-XG transferase can be observed and controlled by using the gene coding for endo-XG transferase and a gene hybridizable therewith or a polynucleotide having a partial sequence thereof obtained by the present invention. Furthermore, various antibodies can be immunologically produced by using polypeptides obtained through the expression of the gene coding for endo-XG transferase obtained in the present invention. These antibodies are also useful in, for example, the purification of endo-XG transferase.

BRIEF DESCRIPTION OF THE FIGURES

FIG. 1 shows the restriction enzyme map of an example of the gene segments coding for endo-XG transferase of *Vigna angularis*.

FIG. 2 shows the restriction enzyme map of an example of the gene segments coding for endo-XG transferase of soy bean.

FIG. 3 shows the restriction enzyme map of an example of the gene segments coding for endo-XG transferase of *Arabidopsis thaliana*.

FIG. 4 shows the restriction enzyme map of an example of the gene segments coding for endo-XG transferase of tomato.

FIG. 5 shows the restriction enzyme map of an example of the gene segments coding for endo-XG transferase of wheat.

FIG. 6 shows the PAD chromatogram obtained by measuring the transfer reaction of XG molecules with the endo-XG transferase.

FIG. 7 shows the fluorescent chromatogram obtained by measuring the transfer reaction of XG molecules with the endo-XG transferase by using a fluorophotometer.

FIG. 8 shows the relationship between the activity of the endo-XG transferase and substrate molecular weight.

[FIG. 9]

FIG. 9 shows the 1H-NMR spectra of the products obtained by reacting XG with the endo-XG transferase or denatured enzyme of the present invention.

[FIG. 10]

FIG. 10 is a graph formed by measuring the transfer reaction of XG7-PA into cell wall with the endo-XG transferase by using a fluorophotometer.

[FIG. 11]

FIG. 11 shows the relationship between the activity of the endo-XG transferase of *Vigna angularis* and pH.

FIG. 12 shows the relationship between the activity of the endo-XG transferase of *Vigna angularis* and temperature.

FIG. 13 shows the PAD chromatogram obtained by measuring the product of the enzymatic reaction of the endo-XG transferase of *Vigna angularis*.

FIG. 14 shows the process for constructing a plasmid pVX110.

FIG. 15 shows the restriction enzyme map of an example of the gene segments coding for endo-XG transferase of maize.

FIG. 16 shows the restriction enzyme map of an example of the gene segments coding for endo-XG transferase of rice.

Figure 1:
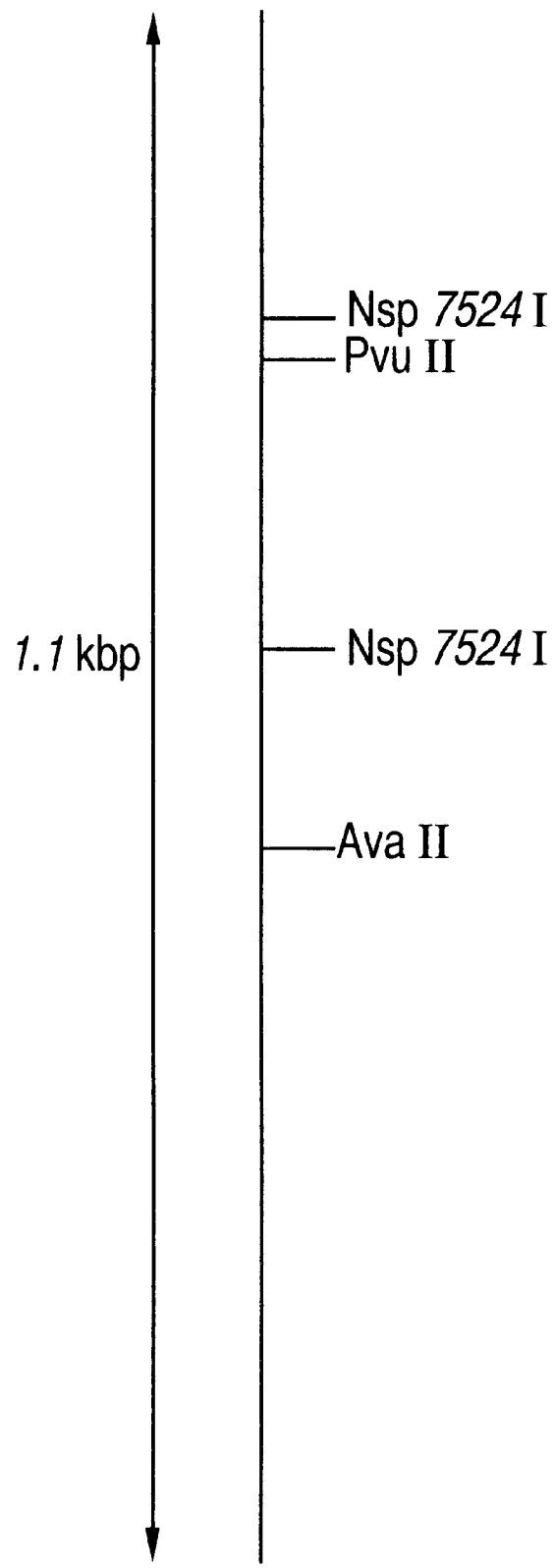
[FIG. 1]

The following examples further illustrate the invention but are not intended to limit its scope.

EXAMPLE 1

Purification of Endo-XG Transferase

Seeds of *Vigna angularis* Ohwi et Ohashi cv. Takara (obtained from Watanabe Seed Co., Ltd.) were germinated by the method described in Physiologia Plantarum, 82, 490–497 (1991) and thus an apoplast solution was obtained. (Ammonium sulfate precipitation)

600 ml, in total, of the apoplastic solution was mixed with 10 g of a polyvinylpyrrolidone powder and 60 ml of a 0.5 M sodium phosphate buffer solution (pH 6.8) containing 50 mM dithiothreitol and 2 mM EDTA at 0° C. and kept for 5 minutes. After removing the insoluble matters by centrifuging at 18,000×G for 30 minutes, an ammonium sulfate powder was added to the supernatant to achieve 80% saturation. Then the precipitate thus formed, containing 10.5 mg of protein, was recovered by centrifugation. The obtained precipitate was dissolved in 2 ml of a 0.2 M sodium acetate buffer solution (pH 5.7) and 1 ml of a 100%-saturated solution of ammonium sulfate was added thereto to thereby achieve 33% saturation. The precipitate thus formed was centrifuged at 18,000×G for 30 minutes and a fraction containing 1.8 mg of protein was obtained.

(Fractionation with Con-A Sepharose 6B)

The precipitate obtained above was dissolved in 2.4 ml of a sodium acetate buffer solution a (pH 5.7) containing 0.15 M NaCl, 1 mM $MnCl_2$, 1 mM $MgCl_2$ and 1 mM $CaCl_2$ and poured into a column packed with 4 ml of Con-A Sepharose 6B (manufactured by Pharmacia) which had been equilibrated with the same buffer solution a. This column was eluted successively with 36 ml of the buffer solution a, 20 ml of the buffer solution a containing 7 mM methyl α-D-mannopyranoside and 40 ml of the buffer solution a containing 500 mM methyl α-D-mannopyranoside continuously. The activity of the enzyme of the present invention was found in the fraction eluted with the buffer solution a containing 500 mM methyl α-D-mannopyranoside. The active fraction was then concentrated by ultrafiltration with the use of Ultrafree (manufactured by Millipore) to give 400 μl of a fraction containing 668 μg of protein.

(Fractionation with TSK gel 2000SW)

200 μl of the protein in the fraction obtained above was chromatographed on a column of TSK gel G2000SW (7.5× 300 mm, manufactured by Tosoh Corp.) with the use of a 0.15 M sodium acetate buffer solution (pH 5.7) as the eluent at a flow rate of 0.5 ml/min. This chromatographic operation was repeated and active fractions were combined and concentrated. Thus a fraction containing 60 μg of protein in 100 μl of the above-mentioned buffer solution was obtained.

(Fractionation with Mono-S)

The fraction obtained by the above procedure was diluted with 500 μl of a 20 mM sodium acetate solution and poured onto a column (5×50 mm) of Mono-S (manufactured by Pharmacia) which had been previously equilibrated with a 40 mM sodium acetate buffer solution (pH 5.7). This column was first eluted with 2.5 ml of the 40 mM sodium acetate buffer solution followed by elution with 20 ml of the 40 mM sodium acetate buffer containing a linear gradient of 0–1 M NaCl at a flow rate of 0.4 ml/min. Thus approximately 30 μg of a purified specimen of the enzyme of the present invention was obtained.

Table 3 shows the results of the above-mentioned purification processes.

TABLE 3

Purification of endo-XG transferase from *Vigna angularis*

| Process | Total protein (mg) | Total activity (U) | Specific activity (U/μg protein) | Yield (%) | Purification (-fold) |
|---|---|---|---|---|---|
| Apoplastic solution | 10.5 | 2136 | 0.203 | 100 | 1 |
| 33% $(NH_4)_2SO_4$ | 1.513 | 1766 | 1.17 | 82 | 5.7 |
| Con-A Sepharose | 0.668 | 938 | 1.40 | 43 | 6.9 |
| TSK 2000SW | 0.06 | 816 | 13.6 | 38 | 67 |
| Mono-S | 0.03 | 530 | 17.7 | 24 | 87 |

Figure 13:
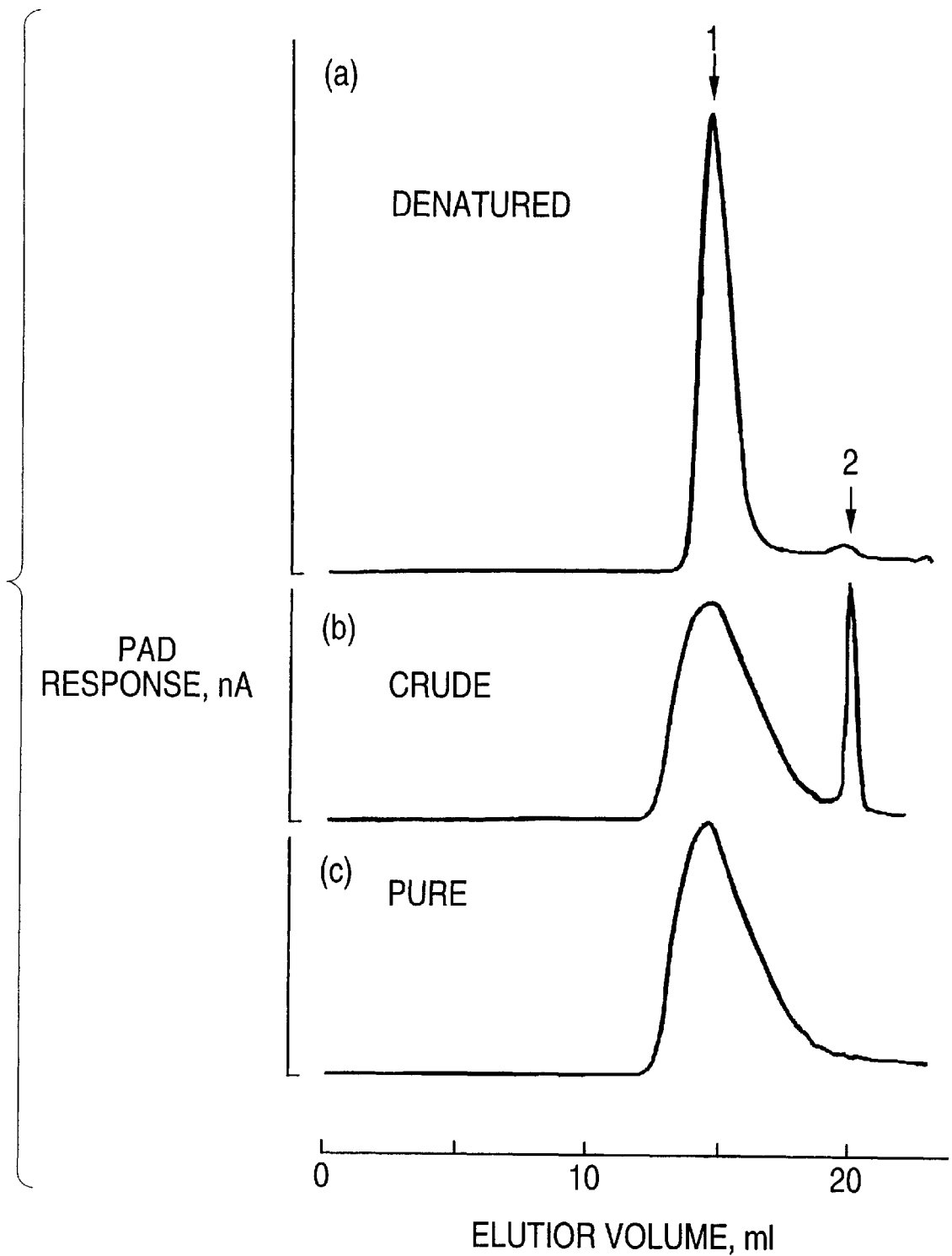
[FIG. 13]

In FIG. 13, (b) is a chromatogram obtained by a reaction with the use of the apoplastic solution and an arrow 2 in FIG. 13 represents the elution site of monomer saccharides formed by the contaminant glycosidase. In the chromatogram (c), which is obtained by a reaction with the use of the purified enzyme, no peak assignable to the monomeric saccharides is observed, which indicates that the contaminant glycosidase had been removed by the purification process.

(SDS-polyacrylamide gel electrophoresis)

The purified specimen of the enzyme of the present invention obtained by the above purification process was subjected to SDS polyacrylamide gel electrophoresis in accordance with the method of Laemmili et al. [Nature, 227, 680–685 (1970)]. Namely, a 12% polyacrylamide gel containing SDS (10×10 cm, 1 mm in thickness) was used and protein bands were stained with silver. Thus the purified specimen of the enzyme of the present invention was identified as a single band of a molecular weight of about 33,000.

EXAMPLE 2

Cloning of Gene Coding for Endo-XG Transferase (1) Preparation of poly(A)$^+$RNA Seeds of *Vigna angularis* Ohwi et Ohashi cv. Takara were germinated by the method described in Physiologia Plantarum as cited above. One week after the germination, the stem 2 to 5 cm below the bud tip was cut to thereby give about 3 g of a plant tissue. The tissue was immediately frozen in liquid nitrogen and ground in a mortar in the presence of liquid nitrogen. The obtained powder was then dissolved in approximately 30 ml of a denaturing solution [4 M guanidine thiocyanate, 25 mM sodium citrate (pH 7.0), 0.1 M 2-mercaptoethanol, 0.5% N-lauroylsarcocine sodium salt], 3 ml of 2 M sodium acetate (pH 4.0), and 30 ml of water-saturated acidic phenol and 6 ml of chloroform/isoamyl alcohol mixture (49:1) were successively added thereto followed by thorough stirring. The resulting suspension was centrifuged. To the aqueous layer thus obtained was added isopropanol and the mixture was centrifuged. Thus approximately 1 mg of a precipitate of RNA was obtained. This precipitate was dissolved in 400 μl of an elution buffer solution [10 mM Tris-HCl (pH 8.0), 1 mM EDTA (pH 8.0), 0.1% SDS] and 1 ml of Oligotex-dT30 (manufactured by Nippon Roche) was added thereto to thereby adsorb exclusively poly(A)$^+$RNA by the resin. The resin was washed with autoclaved pure water and thus approximately 10 μg of poly(A)$^+$RNA was recovered.

(2) Determination of N-terminal Amino Acid Sequence of Endo-XG Transferase

By using approximately 1 nmol of the purified endo-XG transferase specimen obtained in the above Example 1, the amino acid sequence of about 30 residues located in the N-terminus was determined with a Protein Sequencer 470A (manufactured by Applied Biosystems). This amino acid sequence is represented by the SEQ ID NO. 11 in the sequence listing.

(3) Amplification of Endo-XG Transferase Gene by PCR

Based on the amino acid sequence determined in the above (2), primers pAZ-1 (SEQ ID NO. 12) and pAZ-2 (SEQ ID NO. 13) were designed and synthesized on a DNA synthesizer. Further, another primer pTM4 of a sequence wherein additional 20 T residues were bound to the 3'-side of the sequence of M13 primer M4 (manufactured by Takara Shuzo, Co. Ltd.) was similarly synthesized. The sequence of this primer pTM4 is represented by the SEQ ID NO. 14 in the sequence listing.

2 μg of poly(A)$^+$RNA obtained in the above (1) was added to a reaction mixture (total volume: 20 μl) containing 5 mM $MgCl_2$, 50 mM KCl, 10 mM Tris-HCl (pH 8.3), 0.01% gelatin, 1 mM dNTP, 2.5 pH primer pTM4, 20 U RNase inhibitor, and 50 U reverse transcriptase RAV-2. Then reverse transcription was effected at 42° C. for 40 minutes to thereby synthesize a cDNA.

To this tube were successively added 4 μl of 25 mM $MgCl_2$, 8 μl of 10×PCR buffer solution [500 mM KCl, 100 mM Tris-HCl (pH 8.3), 0.1% gelatin], 65.5 μl of sterilized distilled water, 2.5 U of Ampli Taq (trade mark) DNA polymerase (manufactured by Perkin-Elmer Cetus Instruments), 20 pmol of the primer pAZ-1, and 20 pmol of the M13 primer M4 (manufactured by Takara Shuzo Co., Ltd.). After further adding mineral oil, the mixture was subjected to PCR. The reaction was effected by repeating a cycle (94° C. for 0.5 minute, 45° C. for 2 minutes and 72° C. for 1 minute) 30 times and then maintaining at 72° C. for 7 minutes. Next, PCR was carried out in the same manner with the use of 1 μl of the reaction mixture as a template, the primer pAZ-2 as a sense primer, and the M13 primer M4 as an antisense primer. After repeating the above-mentioned cycle 25 times, the reaction mixture was subjected to agarose gel electrophoresis. Thus it was confirmed that a cDNA of approximately 1.1 kbp was specifically amplified. This cDNA was purified and subcloned into the restriction enzyme site (HincII) of a vector pUC 119.

(4) Preparation of cDNA Library and Screening

Figure 8:
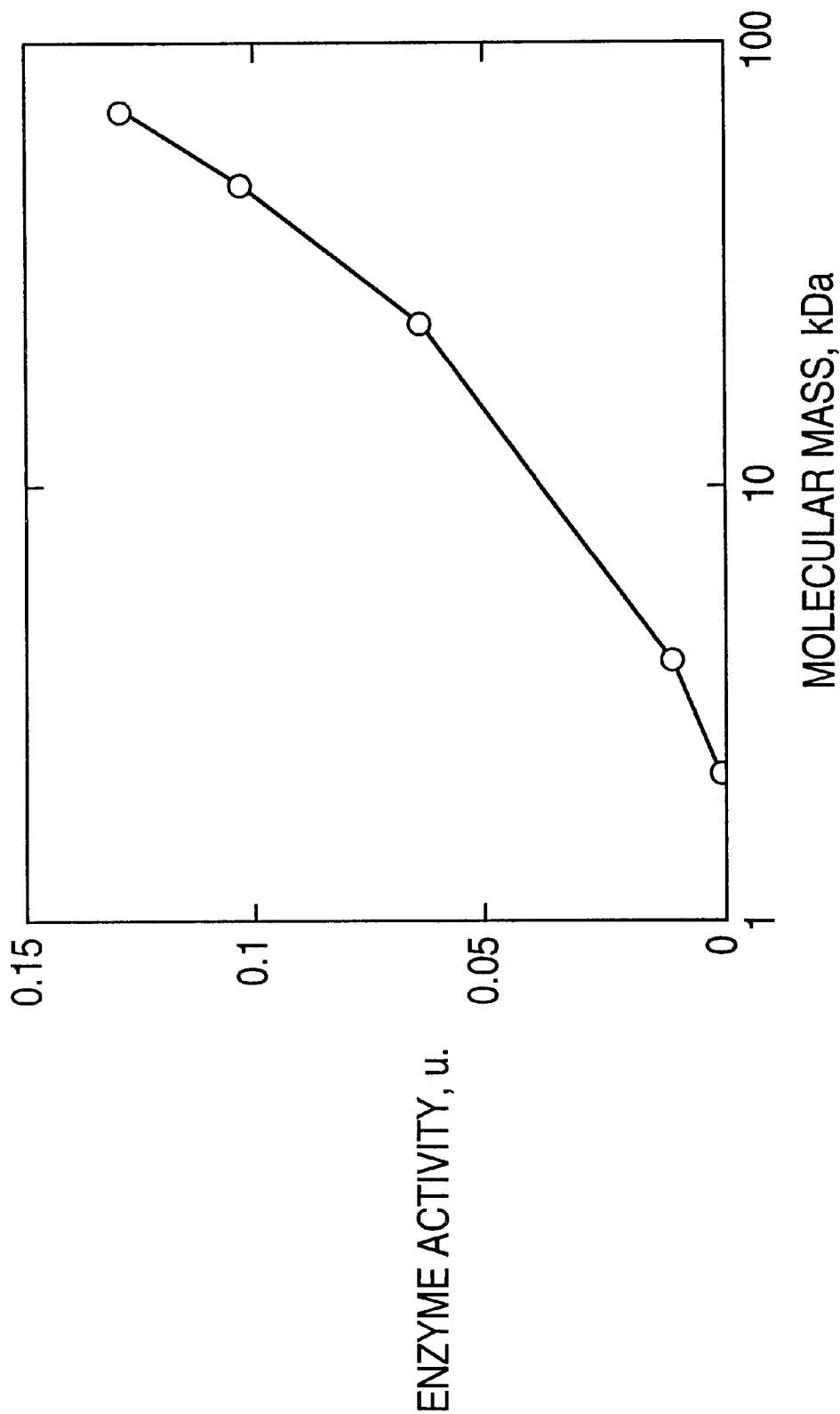
[FIG. 8]
Figure 12:
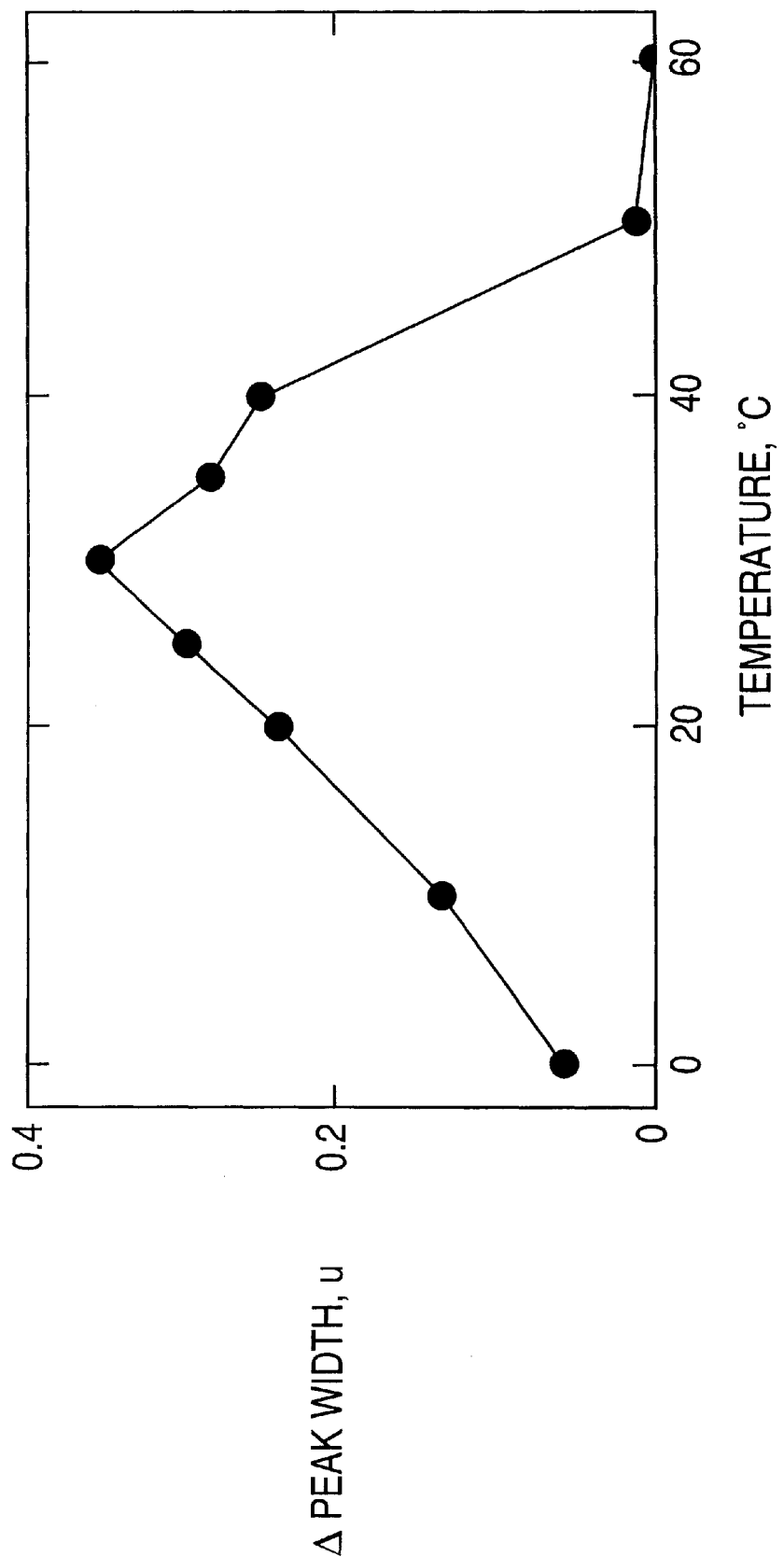
[FIG. 12]

Starting with the poly(A)⁺RNA obtained in the above (1), a cDNA library with λgt 10 as a vector was prepared in accordance with the method described in Gene, 25, 263 (1983) with the use of a cDNA Synthesis Kit System Plus (manufactured by Amersham). The cDNA of approximately 1.1 kbp subcloned in the above (3) was then labelled with [α-$^{32}$P]dCTP by using a random primer DNA Labeling Kit (manufactured by Takara Shuzo Co., Ltd.) to thereby give a probe for hybridization. Then the cDNA library obtained above was subjected to plaque hybridization with the use of this probe. By examining 1×10⁴ plaques, 5 positive plaques were obtained. Then phages were isolated from these positive plaques and the DNAs inserted thereinto were extracted. These DNAs were cleaved with a restriction enzyme EcoRI and the length of each DNA segment was determined by agarose gel electrophoresis. A DNA segment of approximately 1.1 kbp was purified and subcloned into the EcoRI site of the plasmid pUC 119. The plasmid thus obtained was named pVX103. The obtained DNA segment of approximately 1.1 kbp was cleaved with several restriction enzymes and analyzed by agarose gel electrophoresis. FIG. 8 shows the results. That is to say, FIG. 8 is a restriction enzyme map of the DNA segment of approximately 1.1 kbp. The segment cannot be cleaved with such restriction enzymes, as BamHI, HindIII, and KpnI. An *Escherichia coli* JM109 strain was transformed with the plasmid pVX103 and the transformant thus obtained was named *Escherichia coli* JM109/pVX103. This strain has been deposited at the Fermentation Research Institute of the Agency of Industrial Science and Technology, Japan, under the accession number FERM BP-4104.

EXAMPLE 3

Determination of DNA Sequence of Endo-XG Transferase Gene

10 μg of the plasmid pVX103 obtained in the above Example 2 was cleaved with restriction enzymes XbaI and PstI. Then a DNA segment integrated into a vector was digested from the recognition sequence site of XbaI in accordance with the method of Henikoff et al. [Gene, 28, 351–359 (1984)] by using a Kilo Sequence Deletion Kit (manufactured by Takara Shuzo Co., Ltd.) to thereby give clones containing segments of various sizes. Eight plasmids containing segments of appropriate sizes were selected therefrom and the sequence of a DNA segment of about 1.1 kbp was determined in accordance with Sanger's method [Science, 214, 1205–1210 (1981)] by using a BcaBEST™ Labeling Kit (manufactured by Takara Shuzo Co., Ltd.). SEQ ID No. 5 in the sequence listing shows a part of this sequence. In the SEQ ID NO. 5 in the sequence listing, the region represented by the base Nos. 57 to 872 corresponds the coding sequence for endo-XG transferase of *Vigna angularis*.

EXAMPLE 4

(4-1) Cloning of Soybean Endo-XG Transferase Gene and Determination of DNA Sequence Thereof:

The cDNA of about 1.1 kbp obtained in the above Example 2 was labeled with [α-$^{32}$P]dCTP by using a Random Primer DNA Labeling Kit and used as a probe for hybridization. A cDNA library prepared from soybean (*Glycine max*) tissue mRNA (manufactured by Clonetech) was subjected to plaque hybridization. As the result of an examination on 5×10⁴ plaques, three positive plaques were obtained. Then phages were isolated from these three plaques and DNAs were purified from the phages. These DNAs were cleaved with a restriction enzyme EcoRI and electrophoresed on an agarose gel to thereby see the length of the inserted cDNA segment. Thus the longest cDNA segment (about 1 kbp) could be obtained from among the above-mentioned three positive plaques. Then this cDNA segment was purified and subcloned into the EcoRI site of a vector pUC119. The plasmid thus obtained was named pSX102. The cDNA segment of about 1 kbp thus obtained was cleaved with several restriction enzymes and analyzed by agarose gel electrophoresis.

Figure 2:
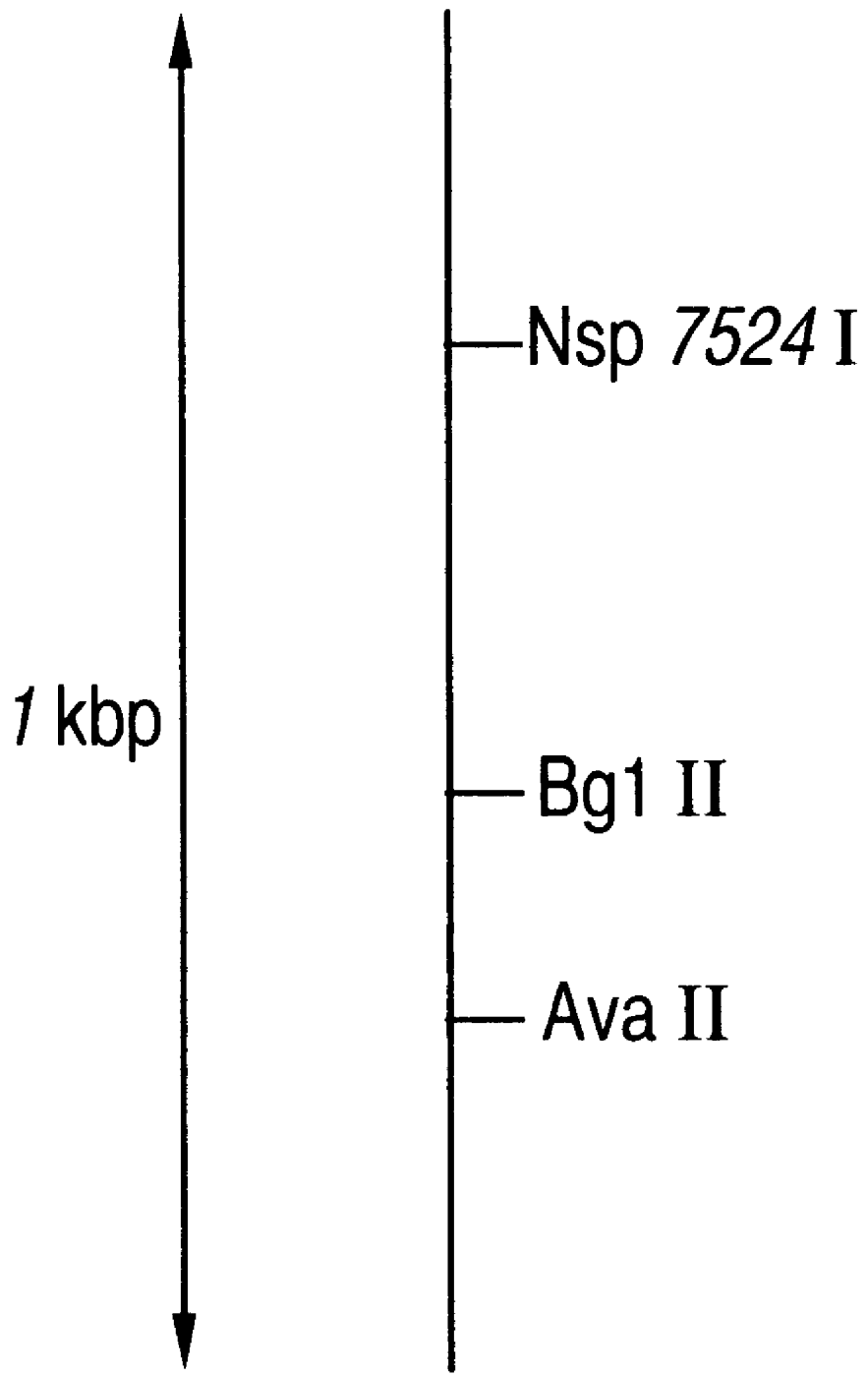
[FIG. 2]

FIG. 2 shows the result. Namely, FIG. 2 is a FIGURE showing a restriction enzyme map of the cDNA segment of about 1 kbp.

By using the plasmid pSX102, an *Escherichia coli* JM109 strain was transformed. The transformant thus obtained was named *Escherichia coli* JM109/pSX102 and deposited at the Fermentation Research Institute of the Agency of Industrial Science and Technology, Japan, under the accession number of FERM BP-4226.

The plasmid pSX102 was cleaved with restriction enzymes XbaI and SphI. By using the cDNA segment thus obtained, the DNA sequence of the cDNA segment of about 1 kbp was determined by the same method as the one employed in the above Example 3. A part of this sequence is represented by SEQ ID NO. 15 in the sequence listing.

(4-2) Cloning of *Arabidopsis thaliana* endo-XG transferase gene and determination of the DNA sequence thereof:

The cDNA of about 1.1 kbp obtained in the above Example 2 was labeled with [α-$^{32}$P]dCTP by using a Random Primer DNA Labeling Kit and used as a probe for hybridization. A cDNA library prepared from *Arabidopsis thaliana* tissue mRNA (manufactured by Clonetech) was subjected to plaque hybridization. As a result, about three positive plaques per 5×10⁴ plaques were obtained. Then phages were isolated from these three plaques and DNAs were purified from the phages. These DNAs were cleaved with a restriction enzyme EcoRI and electrophoresed on an agarose gel to thereby see the length of the inserted cDNA segment. Thus the longest cDNA segment (about 1.3 kbp) could be obtained from among the above-mentioned three positive plaques. Then this cDNA segment was purified and subcloned into the EcoRI site of a vector pUC119. The plasmid thus obtained was named pAX101. The cDNA segment of about 1.3 kbp thus obtained was cleaved with several restriction enzymes and analyzed by agarose gel electrophoresis.

Figure 3:
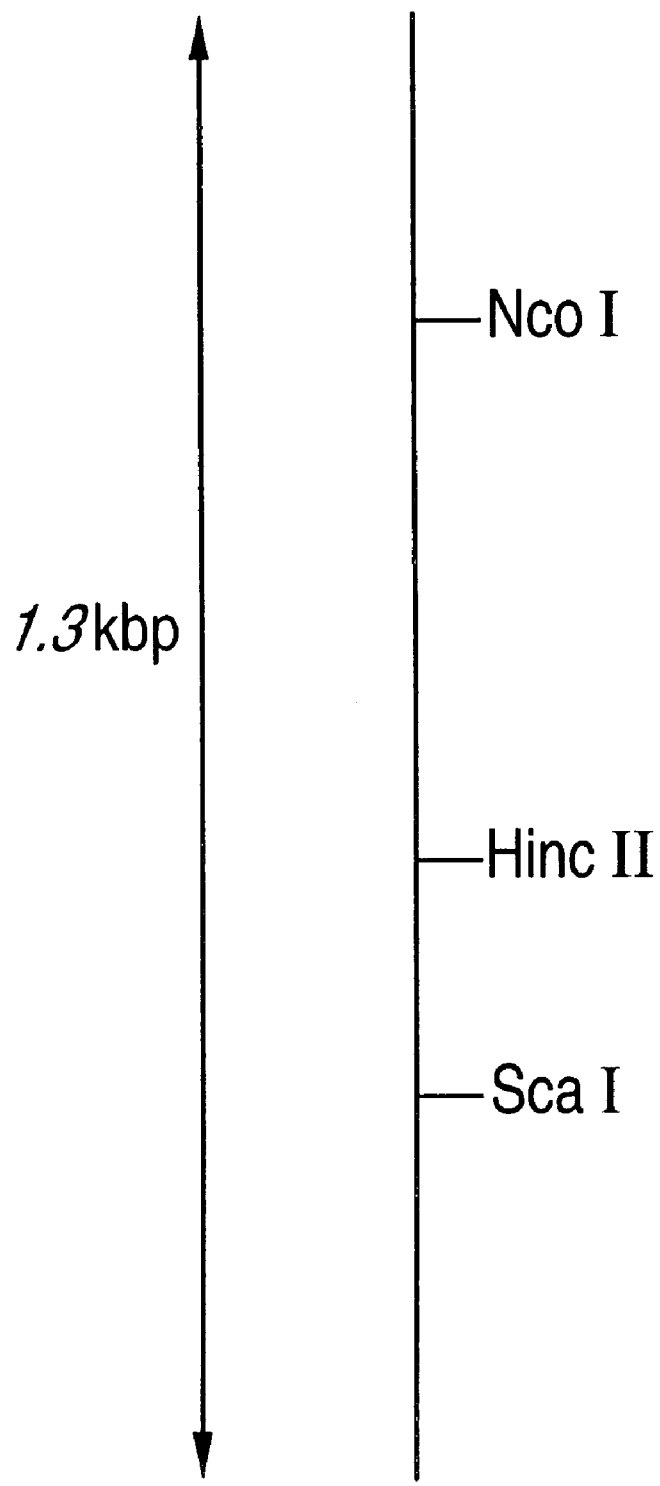
[FIG. 3]

FIG. 3 shows the result. Namely, FIG. 3 is a FIGURE showing a restriction enzyme map of the cDNA segment of about 1.3 kbp.

By using this plasmid pAX101, an *Escherichia coli* JM109 strain was transformed. The transformant thus obtained was named *Escherichia coli* JM109/pAX101.

The plasmid pAX101 was cleaved with restriction enzymes XbaI and SphI. By using the DNA segment thus obtained, the sequence of the DNA segment of about 1.3 kbp was determined by the same method as the one employed in the above Example 3. A part of this sequence is represented by SEQ ID NO. 7 in the sequence listing.

(4-3) Cloning of Tomato Endo-XG Transferase Gene and Determination of the Sequence Thereof:

Tomato (*Lycopersicon esculentum*) seeds (available from Watanabe Saishujo) were germinated and 10 μg of poly(A)+ RNA was extracted from the epicotyl tissue of these seeds by the same method as the one described in the above Example 2-(1). Then a cDNA library was prepared by using a λEXlox™ Introductory Cloning Kit (manufactured by Novagen). More specifically a cDNA was synthesized in accordance with a method described in Gene, 25, 263 (1983) and ligated into a vector λEXLX [Palazzolo et al. Gene, 88, 25–36 (1990)] by using an EcoRI linker and a HindIII linker contained in this kit, thus giving the target cDNA library.

The cDNA of about 1.1 kbp obtained in the above Example 2 was labeled with [α-$^{32}$P ]dCTP by using a Random Primer DNA Labeling Kit and used as a probe for hybridization. Then the cDNA library prepared above was subjected to plaque hybridization. As a result, about two positive plaques per 1×10$^5$ plaques were obtained. These two plaques were then treated by the above-mentioned method of Palazzolo et al. and thus a segment containing a cDNA was obtained as a plasmid from a λ phage DNA. This DNA was cleaved with restriction enzymes EcoRI and HindIII and electrophoresed on an agarose gel to thereby confirm the length of the cDNAs. Thus the length of the longer cDNA segment (about 1.2 kbp) between these two positive plaques could be identified. Then this cDNA segment was purified and the protruding terminus was blunted with the use of T4 DNA Polymerase (manufactured by Takara Shuzo Co., Ltd.). Then it was subcloned into the HincII site of a vector pUC118. The plasmid thus obtained was named pTX201. The DNA segment of about 1.2 kbp thus obtained was cleaved with several restriction enzymes and analyzed by agarose gel electrophoresis.

Figure 4:
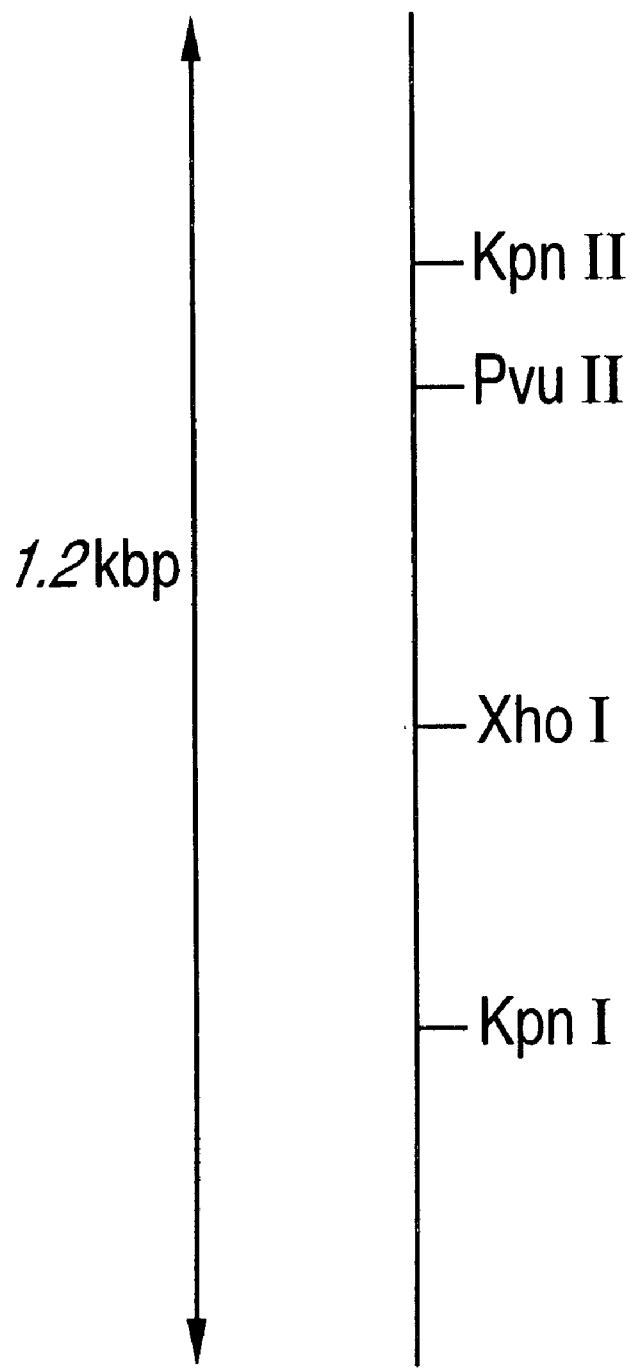
[FIG. 4]

FIG. 4 shows the result. Namely, FIG. 4 is a FIGURE showing a restriction enzyme map of the DNA segment of about 1.2 kbp.

The plasmid pTX201 was cleaved with restriction enzymes BamHI and SacI. By using the DNA segment thus obtained, the sequence of the DNA segment of about 1.2 kbp was determined by the same method as the one employed in the above Example 3. A part of this sequence is represented by SEQ ID NO. 18 in the sequence listing.

(4-4) Cloning of Wheat Endo-XG Transferase Gene and Determination of the Sequence Thereof:

The cDNA of about 1.1 kbp obtained in the above Example 2 was labeled with [α-$^{32}$P ]dCTP by using a Random Primer DNA Labeling Kit and used as a probe for hybridization. A cDNA library prepared from wheat (*Triticum aestrivum*) tissue mRNA (manufactured by Clonetech) was subjected to plaque hybridization. As a result, one positive plaque per 1×10$^5$ plaques was obtained. Then a phage was isolated from the plaque and DNA was purified from the phage. This DNA was cleaved with a restriction enzyme EcoRI and electrophoresed on an agarose gel to thereby see the length of the inserted cDNA segment. Thus a cDNA segment of about 0.9 kbp could be identified. This cDNA segment was purified and subcloned into the EcoRI site of a vector pUC119. The plasmid thus obtained was named pWX101. The DNA segment of about 0.9 kbp thus obtained was cleaved with several restriction enzymes and analyzed by agarose gel electrophoresis.

Figure 5:
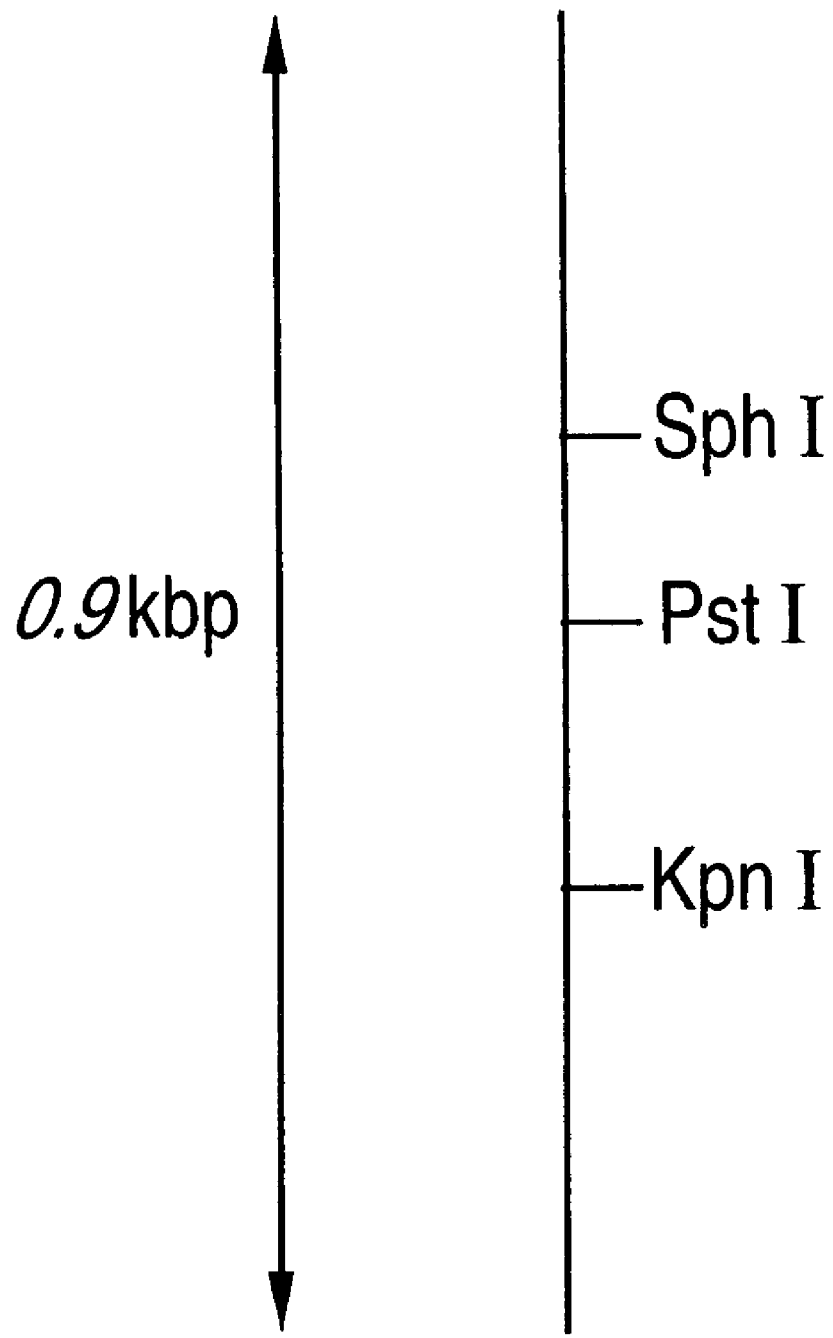
[FIG. 5]
Figure 6:
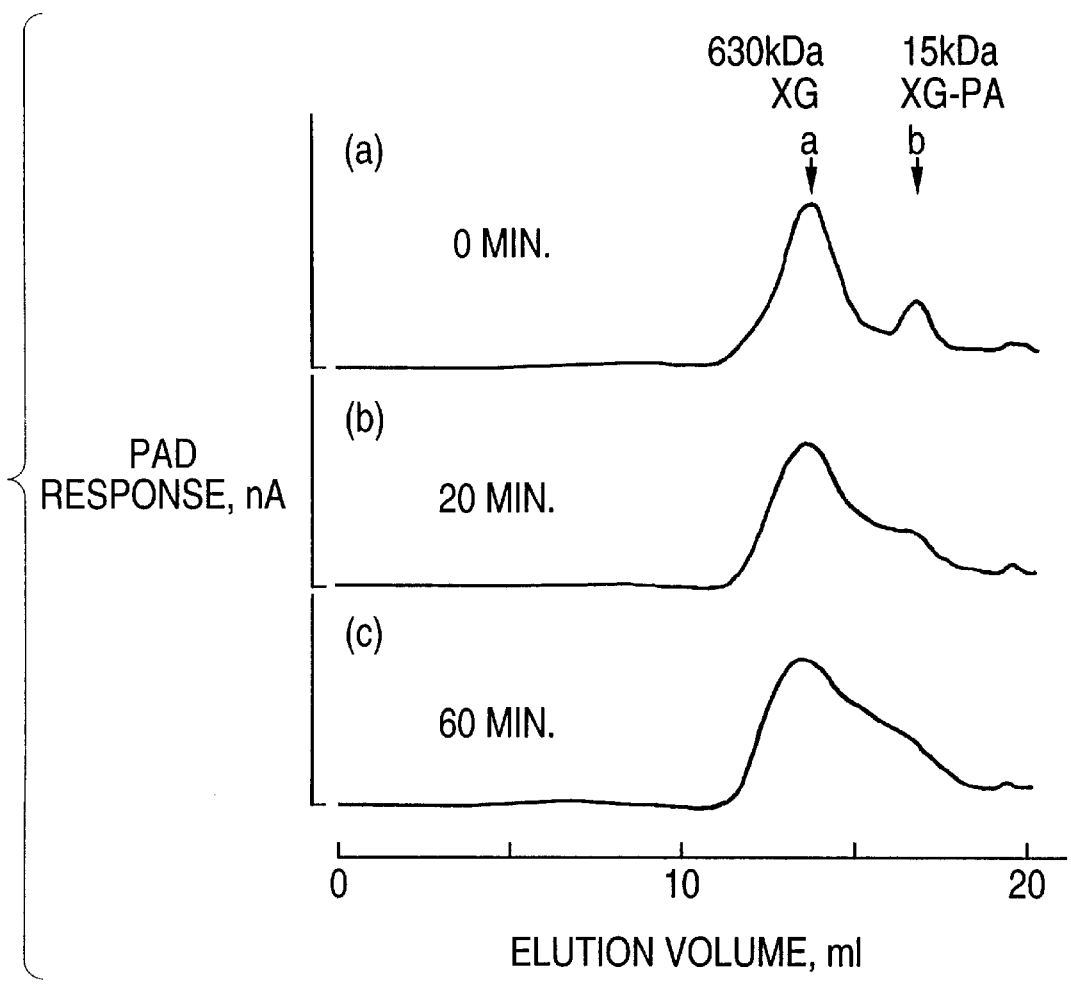
[FIG. 6]
Figure 7:
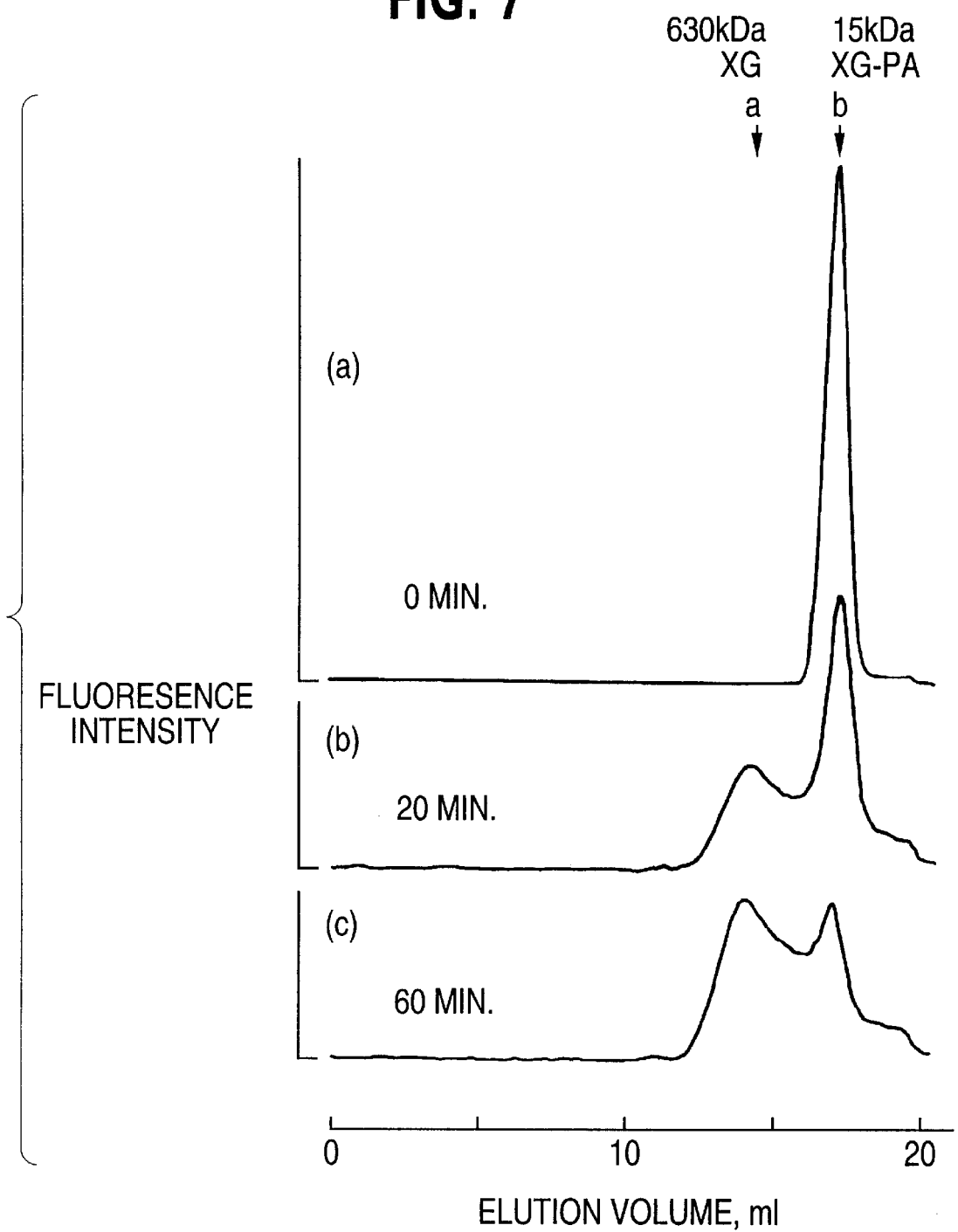
[FIG. 7]

FIG. 5 shows the result. Namely, FIG. 5 is a Figure showing a restriction enzyme map of the DNA segment of about 0.9 kbp.

By using this plasmid pWX101, an *Escherichia coli* JM109 strain was transformed. The transformant thus obtained was named *Escherichia coli* JM109/pWX101 and deposited at the Fermentation Research Institute of the Agency of Industrial Science and Technology, Japan, under the accession number of FERM BP-4225.

The plasmid pWX101 was cleaved with restriction enzymes XbaI and Sse8387I. By using the DNA segment thus obtained, the sequence of the DNA segment of about 0.9 kbp was determined by the same method as the one employed in the above Example 3. A part of this sequence is represented by SEQ ID NO. 19 in the sequence listing.

(4-5) Cloning of Maize Endo-XG Transferase Gene and Determination of the Sequence Thereof:

Maize (*Zea mays*) seeds (available from Snow Brand Seed Co., Ltd., Japan) were germinated and 10 μg of poly(A)+RNA was extracted from the epicotyl tissue of these seeds by the same method as the one described in the above Example 2-(1). Then a cDNA library was prepared by using a λEXlox™ Introductory Cloning Kit. More specifically a cDNA was synthesized in accordance with a method described in Gene, 25, 263 (1983) and ligated into a vector λEXLX by using an EcoRI linker and a HindIII linker contained in this kit, thus giving the cDNA library.

The cDNA of about 1.2 kbp obtained in the above Example 2 was labeled with [α-$^{32}$P]dCTP by using a Random Primer DNA Labeling Kit and used as a probe for hybridization. Then the cDNA library prepared above was subjected to plaque hybridization. As a result, one positive plaque per 1×10$^4$ plaques were obtained. The positive plaque was then treated by the above-mentioned method of Palazzolo et al. and thus a segment containing a cDNA was obtained as a plasmid from a λ phage DNA. This DNA was cleaved with restriction enzymes EcoRI and HindIII and electrophoresed on an agarose gel to thereby see the length of the DNA segment. Thus the length of the cDNA segment (about 1.2 kbp) could be confirmed. The plasmid thus obtained was named pCX101. The DNA segment of about 1.2 kbp thus obtained was cleaved with several restriction enzymes and analyzed by agarose gel electrophoresis.

Figure 15:
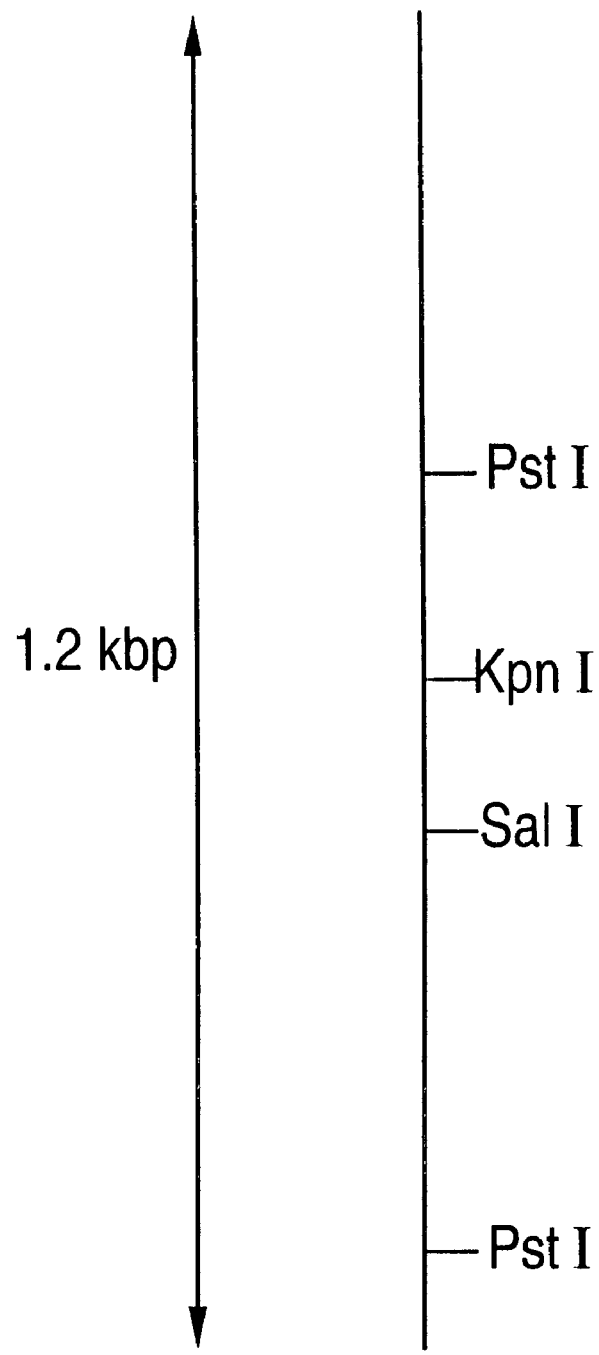
[FIG. 15]

FIG. 15 shows the result. Namely, FIG. 15 is a Figure showing a restriction enzyme map of the DNA segment of about 1.2 kbp.

(4-6) Cloning of Rice Endo-XG Transferase Gene and Determination of the Sequence Thereof:

Rice (*Oryza sativa*) seeds (provided by Dr. Kazuhiko Nishitani, Kagoshima Univ., Japan) were germinated and 10 μg of poly(A)+RNA was extracted from the epicotyl tissue of these seeds by the same method as the one described in the above Example 2-(1). Then a cDNA library was prepared by using a λEXlox™ Introductory Cloning Kit. More specifically a cDNA was synthesized in accordance with a method described in Gene, 25, 263 (1983) and ligated into a vector λEXLX by using an EcoRI linker and a HindIII linker contained in this kit, thus giving the target cDNA library.

The cDNA of about 1.1 kbp obtained in the above Example 2 was labeled with [α-$^{32}$P dCTP by using a Random Primer DNA Labeling Kit and used as a probe for hybridization. Then the cDNA library prepared above was subjected to plaque hybridization. As a result, one positive plaques per 1×10$^4$ plaques was obtained. The plaque was then treated by the above-mentioned method of Palazzolo et al. and thus a segment containing a cDNA was obtained as a plasmid from a λ phage DNA. This DNA was cleaved with restriction enzymes EcoRI and HindIII and electrophoresed on an agarose gel to thereby see the length of the DNA segment. Thus the length of the cDNA segment (about 1.1 kbp) could be confirmed. The plasmid thus obtained was named pRX102. The DNA segment of about 1.1 kbp thus obtained was cleaved with several restriction enzymes and analyzed by agarose gel electrophoresis.

Figure 16:
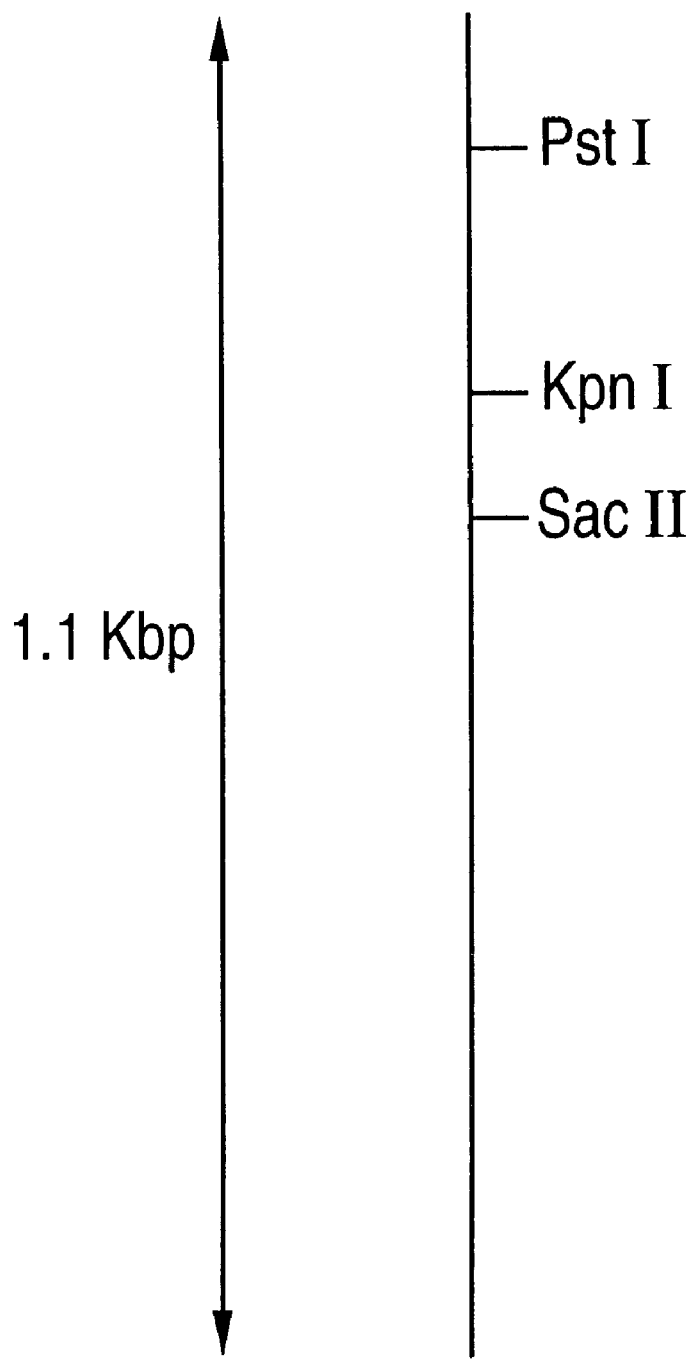
[FIG. 16]

FIG. 16 shows the result. Namely, FIG. 16 is a Figure showing a restriction enzyme map of the DNA segment of about 1.1 kbp.

By using this plasmid pRX102, an *Escherichia coli* JM109 strain was transformed. The transformant thus obtained was named *Escherichia coli* JM109/pRX102 and deposited at the Fermentation Research Institute of the Agency of Industrial Science and Technology, Japan, under the accession number of FERM BP-4221.

EXAMPLE 5

Expression of Endo-XG Transferase Gene 5-1 (Construction of expression plasmid pVX110)

Figure 14:
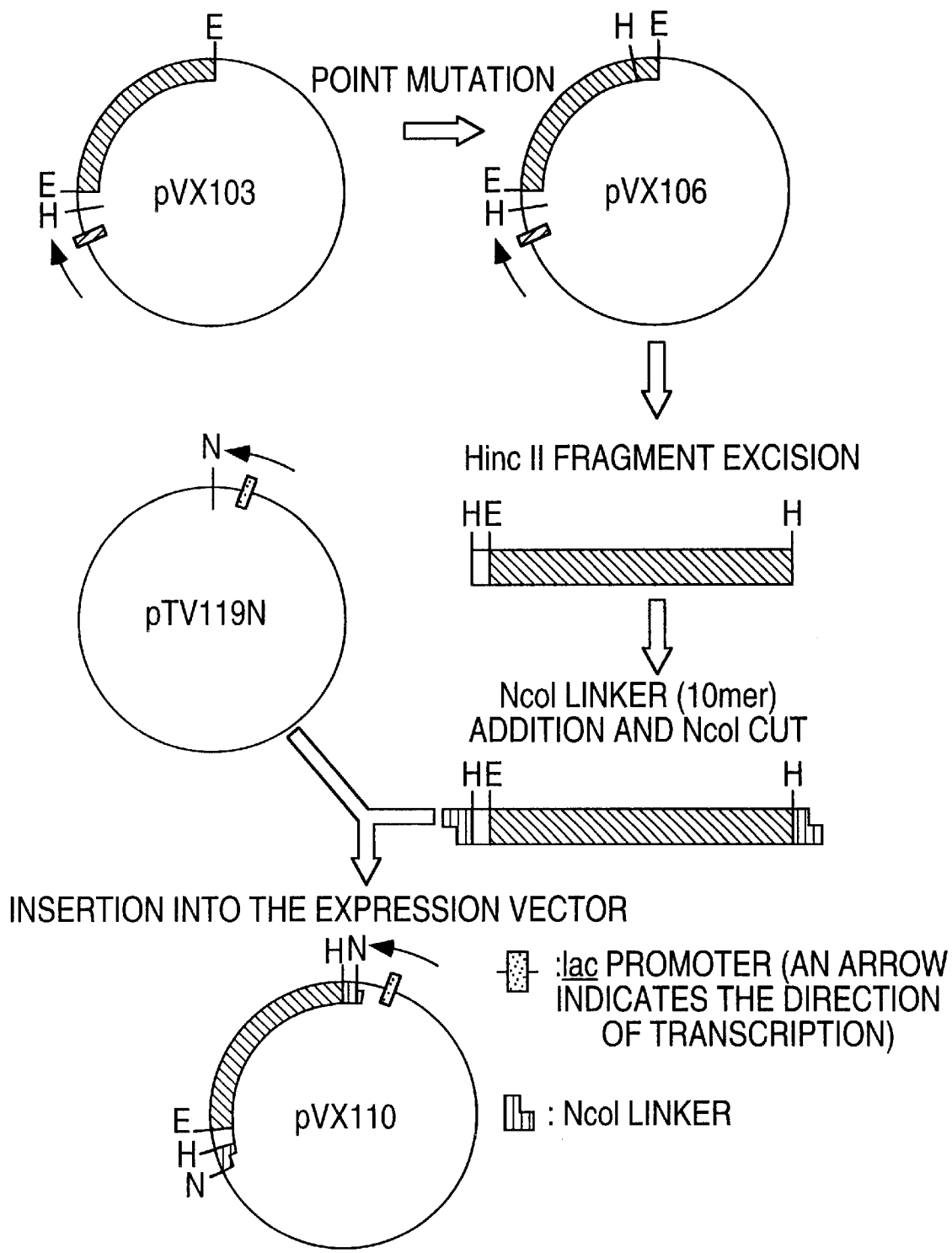
[FIG. 14]

Starting with the plasmid pVX103 obtained in the above Example 2, C of the base No. 58 in SEQ ID NO. 15 of the sequence listing was converted into T by Kunkel's method with the use of Mutan-K™. The plasmid thus constructed, which had a recognition site of a restriction enzyme HincII in the base Nos.57 to 62, was named pVX106. This pVX106 was cleaved with HincII at the recognition site of HincII prepared by the above procedure and at the recognition site of HincII in the multicloning site to thereby excise a segment of about 1.1 kbp. To this segment was added a decameric NcoI linker by using a Ligation Kit, followed by digestion with NcoI. Then a cDNA segment of about 1.1 kbp was purified by agarose gel electrophoresis and this segment was inserted into the NcoI site of a plasmid pTV119N. Since the segment thus inserted contained cleaving sites of PvuII at asymmetric positions, the direction of the inserted segment was confirmed based on the size of the PvuII-digested products. Thus the plasmid having the above-mentioned segment inserted thereinto in such a direction as to form mRNA of the gene coding for endo-XG transferase through transcription by lac promoter was named pVX110. FIG. 14 shows a process for constructing the plasmid pVX110. An *Escherichia coli* JM109 strain was transformed with pVX110 and the transformant thus obtained was named *Escherichia coli* JM109/pVX110.

5-2 (Expression of endo-XG transferase in *Escherichia coli*)

The *Escherichia coli* JM109/pVX110 obtained in the above 5-1 was suspended in 50 ml of an L-broth containing 100 µg/ml of ampicillin and incubated therein under shaking at 37° C. When the turbidity (O.D.660) after the incubation reached 0.3, IPTG was added to the culture so as to give a final concentration of 2 mM. After adding IPTG, the incubation was continued under shaking at 37° C. for 8 hours. After the completion of the incubation, 1 ml of cell suspension with an O.D. 660 value of 0.1 were collected and subjected to SDS-polyacrylamide gel electrophoresis (SDS-PAGE). An *Escherichia coli* JM109 strain which had been transformed by using an expression vector pTV119 alone was incubated under the same conditions as those employed above and then similarly subjected to SDS-PAGE as a control. After the completion of the electrophoresis, the gel was stained with Coomassie Brilliant Blue (CBB; manufactured by Nacalai Tesque, Inc.) and then destained with 7% acetic acid and 25% methanol solutions. As a result, *Escherichia coli* JM109/pVX110 showed the target band of a molecular weight of about 31 kDa and the expression of the endo-XG transferase was thus confirmed.

5-3 (Purification of endo-XG transferase)

*Escherichia coli* JM109/pVX110 was suspended in 200 ml of an L-broth containing 100 µg/ml of ampicillin and then incubated by the same method as the one described in the above 5-2. After the completion of the incubation, cells were collected by centrifuging the culture broth and suspended in 10 ml of a Tris-HCl buffer solution (pH 7.5). After grinding the cells by ultrasonication, the suspension was centrifuged to thereby divide into a supernatant fraction and a precipitate fraction. The precipitate fraction was suspended in 10 ml of distilled water. 2.5 µl portions of the supernatant and the precipitate were subjected to SDS-PAGE by the same method as the one described in the above 5-2. As a result, it was confirmed that the target protein was contained in the precipitate fraction. The suspension was then centrifuged again and 10 mg of the precipitate fraction thus obtained was dissolved in a buffer solution (pH 7.5) containing 7 M urea, 50 mM dithiothreitol (DTT) and 20 mM Tris-HCl and dialyzed against 2 l of an outer solution containing 20 mM Tris-HCl (pH 7.5) and 1 mM EDTA overnight. The inner-solution of the dialysis was concentrated with an ultrafiltration Membrane (manufactured by Amicon) and twice as much 100%-saturated aqueous solution of ammonium sulfate was added thereto so as to give a final concentration of 66%. After centrifuging at 15,000 rpm for 10 minutes, the protein thus precipitated was collected. This protein was dissolved in 750 µl of an aqueous solution of 20 mM Tris-HCl and 150 ml NaCl. A 150 µl portion of the obtained solution was poured into HPLC provided with a TSK Gel 2000SW (7.6×300 mm) which had been equilibrated with an aqueous solution of 20 mM Tris-HCl and 150 ml NaCl. Then the eluate was fractionated at a flow rate of 0.5 ml/min at intervals of 2 minutes and the absorbance of each fraction at 280 nm was measured to thereby confirm the position of elution of the protein. After the completion of gel filtration, the endo-XG transferase activity of each fraction was determined by using XG of a molecular weight of 50 kDa and a pyridylamino XG heptamer as substrates. As a result, an endo-XG transferase activity was detected from a fraction of a molecular weight of about 31 kDa.

EXAMPLE 6

Preparation of Arabidopsis Thaliana Transformant 6-1: Construction of Plasmids pAX301 and pAX302

Based on the sequence of a gene coding for endo-XG transferase of *Arabidopsis thaliana* represented by SEQ ID No. 17 in the sequence listing, four primers ATX-AS, ATS-AS, ATX-S, and ATS-S, represented respectively by SEQ ID Nos. 20, 21, 22, and 23 in the sequence listing, were designed and synthesized. The primers ATS-AS and ATX-S are ones wherein a cleaving site of a restriction enzyme SacI and XbaI is added, respectively, to the 5'-side of a sequence corresponding to the base Nos. 40 to 56 in SEQ ID No. 17 in the sequence listing in the direction of 5'→3', while the primers ATX-AS and ATS-S are ones wherein a cleaving site of a restriction enzyme XbaI and SacI is added, respectively, to the 5' side of a sequence corresponding to the base Nos. 1007 to 1023 in the direction of 3'→5'.

About 1 ng (1 µl) of the cDNA obtained in the above Example 4-(2) was introduced into a 0.5 ml tube as a template. To this tube were added 10 µl of 10×PCR buffer solution contained in a Gene Amp™ Kit, 16 µl of 1.25 mM dNTP mixture, 2.5 U of Ampli Taq™ DNA Polymerase, 20 pmol of the primers ATX-AS and ATS-AS, and sterilized distilled water in such an amount as to adjust the total volume to 100 µl. After further adding mineral oil, the mixture was subjected to PCR. The reaction was effected by repeating a cycle (94° C. for 1 minute, 55° C. for 1 minute, and 72° C. for 2 minutes) 35 times and then maintaining at 72° C. for 7 minutes. Next, PCR was carried out in the same manner with the use of the primers ATX-S and ATS-S. After the completion of the reaction, the reaction mixture was subjected to agarose gel electrophoresis. Thus it was confirmed that cDNAs of about 1 kbp were specifically amplified. Each of these cDNAs was cleaved with XbaI and SacI, purified and then subcloned into a site between the restriction enzyme XbaI site and the SacI site of a binary vector pBI-H1-35S-IG.

A plasmid having a DNA segment, which had been amplified by using a pair of the primers ATS-AS and ATX-AS, inserted thereinto was named pAX301, while another plasmid having a DNA segment, which had been amplified by using a pair of primers ATX-S and ATS-S, inserted thereinto was named pAX302.

By using this plasmid pAX301, an *Escherichia coli* JM109 strain was transformed. The transformant thus obtained was named *Escherichia coli* JM109/pAX301 and deposited at the Fermentation Research Institute of the Agency of Industrial Science and Technology, Japan, under the accession number of FERM BP-4222.

6-2: Introduction of pAX301 and pAX302 into Agrobacterium

By using 20 ng portions of the plasmids pAX301 and pAX302 obtained in the above 6-1, an *Agrobacterium tumefaciens* LBA4404 strain was transformed by the electroporation method [Shokubutsu Saibo Kogaku (Plant Cell Engineering), vol. 4, 193–203, Shujunsha (1992)].

As a result, transformants were obtained at an efficiency of $1 \times 10^7$ per microgram of the plasmid DNA. These transformants were purified in an LB-Km-Hg medium (10 g of bactotriptone, 5 g of yeast extract, 5 g of NaCl, 50 mg of kanamycin, 4,600 U of hygromycin, each per liter, pH 7.5). The strains transformed with pAX301 and pAX302 were respectively named LBA4404/pAX301 and LBA4404/pAX302. In a control test, an *Agrobacterium tumefaciens* LBA4404 strain was similarly transformed with the use of a binary vector pBI-H1-35S-IG alone. The transformant thus obtained was named LBA4404/pBI-H1-35S-IG.

6-3: Preparation of Plant Transformant 6-3-(1): Cultivation of sterile *Arabidopsis thaliana*

Several tens of grains of *Arabidopsis thaliana* Wassilewskija strain (hereinafter referred to simply as WS) seeds [obtained from Arabidopsis Information Service, J. W. Goethe Univ., A. R. Kranz, Frankfurt, Germany] were introduced into a 1.5 ml tube and immersed in 1 ml of 70% ethanol for 2 minutes. Subsequently, these seeds were immersed in a sterilizing solution (5% of sodium hypochlorite, 0.02% of Triton X-100) for 5 minutes. After washing with sterilized water 5 times, they were placed on a GM plate [4.6 g of Murashige-skoog inorganic salts (manufactured by Wako Pure Chemical Industries, Ltd.), 10 g of sucrose, 1 ml of 1000×vitamin stock solution (manufactured by Sigma), 10 ml of 5% MES-KOH (pH 5.7), and 5 g of gellan gum (manufactured by Wako Pure Chemical Industries, Ltd.), each per liter]. This plate was cold-treated by allowing to stand at 4° C. for 2 days and then incubated in a plant incubator (Model CFH-300, manufactured by Tomy Seiko Co., Ltd.) at 22° C. at a light intensity of 6000 lux under long-day conditions (lighting period: 16 hours, dark period: 8 hours) for 20 days.

6-3-(2) Infection with Agrobacterium

The roots of several portions of the WS plants, which had been incubated for 20 days in the above 6-3(1), were cut in a uniform length of about 1.5 cm with a scalpel and placed on a CIM plate. Then the root explants were incubated at a light intensity of 3000 lux (lighting period: 16 hours, dark period: 8 hours) for 3 days to thereby callus the root explants.

Separately, the strains LBA4404/pAX301, LBA4404/pAX302, and LBA4404/pBI-H1-35S-IG obtained in the above 6-2 were incubated in an LB-Km-Hg liquid medium at 28° C. for 2 days and diluted 3-fold with an MS diluting solution (6.4 g/l of Murashige-skoog inorganic salts, pH 6.2). One-ml portions of the solution thus obtained were pipetted into tubes and the callused root explants were immersed therein for 10 minutes. Then these explants were placed on a twoply filter paper to thereby eliminate excessive moisture and placed on a fresh CIM plate to conduct incubation together under the same conditions for 2 days.

6-3-(3) Sterilization

Explants on which each strain had grown to such a level as being observable were transported into a sterilizing solution (prepared by adding Claforan (manufactured by Hoechst) to a diluted MS solution in such an amount as to give a final concentration of 200 μg/ml] and washed by slowly shaking therein for 30 minutes. After repeating this operation 5 times, the moisture was eliminated on a sterile filter paper and the explants were placed on an SIMC plate to conduct incubation at a light intensity of 6000 lux (lighting period: 16 hours, dark period: 8 hours) for 2 days.

6-3-(4): Selection of transformed plants

The explants incubated in the above 6-3-(3) were transplanted into an SIMCS plate (prepared by adding hygromycin B to an SIMC plate in such an amount as to give a final concentration of 4.6 U/ml) and incubated under the same conditions as those employed in the above 6-3-(3). Then they were transplanted into a fresh SIMCS plate at intervals of 1 week. Transformed explants continuously grew and formed convex calluses, while untransformed ones turned brown. After 2 weeks, the calluses in the transformants turned green and leaves were formed after about 1 month. Subsequently, these leaves turned rosetted.

6-3-(5) Regeneration of Transformed Plants

The base of a plant having rosetted leaves was cut with a scalpel in such a manner-that no callus was contained therein and transferred into an RIM plate. After 8 to 10 days, explants having several roots of about 2 cm were fix-planted into a Rock Fiber Minipot immersed in an inorganic salt medium [5 mM $KNO_3$, 2.5 mM potassium phosphate buffer solution (pH 5.5), 2 mM $MgSO_4$, 2 mM $Ca(NO_3)_2$, 50 μM Fe-EDTA, 1000×Micronutrients (70 mM $H_3BO_4$, 14 mM $MnCl_2$, 0.5 mM $CuSO_4$, 1 mM $ZnSO_4$, 0.2 mM $NaMoO_4$, 10 mM NaCl, 0.01 mM $CoCl_2$) 1 ml/l] with a pair of tweezers and incubated therein. After flowering and podding, the plants were transplanted into a soil prepared by mixing perlite with vermiculite (manufactured by TES) at a ratio of 1:1 and immersing in an inorganic salt medium. After about 1 month, approximately 1,000 seeds were obtained per plant. These seeds are referred to as $T_2$ seeds hereinafter.

6-3-(6) Acquisition of Antibiotic-resistant Plant

About 100 grains of the $T_2$ seeds were sterilized by the same method as the one employed in the above 3-(1) and sowed on an MSH plate. Thus, hygromycin B-resistant plants germinated at a ratio of about 3:1.

6-4: DNA Extraction and Southern Hybridization

The $T_2$ seeds germinated in the above 6-3-(6) were transplanted into a Rock Fiber Minipot immersed in an in organic salt medium with a pair of tweezers and incubated at a light intensity of 6000 lux (lighting period: 16 hours, dark period: 8 hours) at a temperature of 22° C. After 2 weeks, the above-ground part was cut with a scalpel and then immediately frozen with liquid nitrogen. Then it was ground with a pestle in a mortar while adding liquid nitrogen to thereby give a powder. Immediately after the evaporation of the liquid nitrogen, 3 ml/g of a DNA extractant buffer solution [200 mM Tris-HCl (pH 8.0), 100 mM EDTA-2Na, 1% sodium N-lauroyl sarcosinate, 100 µg/ml of Proteines K (manufactured by Boehringer)] was added to the powder, which was transferred into a tube which had been preheated to 60° C. and stirred. After maintaining at 60° C. for 1 hour, the mixture was centrifuged and the supernatant thus obtained was transferred into a new tube. Then it was extracted with a mixture of phenol, chloroform and isoamyl alcohol (25:24:1) thrice and precipitated from ethanol. The precipitate was dissolved in a TE buffer solution [10 mM Tris-HCl (pH 8.0), 1 mM EDTA]. Thus 12 µg of a genome DNA was obtained from about 1.7 g of each plant. 1 µg portions of DNA were cleaved respectively with restriction enzymes HindIII and PstI, electrophoresed on a 1% agarose gel and then subjected to Southern hybridization.

Separately, seeds of an untransformed WS plant were germinated and a DNA was similarly extracted from the obtained plants. After digesting with restriction enzymes HindIII and PstI, the DNA was electrophoresed on a 1% agarose gel and then subjected to Southern hybridization. A probe for hybridization was constructed by labeling a DNA segment of about 1 kbp amplified and purified in the above Example 6-1, with ($\alpha$-$^{32}$P)dCTP by using a Random Primer DNA Labeling Kit (manufactured by Takara Shuzo Co., Ltd.) by the method as will be described hereinafter.

Namely, 25 ng of the above-mentioned DNA segment and 2 µl of a random primer were put into a tube and the total volume was adjusted to 5 µl by adding distilled water thereto. After heating at 95° C. for 3 minutes, the mixture was quenched in ice-water. Then 2.5-µl portions of a 10-fold concentrated buffer solution and a dNTP mixture and 5 µl of labeled dCTP were added thereto and the total volume was adjusted to 24 µl by adding distilled water. After adding 1 µl of Klenow's fragment, the mixture was incubated at 37° C. for 3 hours. After inactivating the enzyme, the mixture was heated at 95° C. for 3 minutes and then quenched in ice to thereby thermally denature the mixture. Then the whole mixture was used in hybridization.

The Southern hybridization was carried out in accordance with a method described in "Molecular Cloning a Laboratory Manual", ed. by Maniatis et al., chap. 9, pages 31–58, Cold Spring Harbor. More specifically, each DNA sample was electrophoresed on a 1% agarose gel, denatured with an alkali and Southern blotted on a nylon membrane (Hybond-N, manufactured by Amersham) overnight. Then the DNA was fixed by irradiating with an UV transilluminator (254 nm) for 5 minutes. The resulting membrane was then subjected to prehybridization in 5 ml of a prehybridization buffer solution (5×Denhardt's solution, 6×SSC, 0.1% SDS, 10 µg/ml salmon sperm DNA) at 50° C. for 2 hours. Then a probe was added thereto and hybridization was carried out at 50° C. overnight. After the completion of the hybridization, the membrane was washed with a washing solution containing 2×SSC and 0.1% SDS at room temperature for 10 minutes twice and then with the same washing solution at 50° C. for 30 minutes twice. The membrane was then dried and exposed to light in a cassette containing an X-ray film (manufactured by Kodak) at −80° C. overnight to thereby give an autoradiogram.

Signal patterns, detected by the Southern hybridization, of an untransformed WS strain (1), a transformant (2) having pAX301 introduced thereinto, a transformant (3) having pAX302 introduced thereinto and a transformant (4) having a vector pBI-H1-35S-IG alone introduced thereinto were compared with each other. As a result, specific signals at positions of about 1 kbp (in the case of samples cleaved with HindIII) and about 3 kbp (in the case of samples cleaved with PstI) were observed in both of the transformants (2) and (3) in addition to the endogenous signals common to (1) to (4). It was thus confirmed that a DNA coding for endo-XG transferase was integrated into both of (2) and (3). In the case of the samples cleaved with HindIII, furthermore, specific signals at positions of about 10 kbp and about 20 kbp were observed respectively in (2) and (3). In the transformant (4), a signal pattern similar to that of (1) was obtained.

6-5: RNA Extraction and Hybridization

By the same method as the one described in the above 6-4, the above-ground parts of 30 hygromycin Bresistant strains were cut and thus 1.8 goof a plant tissue was obtained. Then about 500 µg of an RNA was prepared by the same method as the one employed in the above Example 2-(1) except that the procedure with the use of Oligotex dT-30 was omitted. A probe for Northern hybridization was constructed by the method as will be described hereinafter. The 5'-end of the above-mentioned primer ATX-S was labeled with $^{32}$P by using a MEGALABEL™ kit(manufactured by Takara Shuzo Co., Ltd.) while the 5'-end of a primer ATS-S was labeled with biotin.

By using these two primers, PCR was effected under the same conditions as those employed in the above Example 6-1 with the use of the cDNA of about 1.3 kbp obtained in the above Example 4-(2) as a template. Then avidin beads (manufactured by Dynal) were added to the reaction mixture and the PCR product was collected. After thermally denaturing the PCR product, the avidin beads were collected. As a result, the DNA the 5'-end of which was labeled with $^{32}$P was liberated into the solution.

The DNA sequence was confirmed by the same method as the one described in the above Example 4 and thus a probe having a sense DNA sequence was obtained. Similarly, the above procedure was repeated by using a primer ATS-S the 5'-end of which was labeled with $^{32}$P and another primer ATX-S the 5'-end of which was labeled with biotin and thus a probe having an antisense DNA sequence was obtained.

The Northern hybridization was carried out by the following method described in "Molecular Cloning", chap. 7, pages 39–52 as cited above. Namely, the whole RNA extracted above was electrophoresed on a formaldehyde running agarose gel (1%), neutralized in a solution of ammonium acetate, and then Northern blotted onto a nylon membrane [Hybond-N] overnight. Then the RNA was fixed by irradiating with an UV transilluminator (254 nm) for 5 minutes. This membrane was then subjected to prehybridization in 20 ml of a prehybridization buffer solution (50% formaldehyde, 0.65 M NaCl, 0.1 M Na-Pipes (pH 6.8), 5×Denhardt's solution, 0.1% SDS, 5 mM EDTA, 100 µg/ml salmon sperm DNA) at 42° C. for 3 hours. Next, the membrane was subjected to hybridization in the 20 ml of the hybridization solution [50% formaldehyde, 0.65M NaCl, 0.1M Na-Pipes(pH6.8), 5×Denhardt's solution, 0.1% SDS, 5 mM EDTA, 100 µg/ml salmon sperm DNA] containing the $^{32}$P labeled probes prepared as described above, at 42° C. overnight. Then, the membrane was washed with a washing solution containing 2×SSC and 0.1% SDS at 50° C. for 10 minutes 4 times. The membrane was then dried and exposed to light in a cassette containing an X-ray film at −80° C. overnight to thereby give an autoradiogram.

When a probe having a sense DNA sequence was used, no signal was observed in the above-mentioned (1), (3) and (4) but the transformant (2) showed a band of about 1 kbp, which indicated that an antisense RNA of an endo-XG transferase gene was formed. When a probe having an antisense DNA sequence was used, on the other hand, bands of about 1 kbp were observed in all of (1) to (4). Among them, the band of (3) showed an intense signal compared with (1). On the contrary, (2) showed a less intense signal. Thus, it was found that the expression of the endo-XG transferase was enhanced at the transcription level by introducing pAX302 but suppressed at the transcription level by introducing pAX301.

EXAMPLE 7

Formation of Tobacco Transformant 7-1: Construction of Plasmids pTX301 and pTX302

Based on the sequence of a gene coding for endo-XG transferase of tomato represented by SEQ ID NO. 18 in the sequence listing, four primers TOMXSP, TOMXAP, TOMSAP, and TOMSSP represented respectively by SEQ ID Nos. 24, 25, 26, and 27 in the sequence listing were designed and synthesized. The primers TOMXSP and TOMSSP are ones wherein a cleaving site of a restriction enzyme XbaI and SacI is added, respectively, to the 5'-side of a sequence corresponding to the base Nos. 46 to 66 in SEQ ID NO. 18 in the sequence listing in the direction of 5'→3', while the primers TOMSAP and TOMXAP are ones wherein a cleaving site of a restriction enzyme SacI and XbaI is added, respectively, to the 5'-side of a sequence corresponding to the base Nos. 921 to 941 in the direction of 3'→5'.

About 1 ng (1 μl) of the cDNA obtained in the above Example 4-(3) was introduced into a 0.5 ml tube as a template. To this tube were added 10 μl of 10×PCR buffer solution contained in a Gene Amp™ Kit, 16 μl of a 1.25 mM dNTP mixture, 2.5 U of AmpliTaq™ DNA Polymerase, 1 μl portions of 0.1 μg/μl of the primers TOMXSP and TOMSAP, and sterilized distilled water in such an amount as to adjust the total volume to 100 μl. After further adding mineral oil, the mixture was subjected to PCR. The reaction was effected by repeating a cycle (94° C. for 30 seconds, 37° C. for 2 minutes, and 72° C. for 1 minute) 25 times. Next, PCR was carried out in the same manner with the use of the primers TOMSSP and TOMXAP. After the completion of the reaction, each reaction mixture was concentrated by ethanol precipitation, cleaved with XbaI and SacI, purified, and then subcloned into a site between the restriction enzyme XbaI site and the SalI site of a binary vector pBI-H1-35S-IG.

A plasmid having a DNA segment, which had been amplified by using a pair of the primers TOMXSP and TOMSAP, inserted thereinto was named pTX301, while another plasmid having a DNA segment, which had been amplified by using a pair of primers TOMSSP and TOMXAP, inserted thereinto was named pTX302.

By using this plasmid pTX301, an *Escherichia coli* JM109 strain was transformed. The transformant thus obtained was named *Escherichia coli* JM109/pTX301 and deposited at the Fermentation Research Institute of the Agency of Industrial Science and Technology, Japan, under the accession number of FERM BP-4223. On the other hand, by using this plasmid pTX302, an *Escherichia coli* JM109 strain was transformed. The transformant thus obtained was named *Escherichia coli* JM109/pTX302 and deposited at the Fermentation Research Institute of the Agency of Industrial Science and Technology, Japan, under the accession number of FERM BP-4224.

7-2: Introduction of pTX301 and pTX302 into Agrobacterium

By using 20 ng portions of the plasmids pTX301 and pTX302, an *Agrobacterium tumefaciens* LBA4404 strain was transformed by the same method as the one employed in the above Example 6-2. Separately, an *Agrobacterium tumefaciens* LBA4404 strain was transformed by using pBI-H1-35S-IG alone as a control. After purifying, these transformants were named respectively LBA4404/pTX301, LBA4404/pTX302, and LBA4404/pBI-H1-35S-IG.

7-3: Preparation of Plant Transformant

The introduction into tobacco was effected by the leaf disk method. Namely, leaves of a tobacco SR-1 strain, which had been sterilely grown, were taken and cut into leaf disks (about 1 cm$^2$) containing veining with a sterilized scalpel. 2001 portions of the LBA4404/pTX301, LBA4404/pTX302, and LBA4404/pBI-H1-35S-IG strains obtained in the above Example 7-2, which had been incubated in an LB medium overnight, were added to a sterilized Petri dish containing 5 ml of a Murashige-skoog (MS) medium and the leaf disks were transferred thereto with a pair of sterilized tweezers. After mixing by rotating the Petri dish, the Petri dish was sealed with paraffin paper to thereby prevent the evaporation of moisture and allowed to stand in the dark at 28° C. for 3 days to thereby effect co-incubation. Next, the leaf disks were transferred into another Petri dish containing 20 ml of the MS medium and excessive Agrobacterium was washed away by rotating the Petri dish. After repeating this operation thrice and eliminating excessive moisture with a paper towel, the leaf disks were placed on a solid MS medium containing kanamycin, hygromycin, and carbenicillin and 0.2 μg/ml of 1-naphthaleneacetic acid and 1 μg/ml of benzyladenine as plant hormones in such a manner as to put the leaf upside down. Then the disks were incubated in a plant incubator (Model CFH-300, manufactured by Tomy Seiko Co., Ltd.) at 26° C. at a cycle of lighting period of 12 hours and dark period of 12 hours. After 4 weeks, the calluses were cut off as much as possible with a razor. Then the corms thus appearing was cut from the disk and put into an MS medium containing kanamycin, hygromycin, and carbenicillin and incubated therein under the same conditions. After 2 weeks, the plants thus rooting was transplanted into a soil comprising peat-moss and vermiculite (3:2) and grown in a plant incubator.

7-4: DNA Extraction and Southern Hybridization

Leaf tissues of the plants grown in the above 7-3 were cut with a scalpel and a genome DNA was prepared therefrom by the same method as the one described in the above 6-4. 10 μg of the genome DNA was completely digested with a restriction enzyme PstI, electrophoresed on a 1% agarose gel, and then subjected to Southern hybridization as in above-mentioned 6-4. As a probe for the hybridization, one prepared by labeling a DNA segment of about 930 bp, which had been amplified and purified in the above Example 7-1, with $^{32}$P by the same method as the one described in the above 6-4 was employed.

As a result, the tobacco plants having pTX301 and pTX302 introduced thereinto showed a band in addition to those seemingly assignable to tobacco endo-XG transferase, or a band of a high signal intensity which was clearly different from other bands, compared with the one having pBI-H1-35S-IG and the untransformed one. These results proved that a gene coding for tomato endo-XG transferase had been introduced into the tobacco plants having pTX301 and pTX302 introduced thereinto.

7-5: RNA Extraction and Northern Hybridization

Leaf tissues of the plants grown in the above 7-3 were cut with a scalpel and an RNA was prepared therefrom by the same method as the one described in the above 6-5. Then a probe for Northern hybridization was prepared by the same method as the one employed in the above 6-5. Namely, a probe having a sense DNA sequence was constructed by using TOMXSP, the 5'-end of which was labeled with $^{32}$P, and TOMSAP, the 5'-end of which was labeled with biotin, while another probe having an antisense DNA sequence was constructed by using TOMSAP, the 5'-end of which was labeled with $^{32}$P, and a primer TOMXSP, the 5'-end of which was labeled with biotin. Then Northern hybridization was effected by the same method as the one described in the above 6-5.

As a result, when the probe having the sense DNA sequence was used, the tobacco transformants having pBI-H1-35S-IG and pTX301 introduced thereinto and the untransformed one showed no band, while the one having pTX302 introduced thereinto showed a corresponding band. On the other hand, when the probe having the antisense DNA sequence was used, the tobacco plant having pBI-H1-35S-IG introduced thereinto and the untransformed one showed the corresponding bands while the one having pTX301 introduced thereinto showed a band of an elevated intensity. The tobacco plant having pTX302 introduced thereinto showed only a slight band. These results proved that a mRNA of the gene coding for the endo-XG transferase was increased, and as a result, the expression of the endogenous endo-XG transferase gene was enhanced by introducing pTX301. Moreover, it was confirmed that the antisense RNA of the gene coding for the endo-XG transferase was formed, thus the expression of the endogenous endo-XG transferase gene was suppressed by introducing pTX302.

[Effects of the Invention]

According to the present invention, an endo-XG transferase responsible for the transfer of XG molecules which is important in the growth mechanism of plant cell wall and a gene coding for said enzyme-are provided. Further, a method of cloning a gene coding for endo-XG transferase, a method of producing endo-XG transferase by using the gene and an antisense DNA and an antisense RNA of a gene coding for endo-XG transferase are also provided thereby. Furthermore, a method of controlling the expression of endo-XG transferase, a method of regulating the morphology of a plant and a method of transferring XG molecules are provided thereby.

What we claim is:

1. A method for inhibiting the expression of an endo-xyloglucan transferase in a plant which produces endo-xyloglucan transferase, said method comprising introducing into the plant a heterologous expression vector for forming an antisense RNA, wherein the heterologous expression vector comprises a DNA comprising the sequence shown in SEQ ID NO. 15 which codes for an endo-xyloglucan transferase in a 5'-3' direction, said DNA being operably linked in a reverse 3'–5' direction downstream of a promoter.

2. The method according to claim 1, wherein the DNA is obtained from *Vigna angularis*.

3. A method for inhibiting the expression of an endo-xyloglucan transferase in a plant which produces endo-xyloglucan transferase, said method comprising introducing into the plant a heterologous expression vector for forming an antisense RNA, wherein the heterologous expression vector comprises a DNA which codes for a protein in a 5'-3' direction having endo-xyloglucan transferase activity, wherein the complement of said DNA hybridizes with the sequence shown in SEQ ID NO. 15 under the following conditions:

solution: 5×Denhart's solution, 6×SSC, 0.1% SDS, 10 µg/ml salmon sperm DNA, hybridization: incubating at 50° C. overnight, said DNA being operably linked in a reverse 3'-5' direction downstream of a promoter.

4. The method according to claim 3, wherein the DNA is obtained from *Vigna angularis*.

5. A method for regulating the morphology of a plant, said method comprising introducing into the plant a heterologous expression vector for forming an antisense RNA, wherein the heterologous expression vector comprises a DNA comprising the sequence shown in SEQ ID NO. 15 which codes for an endo-xyloglucan transferase in a 5'-3' direction, said DNA being operably linked in a reverse 3'-5' direction downstream of a promoter, to thereby regulate the morphology of the plant by controlling the expression of an endo-xyloglucan transferase in the plant.

6. The method according to claim 5, wherein the DNA is obtained from *Vigna angularis*.

7. A method for regulating the morphology of a plant, said method comprising introducing into the plant a heterologous expression vector for forming an antisense RNA, wherein the heterologous expression vector comprises a DNA which codes for a protein in a 5'-3' direction having endo-xyloglucan transferase activity, wherein the complement of said DNA hybridizes with the sequence shown in SEQ ID NO. 15 under the following conditions:

solution: 5×Denhart's solution, 6×SSC, 0.1% SDS, 10 µg/ml salmon sperm DNA, hybridization: incubating at 50° C. overnight, said DNA being operably linked in a reverse 3'-5' direction downstream of a promoter, to thereby regulate the morphology of the plant by controlling the expression of an endo-xyloglucan transferase in the plant.

8. The method according to claim 7, wherein the DNA is obtained from *Vigna angularis*.

9. A plant having a heterologous expression vector for forming an antisense RNA introduced into the plant, wherein the heterologous expression vector comprises a DNA comprising the sequence shown in SEQ ID NO. 15 which codes for an endo-xyloglucan transferase in a 5'-3' direction, said DNA being operably linked in a reverse 3'-5' direction downstream of a promoter.

10. The plant according to claim 9, wherein the DNA is obtained from *Vigna angularis*.

11. A plant having a heterologous expression vector for forming an antisense RNA introduced into the plant, wherein the heterologous expression vector comprises a DNA which codes for a protein in a 5'-3' direction having endo-xyloglucan transferase activity, wherein the complement of said DNA hybridizes with the sequence shown in SEQ ID NO. 15 under the following conditions:

solution: 5×Denhart's solution, 6×SSC, 0.1% SDS, 10 μg/ml salmon sperm DNA, hybridization: incubating at 50° C. overnight, said DNA being operably linked in a reverse 3'-5' direction downstream of a promoter.

12. The plant according to claim 11, wherein the DNA is obtained from *Vigna angularis*.

13. A method for expressing an endo-xyloglucan transferase in a plant, said method comprising introducing into the plant a heterologous expression vector, wherein the heterologous expression vector comprises a DNA comprising the sequence shown in SEQ ID NO. 15 which codes for an endo-xyloglucan transferase in a 5'-3' direction, said DNA being operably linked in a 5'-3' direction downstream of a promoter.

14. The method according to claim 13, wherein the DNA is obtained from *Vigna angularis*.

15. A method for expressing an endo-xyloglucan transferase in a plant, said method comprising introducing into the plant a heterologous expression vector, wherein the heterologous expression vector comprises a DNA which codes for a protein in a 5'-3' direction having endo-xyloglucan transferase activity, wherein the complement of said DNA hybridizes with the sequence shown in SEQ ID NO. 15 under the following conditions:

solution: 5×Denhart's Solution, 6×SSC, 0.1% SDS, 10 μg/ml salmon sperm DNA, hybridization: incubating at 50° C. overnight, said DNA being operably linked in a 5'-3' direction downstream of a promoter.

16. The method according to claim 15, wherein the DNA is obtained from *Vigna angularis*.

17. A method for regulating the morphology of a plant, said method comprising introducing into the plant a heterologous expression vector, wherein the heterologous expression vector comprises a DNA comprising the sequence shown in SEQ ID NO. 15 which codes for an endo-xyloglucan transferase in a 5'-3' direction, said DNA being operably linked in a 5'-3' direction downstream of a promoter, to thereby regulate the morphology of the plant by expressing an endo-xyloglucan transferase in the plant.

18. The method according to claim 17, wherein the DNA is obtained from *Vigna angularis*.

19. A method for regulating the morphology of a plant, said method comprising introducing into the plant a heterologous expression vector, wherein the heterologous expression vector comprises a DNA which codes for a protein in a 5'-3' direction having endo-xyloglucan transferase activity, wherein the complement of said DNA hybridizes with the sequence shown in SEQ ID NO. 15 under the following conditions:

solution: 5×Denhart's solution, 6×SSC, 0.1% SDS, 10 μg/ml salmon sperm DNA, hybridization: incubating at 50° C. overnight, said DNA being operably linked in a 5'-3' direction downstream of a promoter, to thereby regulate the morphology of the plant by expressing an endo-xyloglucan transferase in the plant.

20. The method according to claim 19, wherein the DNA is obtained from *Vigna angularis*.

21. A plant having a heterologous expression vector introduced into the plant, wherein the heterologous expression vector comprises a DNA comprising the sequence shown in SEQ ID NO. 15 which codes for an endo-xyloglucan transferase in a 5'-3' direction, said DNA being operably linked in a 5'-3' direction downstream of a promoter.

22. The plant according to claim 21, wherein the DNA is obtained from *Vigna angularis*.

23. A plant having a heterologous expression vector introduced into the plant, wherein the heterologous expression vector comprises a DNA which codes for a protein in a 5'-3' direction having endo-xyloglucan transferase activity, wherein the complement of said DNA hybridizes with the sequence shown in SEQ ID NO. 15 under the following conditions:

solution: 5×Denhart's solution, 6×SSC, 0.1% SDS, 10 μg/ml salmon sperm DNA, hybridization: incubating at 50° C. overnight, said DNA being operably linked in a 5'-3' direction downstream of a promoter.

24. The plant according to claim 23, wherein the DNA is obtained from *Vigna angularis*.

25. A method for producing an endo-xyloglucan transferase, said method comprising, incubating a plant or cells transformed with a DNA coding for an endo-xyloglucan transferase to express the endo-xyloglucan in the plant or cells, wherein the DNA comprises the sequence shown in SEQ ID NO. 15, and recovering the endo-xyloglucan transferase from the culture.

26. The method according to claim 25, wherein the DNA is obtained from *Vigna angularis*.

27. A method for producing an endo-xyloglucan transferase, said method comprising incubating a plant or cells transformed with a DNA coding for an endo-xyloglucan transferase to express the endo-xyloglucan in the plant or cells, wherein the DNA comprises a DNA sequence whose complement hybridizes with the sequence shown in SEQ ID NO. 15 under the following conditions:

solution: 5×Denhart's solution, 6×SSC, 0.1% SDS, 10 μg/ml salmon sperm DNA hybridization: incubating at 50° C. overnight, and recovering the endo-xyloglucan transferase from the culture.

28. The method according to claim 27, wherein the DNA is obtained from *Vigna angularis*.

* * * * *